United States Patent
Yoon et al.

(10) Patent No.: US 12,011,497 B2
(45) Date of Patent: Jun. 18, 2024

(54) COMPOUNDS, COMPOSITIONS CONTAINING SAME, AND USE THEREOF FOR PROMOTING HAIR GROWTH

(71) Applicant: Molgenbio Co. Ltd., Seoul (KR)

(72) Inventors: Yeo Joon Yoon, Seoul (KR); Eunji Cheong, Seoul (KR); Seung-Woo Cho, Seoul (KR); Myoung-Chong Song, Seoul (KR); Ji Yoon Beom, Seoul (KR); Jin A Jung, Seoul (KR); Jong Seung Lee, Seoul (KR); Heon-Joo Lee, Seoul (KR)

(73) Assignee: Molgenbio Co. Ltd., Seoul (KR)

( * ) Notice: Subject to any disclaimer, the term of this patent is extended or adjusted under 35 U.S.C. 154(b) by 234 days.

(21) Appl. No.: 17/413,358

(22) PCT Filed: Dec. 11, 2019

(86) PCT No.: PCT/KR2019/017523
§ 371 (c)(1),
(2) Date: Jun. 11, 2021

(87) PCT Pub. No.: WO2020/122611
PCT Pub. Date: Jun. 18, 2020

(65) Prior Publication Data
US 2022/0257488 A1 Aug. 18, 2022

(30) Foreign Application Priority Data

Dec. 11, 2018 (KR) .......................... 10-2018-0158863
Jul. 17, 2019 (KR) .......................... 10-2019-0086645

(51) Int. Cl.
*A61K 8/49* (2006.01)
*A23L 29/00* (2016.01)
(Continued)

(52) U.S. Cl.
CPC .......... *A61K 8/4926* (2013.01); *A23L 29/045* (2016.08); *A23L 33/10* (2016.08);
(Continued)

(58) Field of Classification Search
None
See application file for complete search history.

(56) References Cited

U.S. PATENT DOCUMENTS

| 5,494,820 A | 2/1996 | Cullen et al. |
| 2006/0035918 A1* | 2/2006 | Hirayama ............ A61K 31/137 514/630 |
| 2007/0078175 A1 | 4/2007 | Boulle et al. |

FOREIGN PATENT DOCUMENTS

| KR | 2005/0071491 A | 7/2005 |
| KR | 2012/0019360 A | 3/2012 |
| WO | WO-90/14826 | 12/1990 |
| WO | 2011068341 A2 | 6/2011 |

OTHER PUBLICATIONS

Hordinsky, "Overview of Alopecia Areata", Journal of Investigative Dermatology Symposium Proceedings, vol. 16 (Year: 2013).*
(Continued)

*Primary Examiner* — Bethany P Barham
*Assistant Examiner* — Barbara S Frazier
(74) *Attorney, Agent, or Firm* — Morse, Barnes-Brown & Pendleton, P.C.; Martin Z. Zhang; Russell L. Widom

(57) ABSTRACT

Provided are preparation and use of novel compounds available as main ingredients of a composition for promoting hair growth, wherein the novel compounds are 9-deoxo-31-O-demethyl-prolyl-FK506, 9-deoxo-36,37-dihydro-FK506, 31-O-demethyl-36,37-dihydro-FK506, 9-deoxo-31-O-demethyl-36,37-dihydro-FK506, 9-deoxo-FK520, 31-O-demethyl-FK520, 9-deoxo-31-O-demethyl-FK520, 9-deoxo-FK523, and 9-deoxo-31-O-demethyl-FK523.

11 Claims, 56 Drawing Sheets
Specification includes a Sequence Listing.

(51) Int. Cl.
  *A23L 33/10* (2016.01)
  *A61K 31/407* (2006.01)
  *A61K 31/436* (2006.01)
  *A61P 17/14* (2006.01)
  *A61Q 7/00* (2006.01)

(52) U.S. Cl.
  CPC .......... *A61K 31/407* (2013.01); *A61K 31/436* (2013.01); *A61P 17/14* (2018.01); *A61Q 7/00* (2013.01)

(56) References Cited

OTHER PUBLICATIONS

Extended European Search Report issued in European Patent Application No. 19 896 434.8 dated Oct. 11, 2022.

Goulet et al "Alkyl Ether Derivatives of the FK-506 Related, Immunosuppressive Macrolide L-683,742 (C31-O-Desmethyl Ascomycin)", Bioorganic and Medicinal Chemistry Letters, vol. 4, pp. 927-930, 1994.

Park et al "Liquid Chromatography-Mass Spectrometry Characterization of FK506 Biosynthetic Intermediates in *Streptomyces clavuligerus* KCTC 10561BP", Analytical Biochemistry, vol. 393, pp. 1-7, Jun. 2009.

Iwabuchi et al "Effects of Immunosuppressive Peptidyl-Prolyl Cis-Trans Isomerase (PPlase) Inhibitors, Cyclosporin A, FK506, Ascomycin and Rapamycin, on Hair Growth Initiation in Mouse: Immunosuppression is Not Required for New Hair Growth" Journal of Dermatological Science vol. 9, pp. 64-69, 1995.

Yamamoto et al "Stimulation of Hair Growth by Topical Application of FK506, a Potent Immunosuppressive Agent" The Journal of Investigative Dermatology vol. 102, pp. 160-164, 1994.

Office Action in Chinese Application No. 2019800918828 dated Mar. 27, 2024 (English translation).

* cited by examiner 9-deoxo-31-O-demethyl-FK520

0µM           1µM           5µM

SEQUENCE LISTING

```
<160> NUMBER OF SEQ ID NOS: 20

<210> SEQ ID NO 1
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 1
tataaagctt cggagccccg gtggacct                                          28

<210> SEQ ID NO 2
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 2
ttaatctaga cgtcgcctcg tcgtcgct                                          28

<210> SEQ ID NO 3
<211> LENGTH: 28
<212> TYPE: DNA
<213> ORGANISM: Artificial Sequence
<220> FEATURE:
```

<223> OTHER INFORMATION: Synthetic oligonucleotide

<400> SEQUENCE: 3
gtaatctaga gtcggctact gcctctac                                              28

<210> SEQ ID NO 4
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 4
gaatgaattc cgacgaacag cggttcct                                              28

<210> SEQ ID NO 5
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 5
tacgaagctt tctgttcggc atccagca                                              28

<210> SEQ ID NO 6
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 6
tagctctaga gtcacccggg agcagttc                                              28

<210> SEQ ID NO 7
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 7
tatatctaga gacaccgaag gcgcgctc                                              28

<210> SEQ ID NO 8
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 8
ttaagaattc gaacaccgag gccgtcca                                              28

<210> SEQ ID NO 9
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 9
tataaagctt cggagccccg gtggacct                                              28

```
<210> SEQ ID NO 10
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 10
ttaatctaga cgtcgcctcg tcgtcgct                                          28

<210> SEQ ID NO 11
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 11
tatatctaga gacaccgaag gcgcgctc                                          28

<210> SEQ ID NO 12
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 12
ttaagaattc gaacaccgag gccgtcca                                          28

<210> SEQ ID NO 13
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 13
gacaagctta tgctggcggt gaaggcg                                           27

<210> SEQ ID NO 14
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 14
ccgtctagac cagaaggaat cgagccggaa                                        30

<210> SEQ ID NO 15
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 15
cagtctagag tgatccgtgc cctgcactcc                                        30

<210> SEQ ID NO 16
<211> LENGTH: 28
<212> TYPE: DNA
<213> ORGANISM: Artificial Sequence
<220> FEATURE:
<223> OTHER INFORMATION: Synthetic oligonucleotide
```

-continued

```
<400> SEQUENCE: 16
gccgaattcg atgacgatgt ccgggtcg                                              28

<210> SEQ ID NO 17
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 17
gctaagcttc tcaggcgtct gcggatgc                                              28

<210> SEQ ID NO 18
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 18
atcggatcct tcgctcaccg gggctgcc                                              28

<210> SEQ ID NO 19
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 19
agcagatctg gcatgttctg gtcagtcc                                              28

<210> SEQ ID NO 20
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 20
gtcgaattcc atgccacgaa cgggtcga                                              28
```

COMPOUNDS, COMPOSITIONS CONTAINING SAME, AND USE THEREOF FOR PROMOTING HAIR GROWTH

CROSS REFERENCE TO RELATED APPLICATIONS

This application is the National Stage of International Application No. PCT/KR2019/017523, filed on Dec. 11, 2019, which claims priority to Korean Application No. 10-2018-0158863, filed on Dec. 11, 2018, and Korean Application No. 10-2019-0086645, filed on Jul. 17, 2019. The contents of these applications are hereby incorporated by reference in their entirety.

TECHNICAL FIELD

The present invention relates to preparation and use of novel compounds available as main ingredients of a composition for promoting hair growth, wherein the novel compounds are 9-deoxo-31-O-demethyl-prolyl-FK506, 9-deoxo-36,37-dihydro-FK506, 31-O-demethyl-36,37-dihydro-FK506, 9-deoxo-31-O-demethyl-36,37-dihydro-FK506, 9-deoxo-FK520, 31-O-demethyl-FK520, 9-deoxo-31-O-demethyl-FK520, 9-deoxo-FK523, and 9-deoxo-31-O-demethyl-FK523. More particularly, the present invention relates to methods of preparing the novel compounds and compositions for promoting hair growth including each of the novel compounds as an active ingredient.

BACKGROUND ART

Hair loss (alopecia) in modern people has become more common not only due to aging or genetic causes but also due to the influence of acquired factors such as hormone imbalance caused by environmental contamination, smoking, stress from work, and changes in dietary patterns. While the population with hair loss has increased mainly in middle-aged and elderly male people around in their 40s to 50s, the number of younger people and females suffering from hair loss has also been increasing in recent years.

According to statistical analysis of the Korean Society of Hair Restoration Treatment, the population with hair loss domestically accounts for about 10 million including potential alopecia patients. The medical expenditure therefor was about 35.5 billion won in 2016, and the number of people with hair loss is increasing abroad as well as in Korea. The market size for hair loss management in the U.S., measured by IBIS World Industry Market Research, was 3.6 billion dollars in 2016 and is projected to grow at a rate of 0.7% every year until 2021.

Meanwhile, according to a survey of the Korean Association of Chronic Disease Management, seven out of 10 Korean adults recognize hair loss as a disease and think that hair loss causes direct or indirect losses in social lives. Also, about 23% of adults experience hair loss.

Alopecia is classified into non-cicatricial alopecia, which is temporary hair loss, and cicatricial alopecia caused by permanent destruction of hair follicles or hair roots. Non-cicatricial alopecia is a common form of hair loss, and is classified into infectious hair loss, traumatic hair loss, inflammatory hair loss, congenital hair loss, endocrine hair loss, neoplastic alopecia, malnutrition hair loss, drug-induced hair loss. Hair loss caused by abnormal hair structure, male- and female-pattern hair loss, and alopecia areata also belong to non-cicatricial alopecia.

As the economy grows and society ages, hair loss has been considered as a disease rather than an uncontrollable phenomenon, and there is a need to develop drugs effective in the treatment of hair loss, which causes psychological anxiety and stress in work and social lives.

However, although the number of people with hair loss is increasing, the exact causes of hair loss have not been identified, and there are no effective methods for preventing hair loss. Due to the current situation, effective technologies for preventing hair loss and promoting hair growth have gained more interest, and a variety of prevention agents are present on the market.

Currently, Minoxidil for topical administration and Propecia for oral administration are drugs approved by the FDA. However, these drugs do not provide permanent therapeutic effects, but only provide effects on delaying the progression of hair loss or maintaining the current state. In addition, topical hair growth-promoting agents such as Minoxidil may be troublesome since they need to be applied every day to maintain the effects on promoting hair growth, and have lesser effects than orally administered agents. In addition, Propecia may increase the likelihood of congenital malformations in infants when administered to females, and may cause side effects such as sexual dysfunction. Therefore, there is a need to develop drugs capable of providing fundamental therapeutic effects beyond the level of temporary effects. Moreover, drugs available not only for therapeutic use but also for preventive use may be more valuable.

Although Korean Patent Laid-open Publication No. 10-2005-0071491 (Title of Invention: Use of tacrolimus (FK506) derivatives combined with beta2-agonists for treatment of asthma) discloses a novel use of FK506 derivatives and beta2-agonists for manufacturing a medicament for simultaneous, separate, or sequential use to treat or prevent acute or chronic asthma, there have been no studies on applying FK506 derivatives, FK520 derivatives, or FK523 derivatives to promote hair growth.

DISCLOSURE

Technical Problem

An object of the present invention is to provide the nine novel compounds, isomers thereof, or pharmaceutically acceptable salts thereof.

Another object of the present invention is to provide a composition for promoting hair growth including at least one selected from the nine novel compounds as an active ingredient. In this regard, the composition for promoting hair growth refers to a composition for alleviating, preventing, or treating hair loss.

Another object of the present invention is to provide a pharmaceutical composition for promoting hair growth including at least one selected from isomers of the nine novel compounds or pharmaceutically acceptable salts thereof as an active ingredient. In this regard, the pharmaceutical composition for promoting hair growth refers to a composition for alleviating, preventing, or treating hair loss.

Another object of the present invention is to provide biological manufacturing processes of each of the nine novel compounds.

Another object of the present invention is to provide production strains available in biological manufacturing processes the nine novel compounds, *Streptomyces kanamyceticus* ΔfkbD-fkbM (accession number: KCTC13581BP), *Streptomyces kanamyceticus* ΔfkbD,tcsD (accession number: KCTC13580BP), *Streptomyces kanamyceticus* ΔfkbM, tcsD (accession number: KCTC13584BP), *Streptomyces kanamyceticus* ΔfkbD-fkbM,tcsD (accession number: KCTC13585BP), *Streptomyces kanamyceticus* ΔfkbD,tcsB (accession number: KCTC13579BP), *Streptomyces kanamyceticus* ΔfkbM,tcsB (accession number: KCTC13583BP), and *Streptomyces kanamyceticus* ΔfkbD-fkbM,tcsB (accession number: KCTC13582BP).

Another object of the present invention is to provide an over-the-counter (OTC) composition for promoting hair growth including at least one selected from the nine novel compounds, an isomer thereof, or a pharmaceutically acceptable salt thereof as an active ingredient.

Another object of the present invention is to provide a functional food composition for promoting hair growth including at least one selected from the nine novel compounds, an isomer thereof, or a sitologically acceptable salt thereof as an active ingredient.

Another object of the present invention is to provide a cosmetic composition for promoting hair growth including at least one selected from the nine novel compounds, an isomer thereof, or a cosmetically acceptable salt thereof as an active ingredient.

Technical Solution

As a result of intensive efforts, the present inventors have found hair growth-promoting effects of novel compounds, 9-deoxo-31-O-demethyl-prolyl-FK506, 9-deoxo-36,37-dihydro-FK506, 31-O-demethyl-36,37-dihydro-FK506, 9-deoxo-31-O-demethyl-36,37-dihydro-FK506, 9-deoxo-FK520, 31-O-demethyl-FK520, 9-deoxo-31-O-demethyl-FK520, 9-deoxo-FK523, and 9-deoxo-31-O-demethyl-FK523 (hereinafter collectively referred to as nine novel compounds), available as main ingredients of compositions for promoting hair growth, have developed manufacturing processes thereof and compositions for promoting hair growth using the compounds as active ingredients, and confirmed that the compositions may be effectively used as compositions for promoting hair growth, thereby completing the present invention.

Advantageous Effects

The composition for promoting hair growth including at least one selected from the nine novel compounds according to the present invention as an active ingredient may provide effects on promoting hair growth in alleviation, prevention, and treatment of hair loss, thereby providing fundamental preventive and therapeutic effects.

BEST MODE

Figure 1:
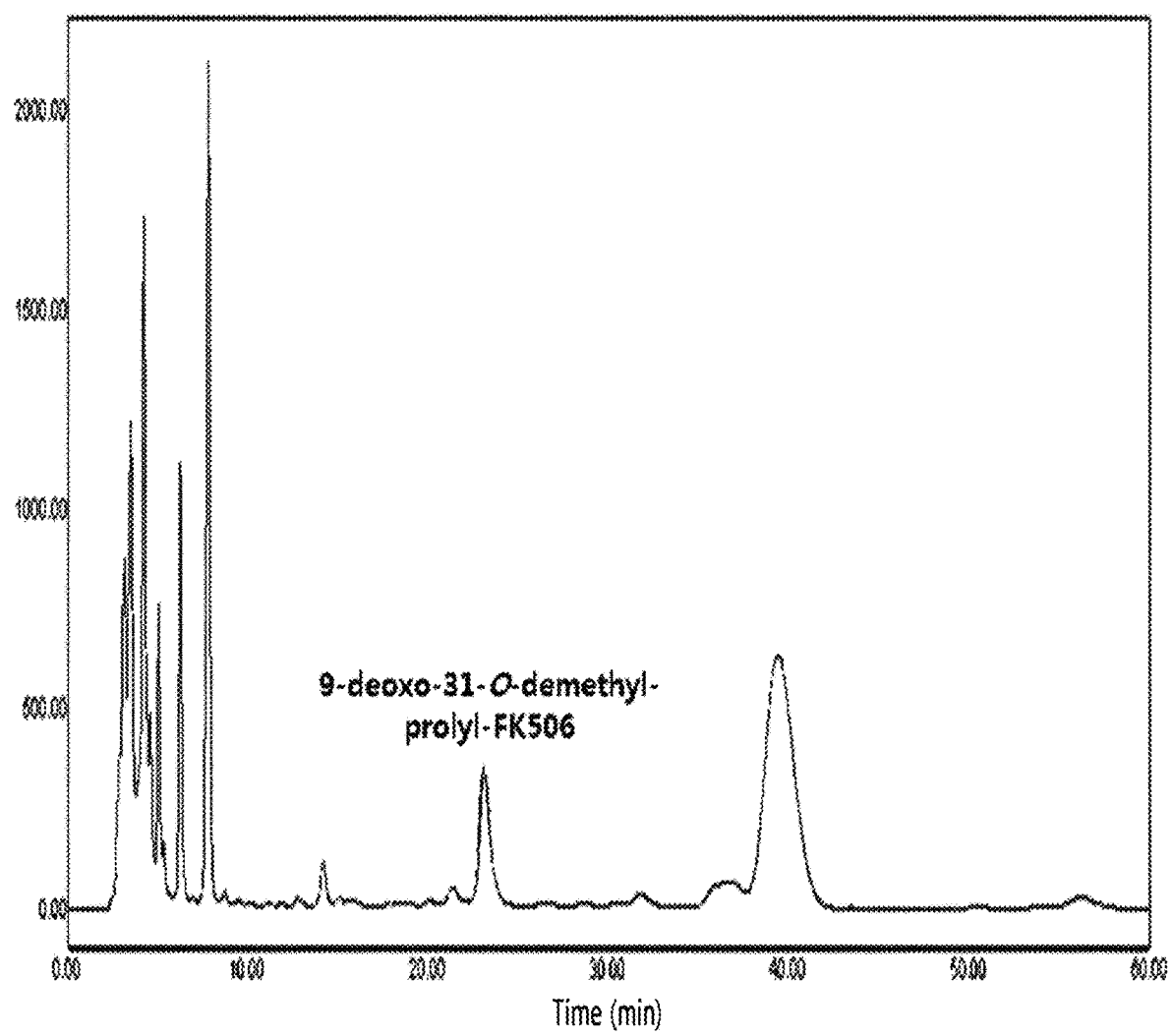
FIG. 1 shows high-performance liquid chromatography analysis results of 9-deoxo-31-O-demethyl-prolyl-FK506.
Figure 2:
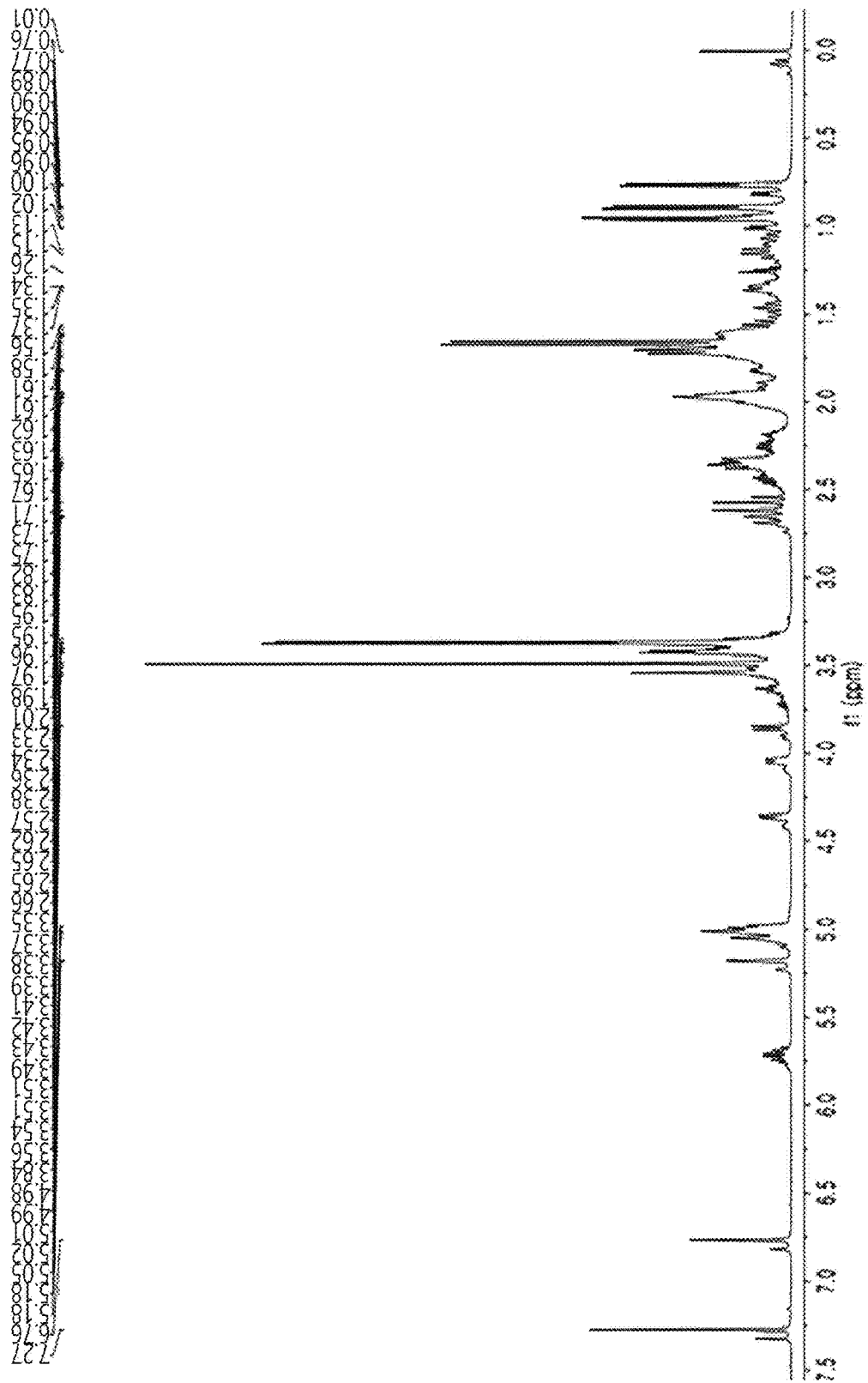
FIG. 2 shows nuclear magnetic resonance analysis ($^1$H-NMR) results of 9-deoxo-31-O-demethyl-prolyl-FK506.
Figure 3:
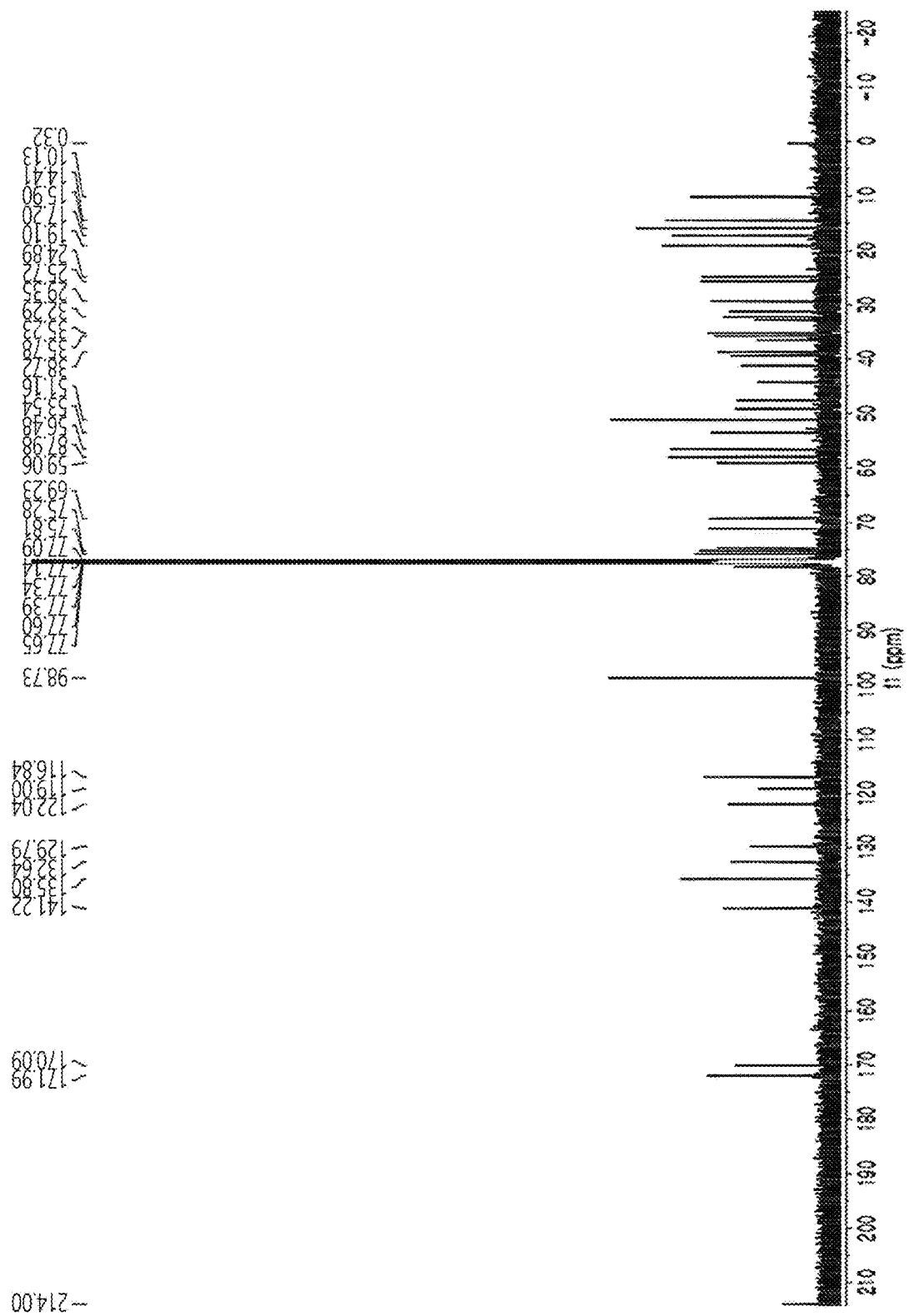
FIG. 3 shows nuclear magnetic resonance analysis ($^{13}$C-NMR) results of 9-deoxo-31-O-demethyl-prolyl-FK506.
Figure 4:
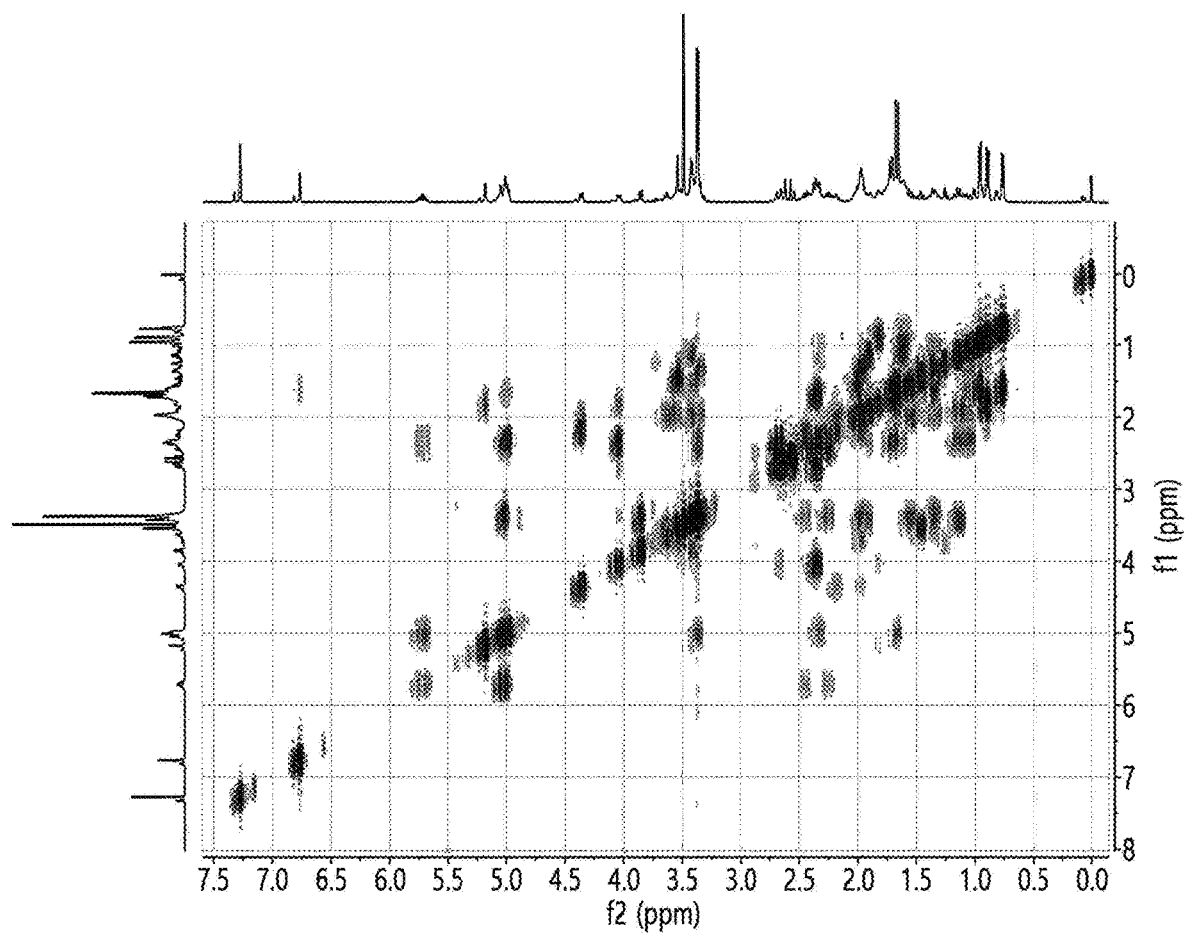
FIG. 4 shows nuclear magnetic resonance analysis (COSY-NMR) results of 9-deoxo-31-O-demethyl-prolyl-FK506.
Figure 5:
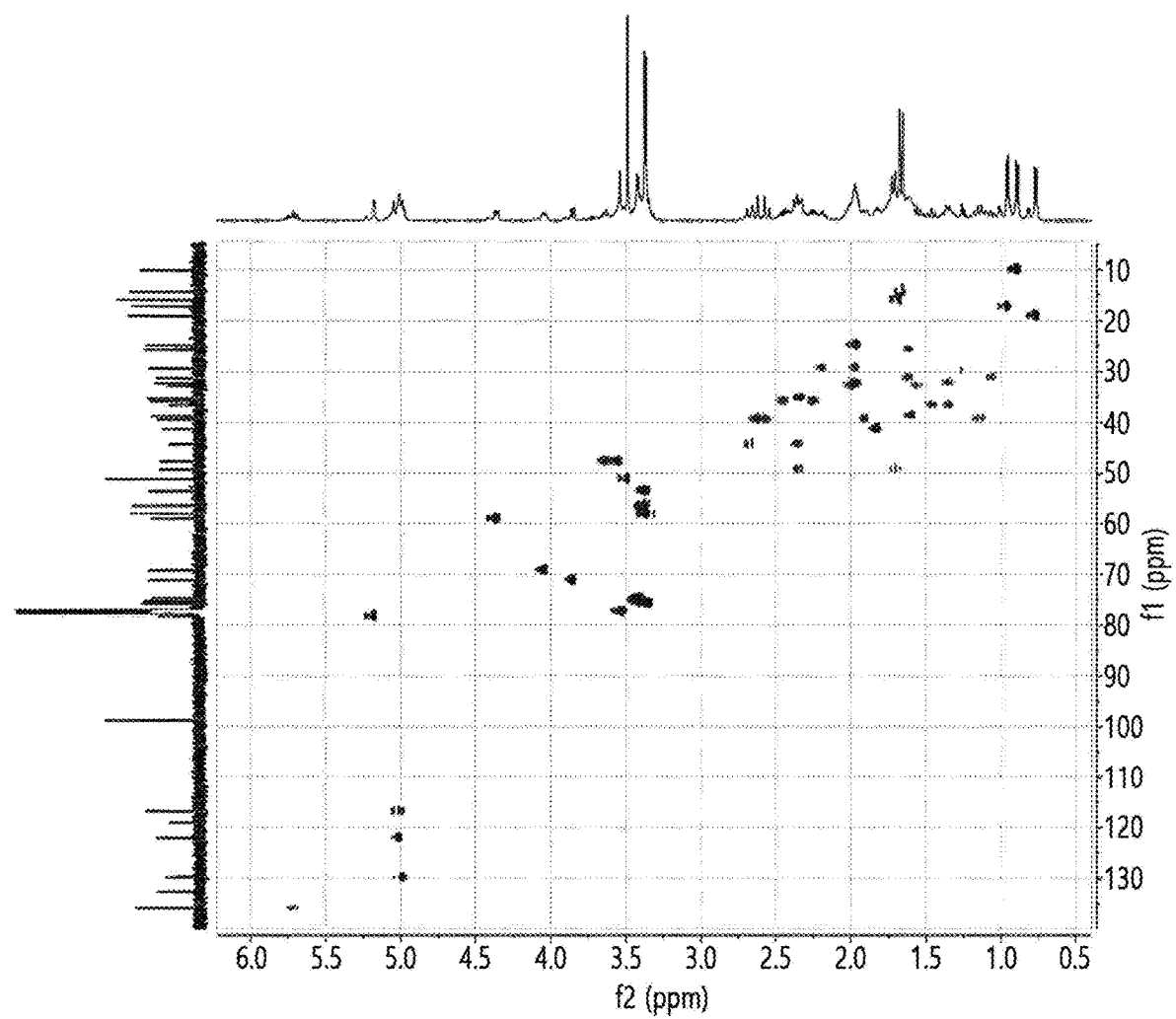
FIG. 5 shows nuclear magnetic resonance analysis (HSQC-NMR) results of 9-deoxo-31-O-demethyl-prolyl-FK506.
Figure 6:
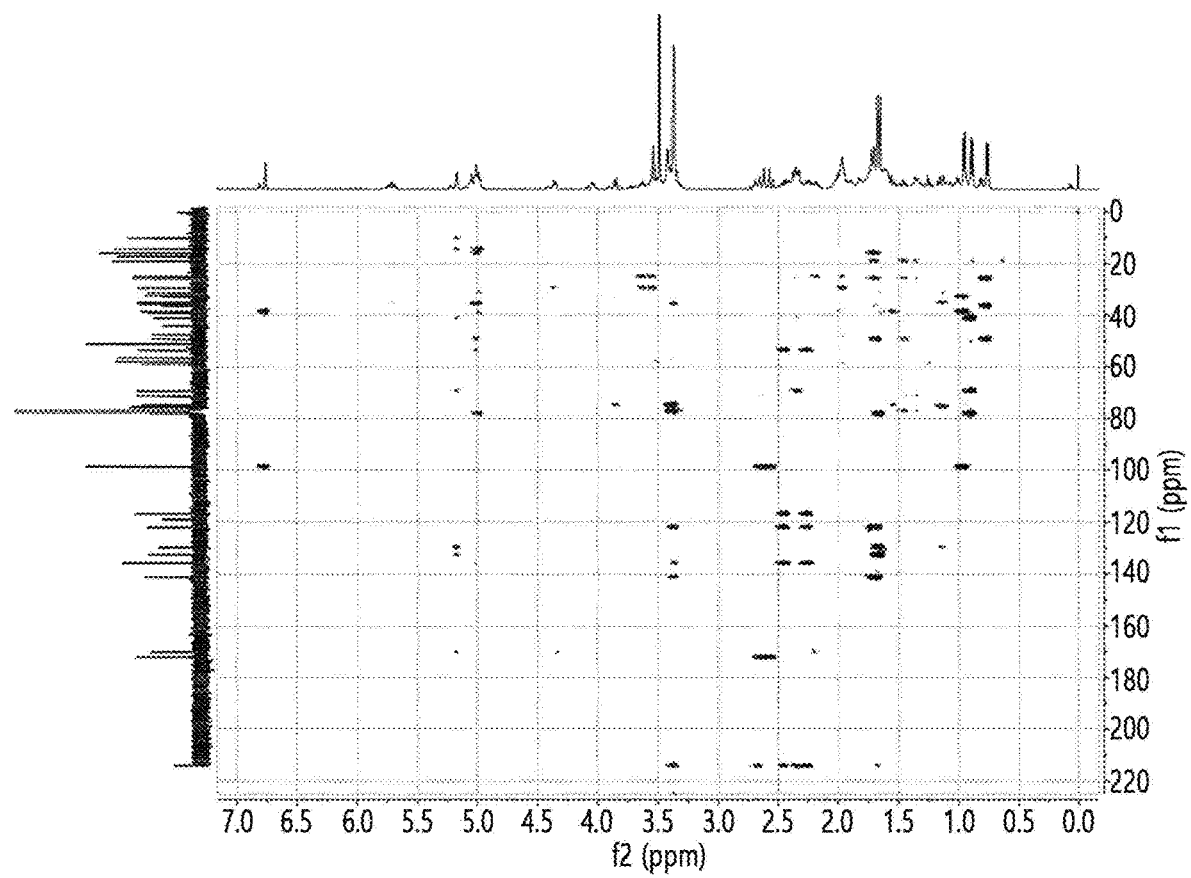
FIG. 6 shows nuclear magnetic resonance analysis (HMBC-NMR) results of 9-deoxo-31-O-demethyl-prolyl-FK506.
Figure 7:
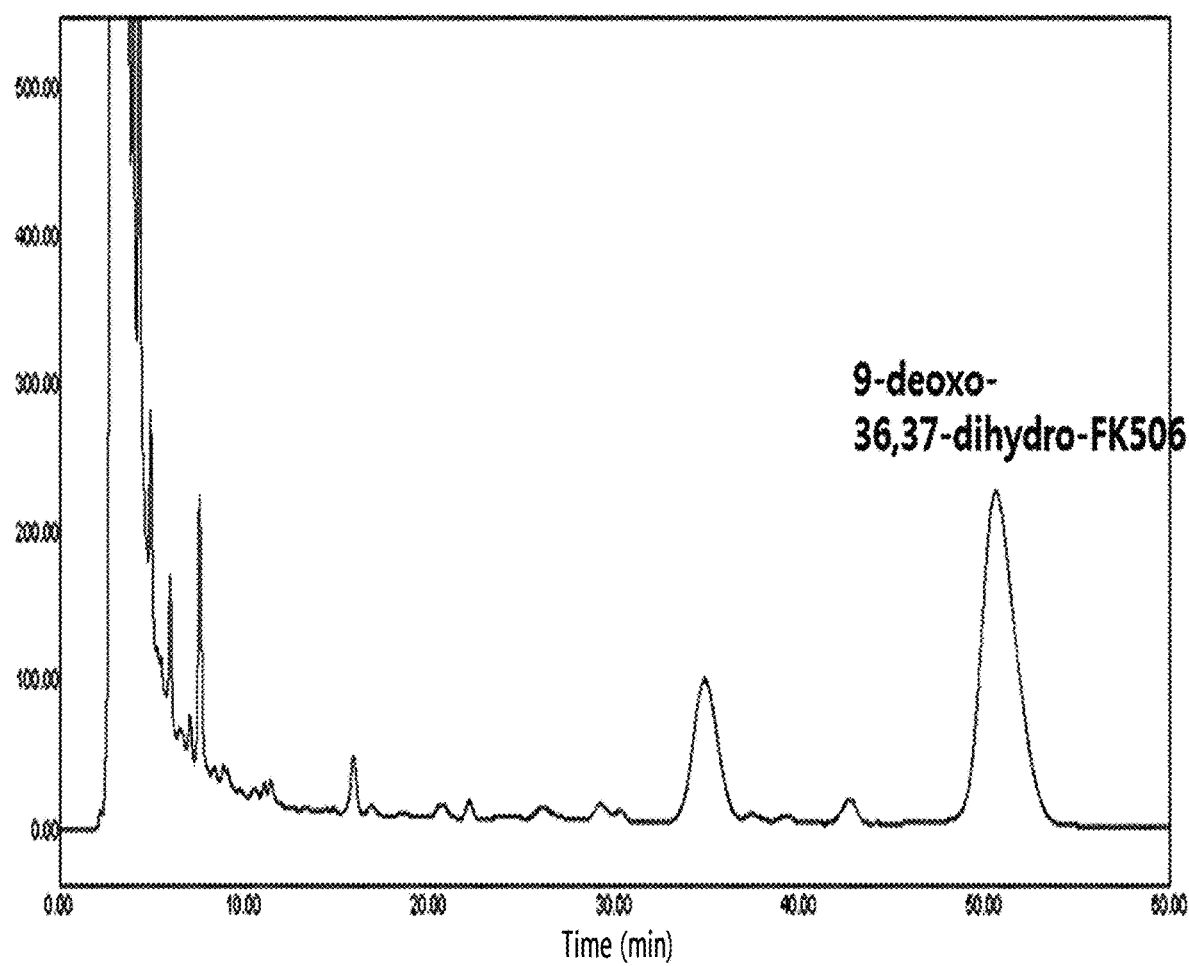
FIG. 7 shows high-performance liquid chromatography analysis results of 9-deoxo-36,37-dihydro-FK506.
Figure 8:
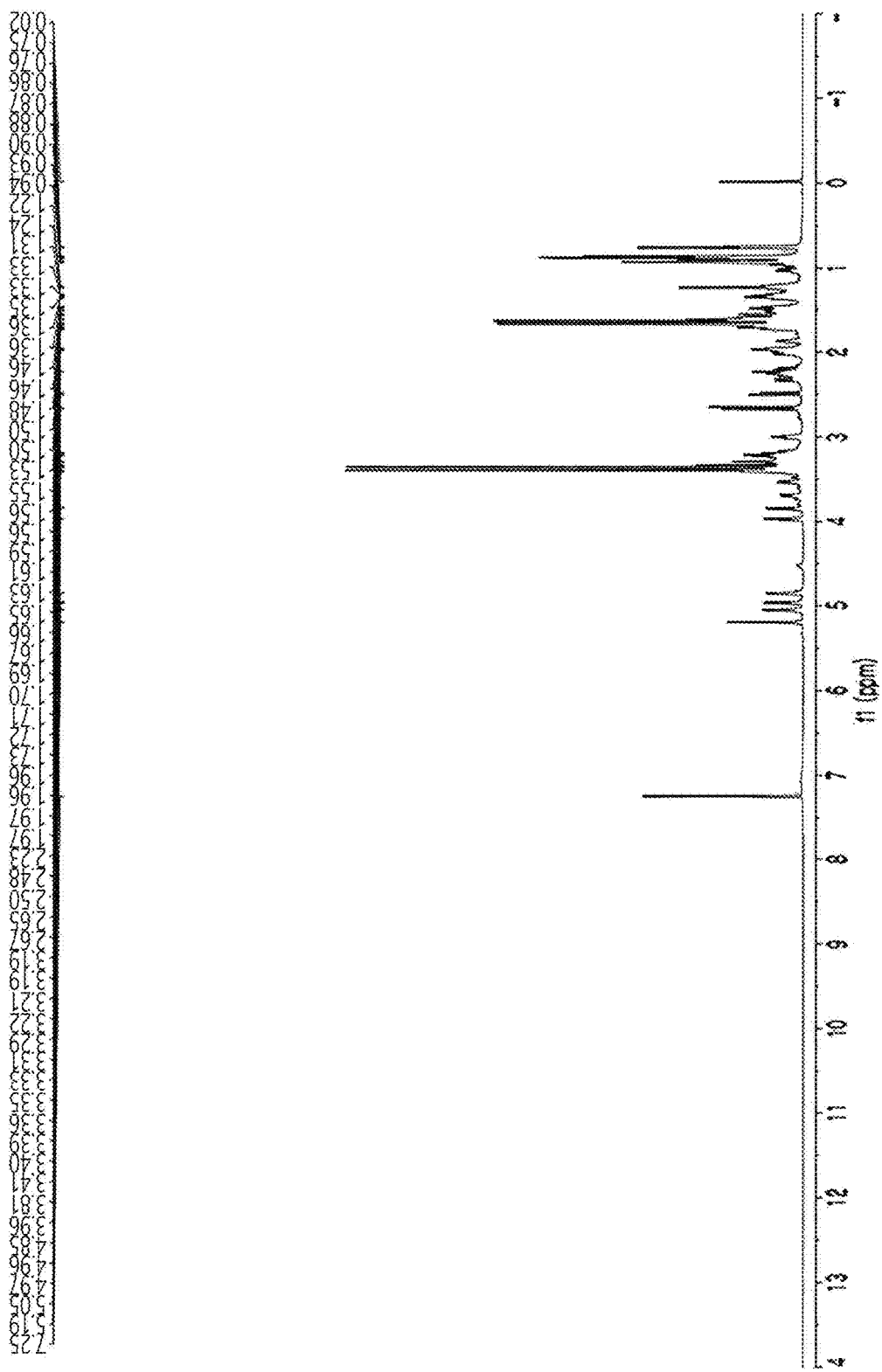
FIG. 8 shows nuclear magnetic resonance analysis ($^1$H-NMR) results of 9-deoxo-36,37-dihydro-FK506.
Figure 9:
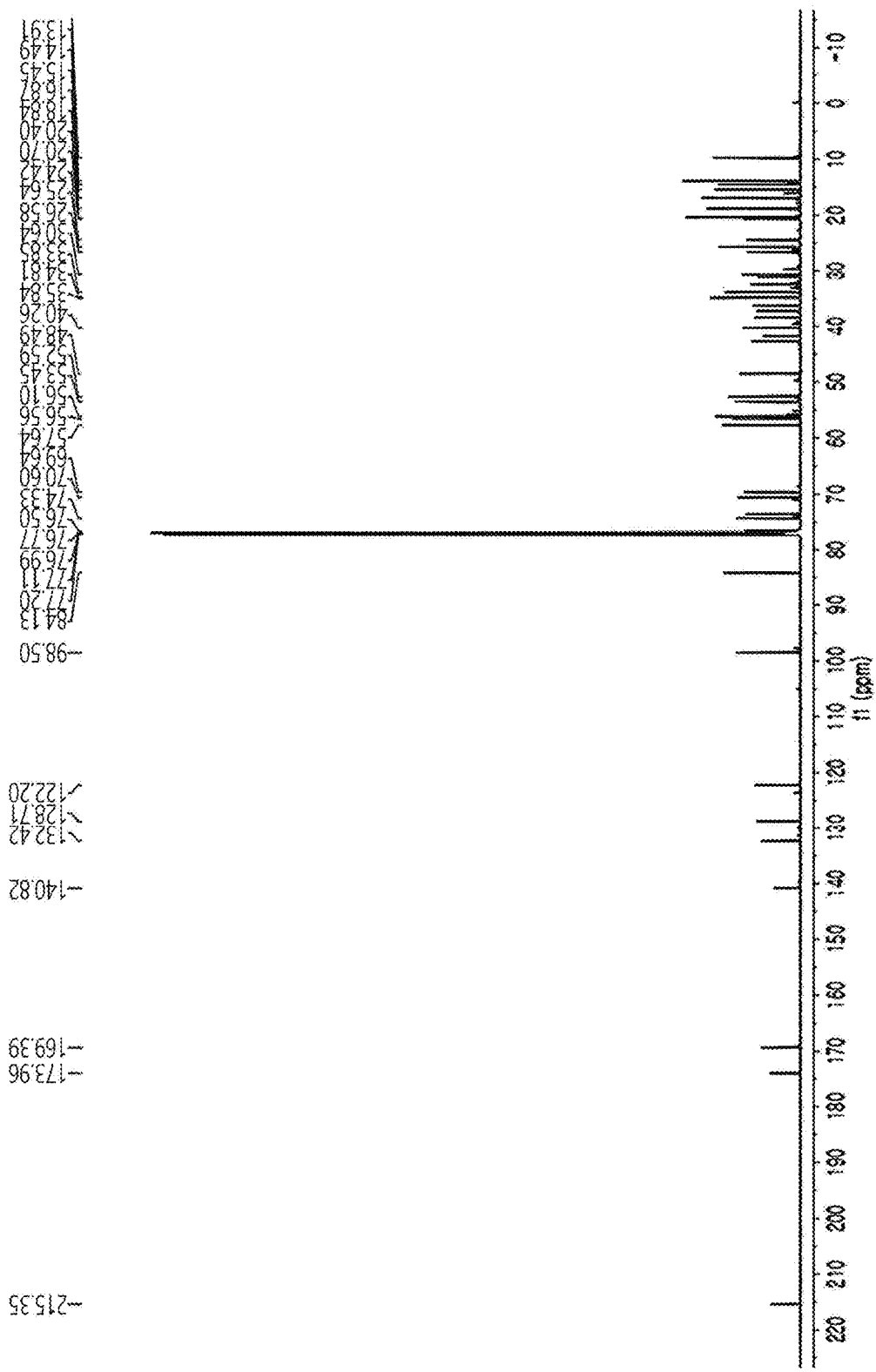
FIG. 9 shows nuclear magnetic resonance analysis ($^{13}$C-NMR) results of 9-deoxo-36,37-dihydro-FK506.
Figure 10:
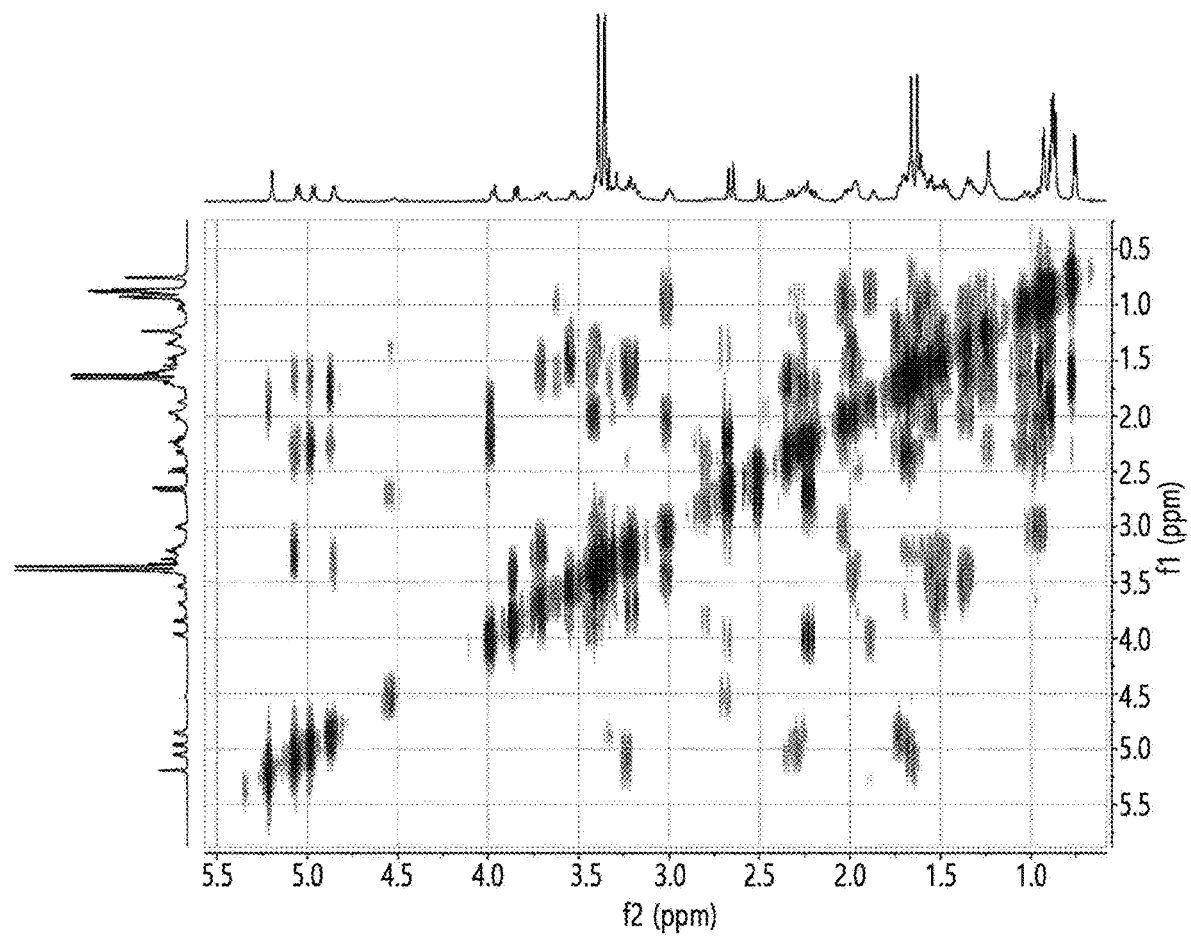
FIG. 10 shows nuclear magnetic resonance analysis (COSY-NMR) results of 9-deoxo-36,37-dihydro-FK506.
Figure 11:
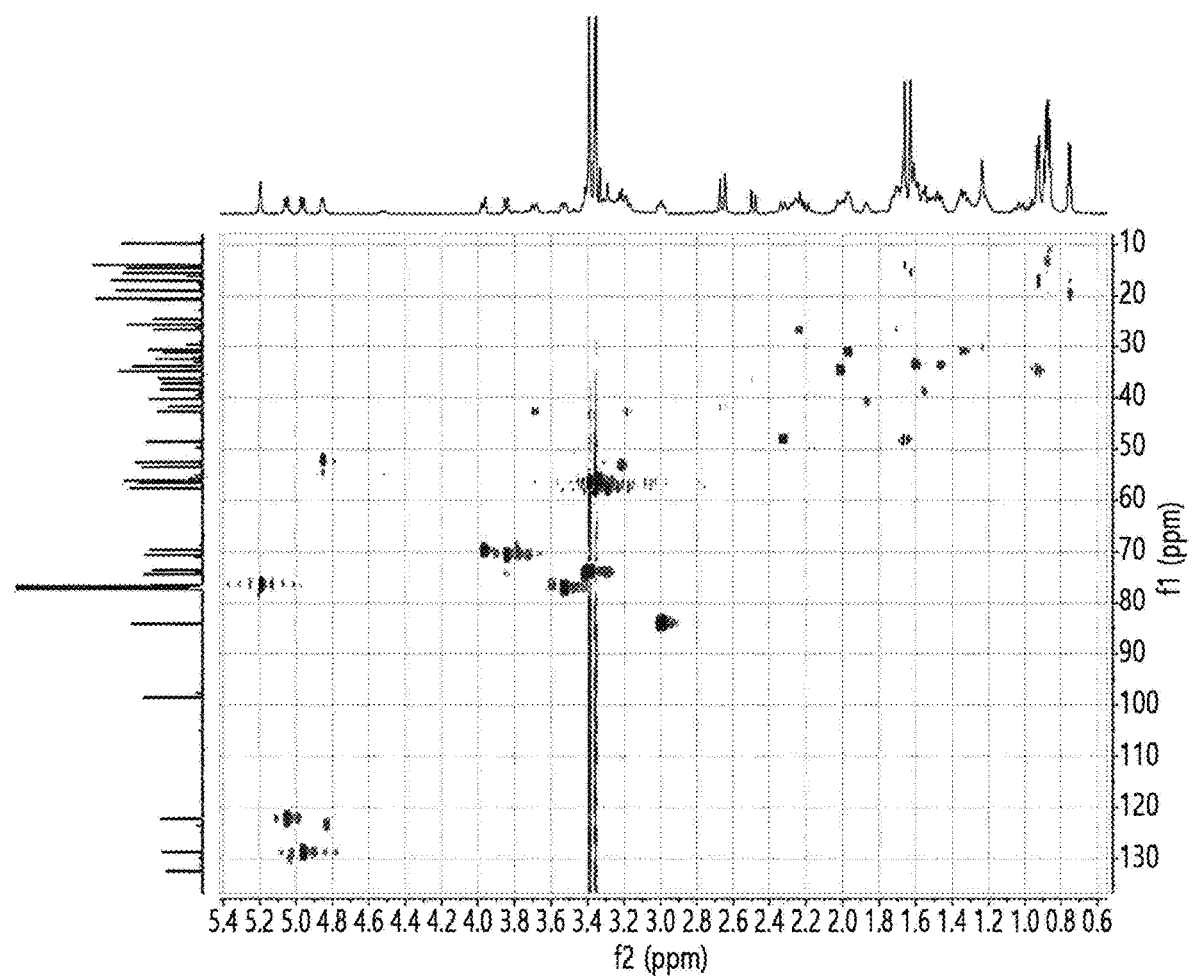
FIG. 11 shows nuclear magnetic resonance analysis (HSQC-NMR) results of 9-deoxo-36,37-dihydro-FK506.
Figure 12:
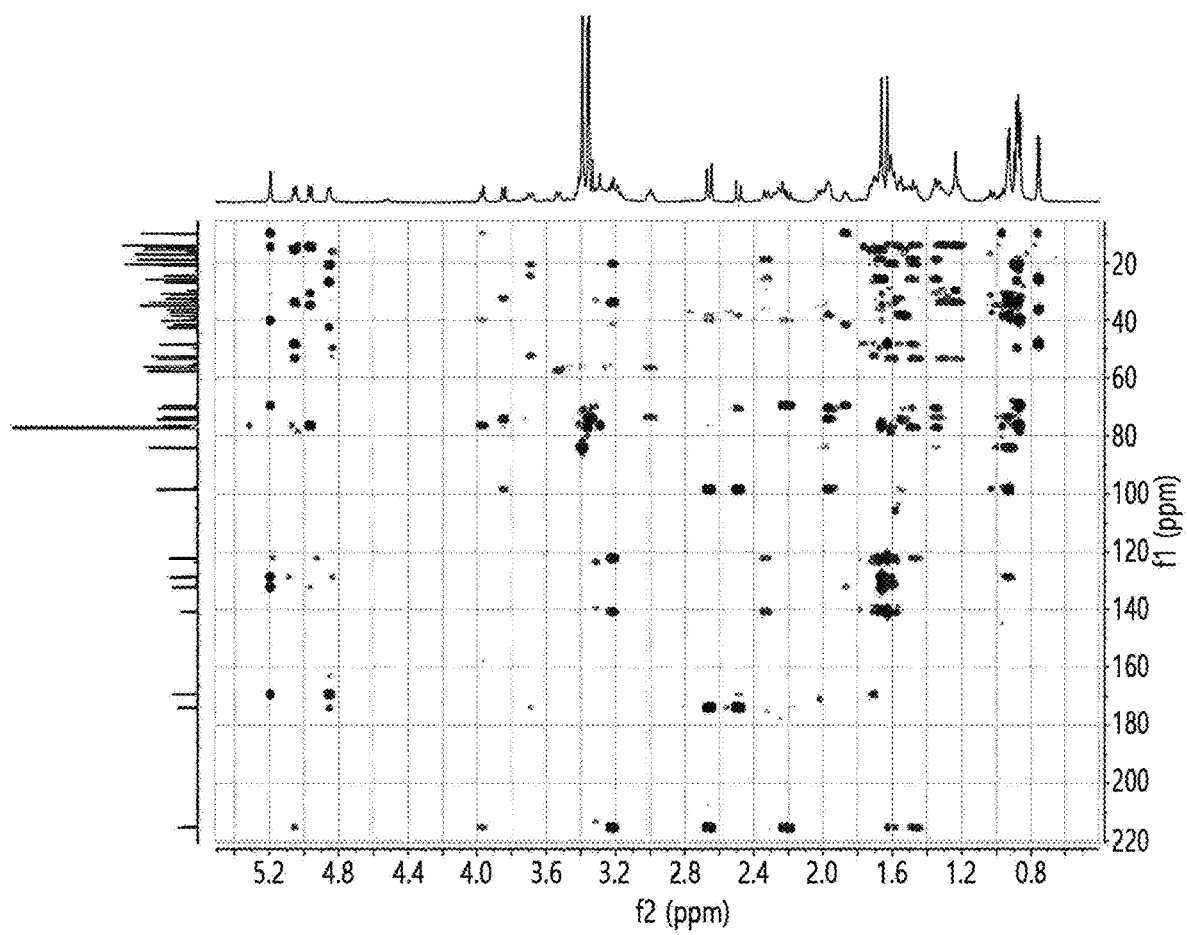
FIG. 12 shows nuclear magnetic resonance analysis (HMBC-NMR) results of 9-deoxo-36,37-dihydro-FK506.
Figure 13:
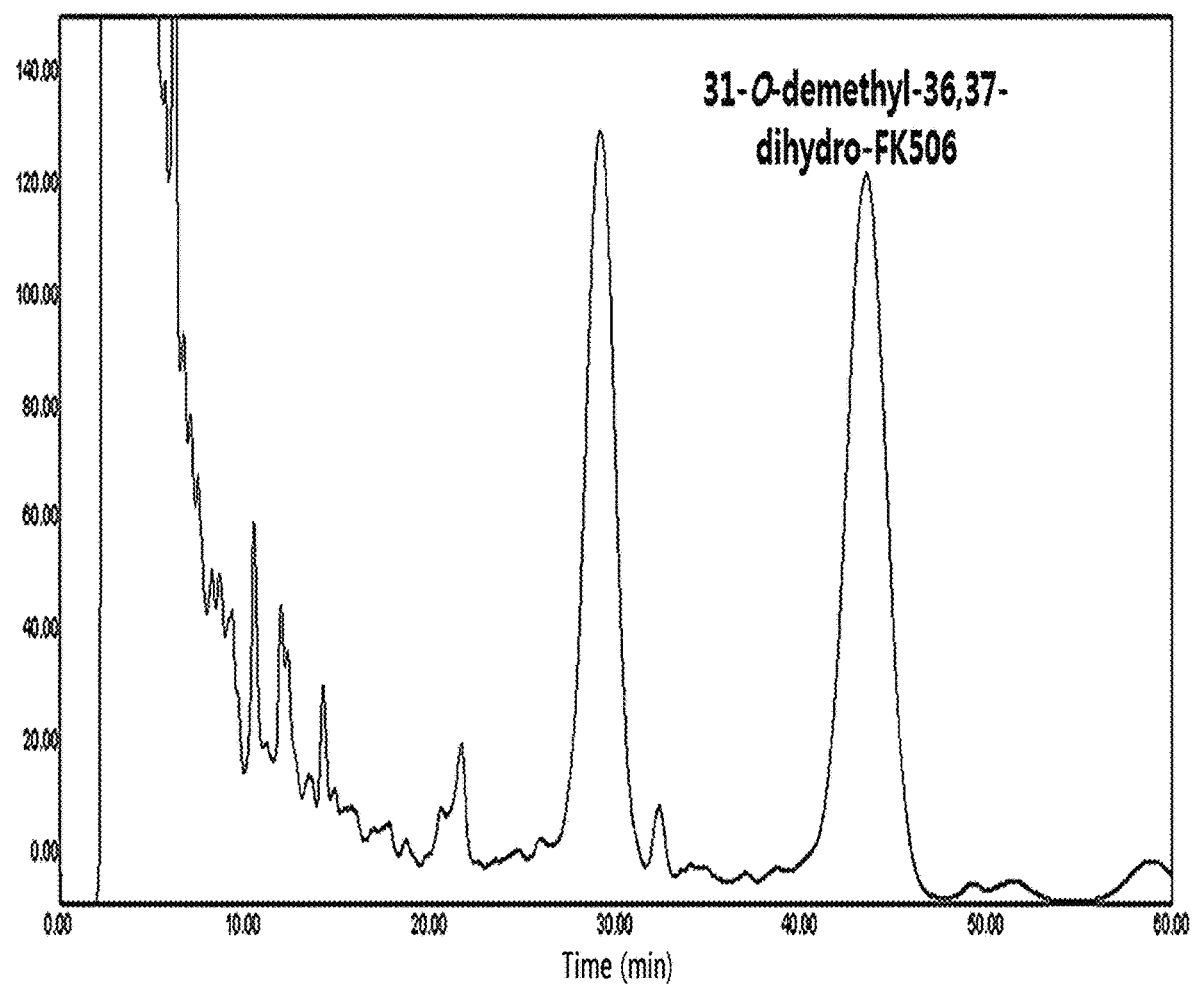
FIG. 13 shows high-performance liquid chromatography analysis results of 31-O-demethyl-36,37-dihydro-FK506.
Figure 14:
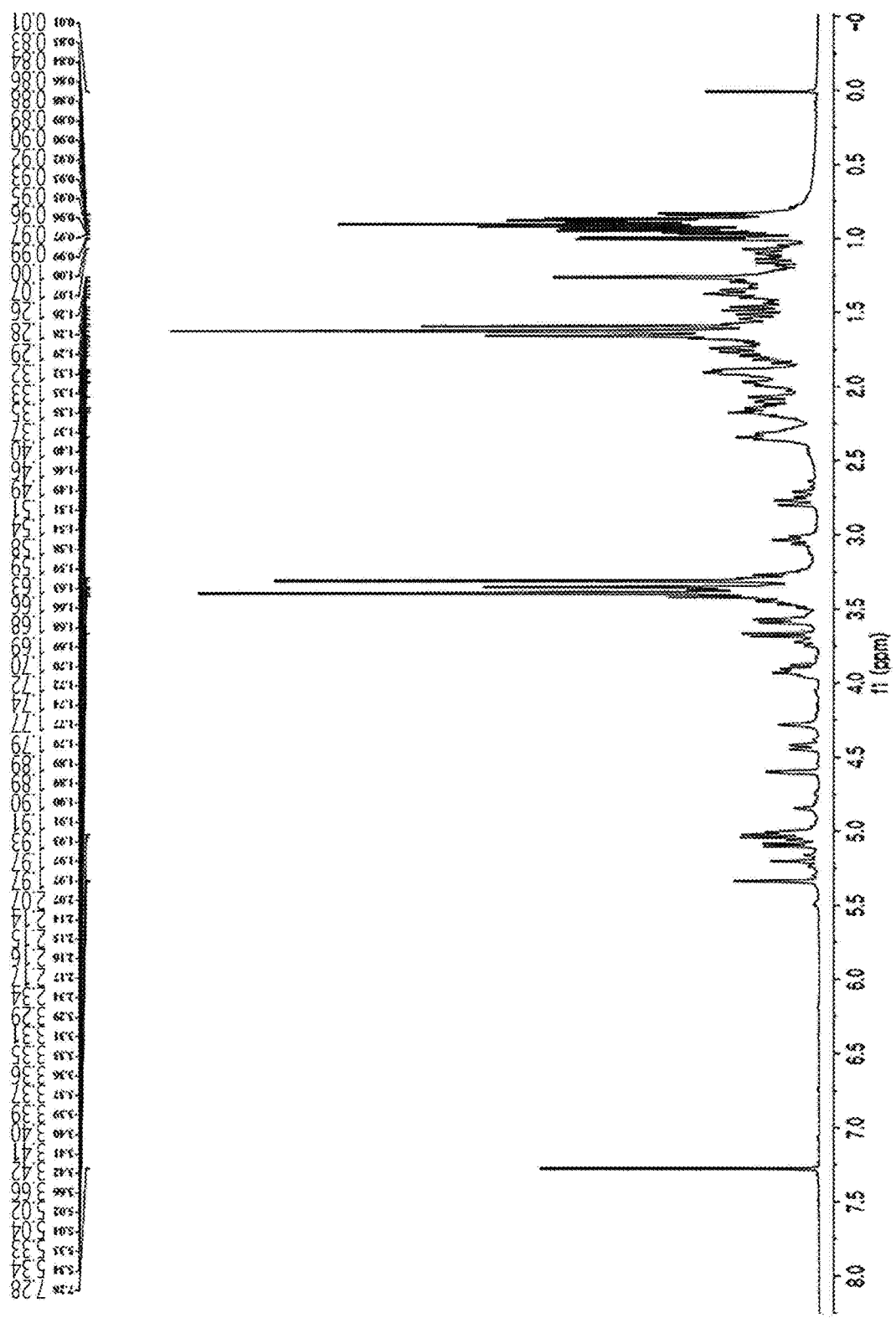
FIG. 14 shows nuclear magnetic resonance analysis ($^1$H-NMR) results of 31-O-demethyl-36,37-dihydro-FK506.
Figure 15:
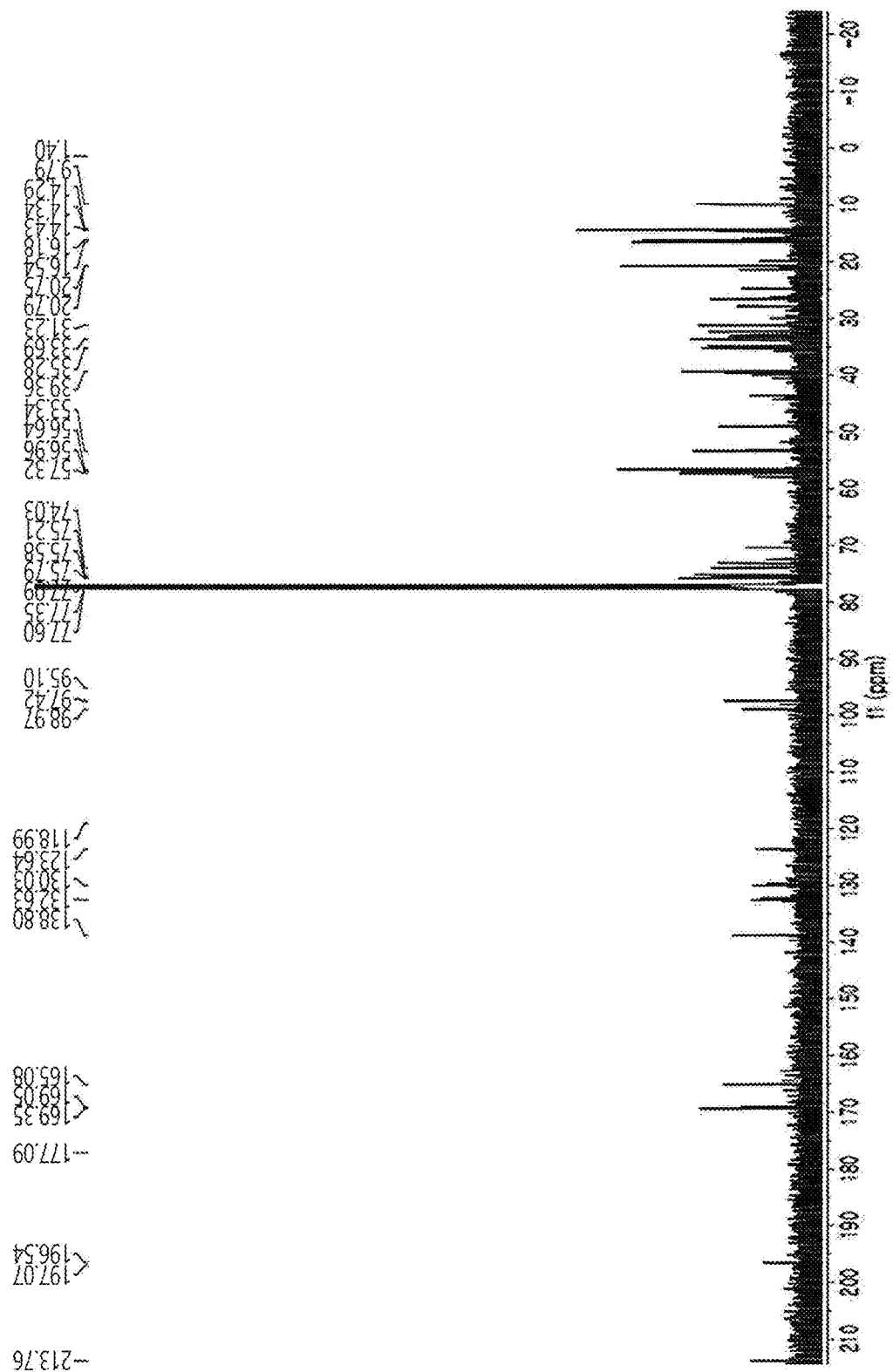
FIG. 15 shows nuclear magnetic resonance analysis ($^{13}$C-NMR) results of 31-O-demethyl-36,37-dihydro-FK506.
Figure 16:
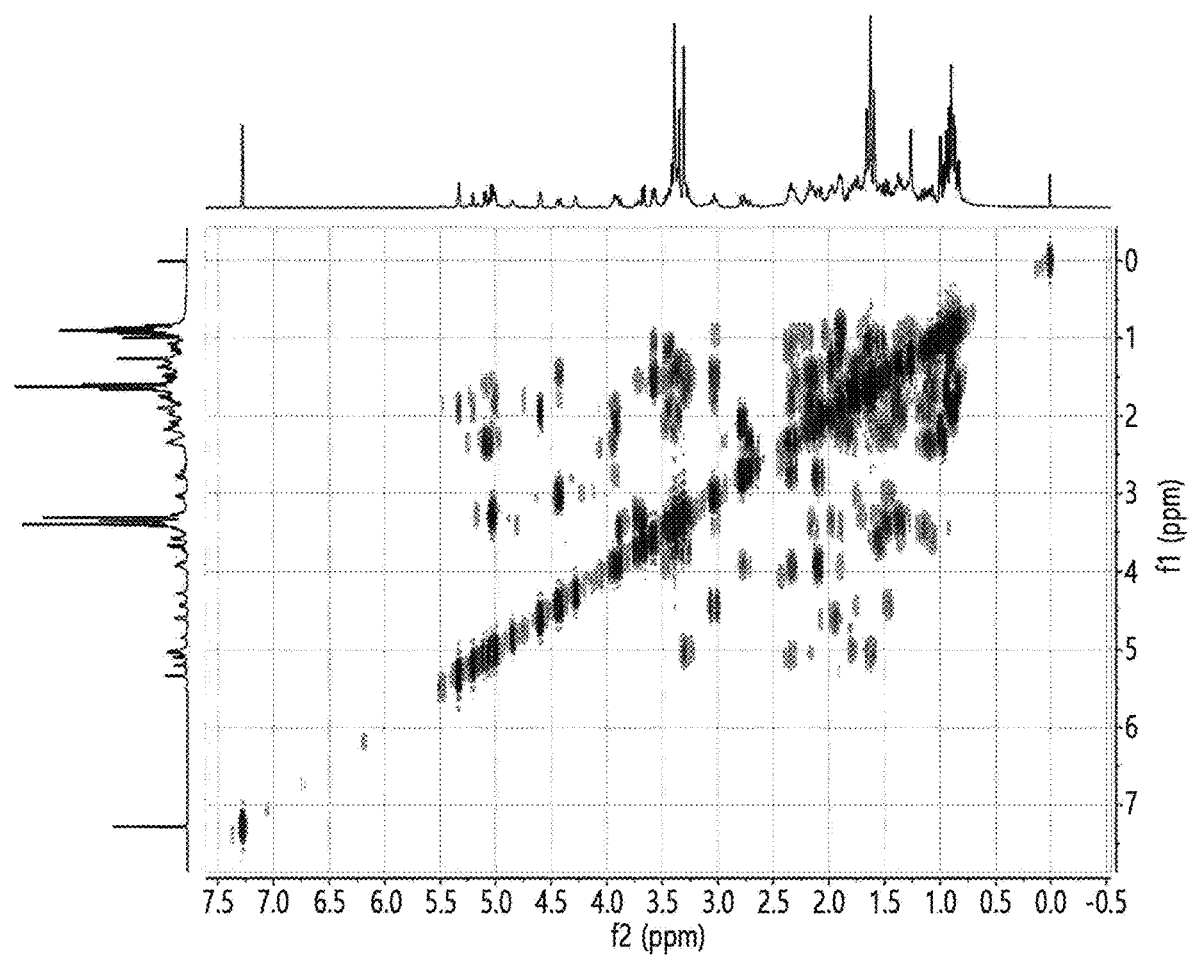
FIG. 16 shows nuclear magnetic resonance analysis (COSY-NMR) results of 31-O-demethyl-36,37-dihydro-FK506.
Figure 17:
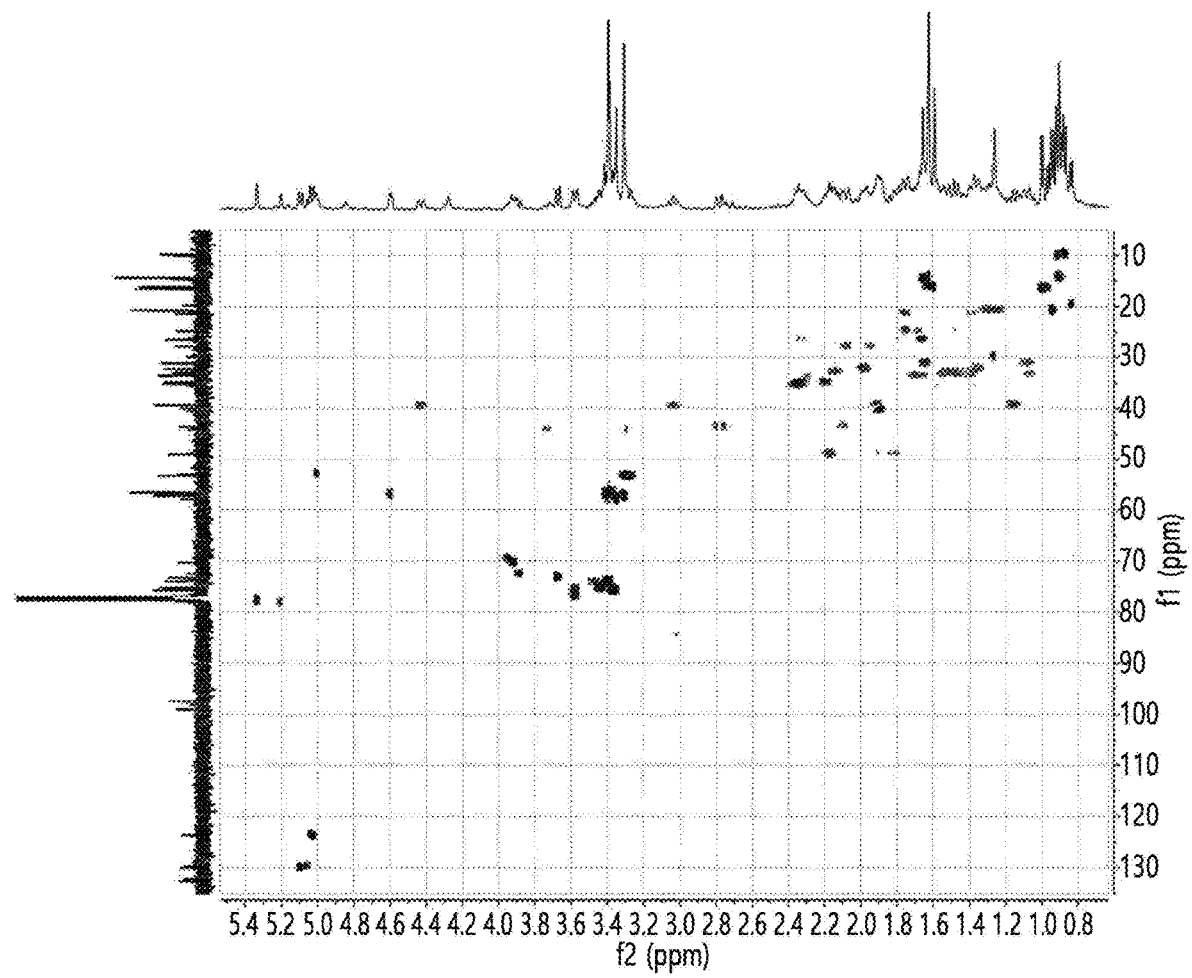
FIG. 17 shows nuclear magnetic resonance analysis (HSQC-NMR) results of 31-O-demethyl-36,37-dihydro-FK506.
Figure 18:
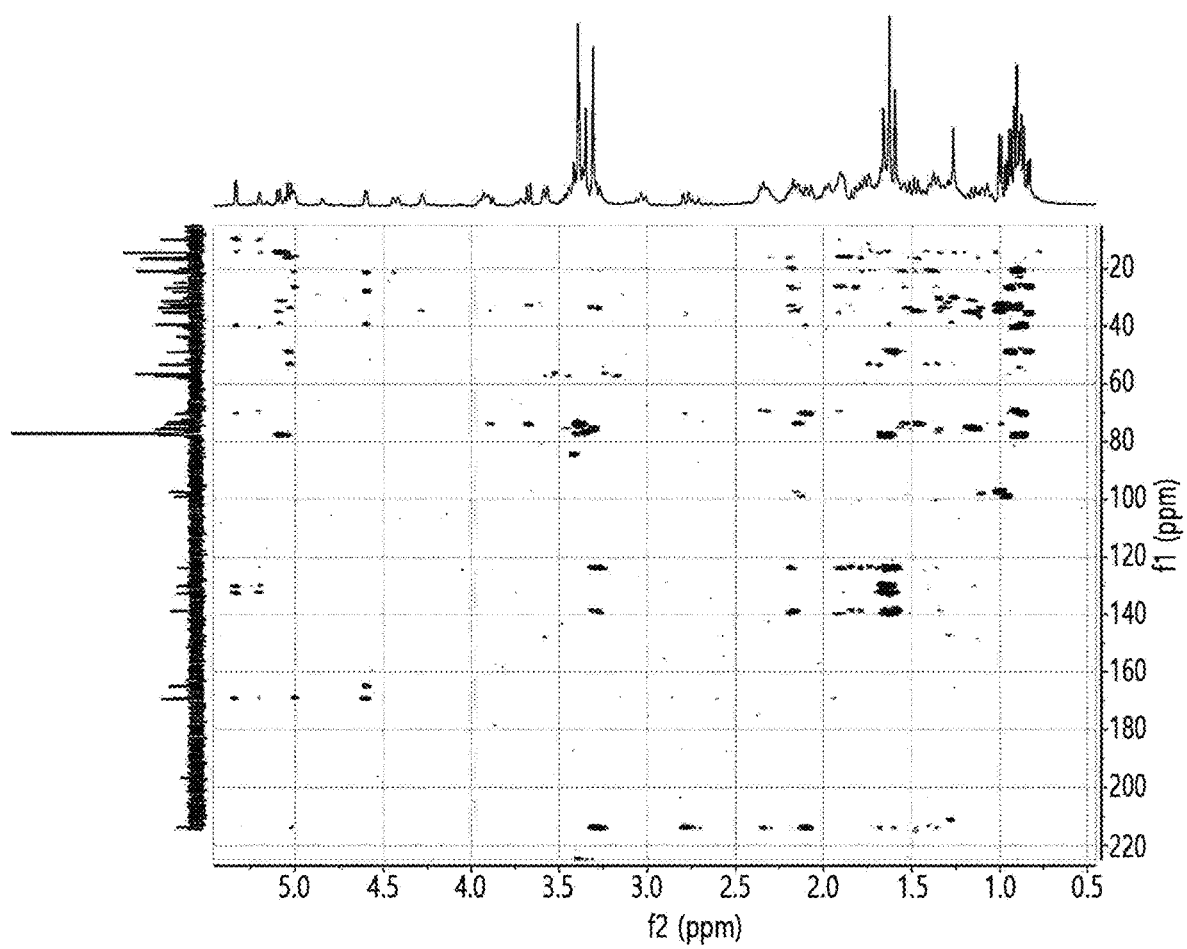
FIG. 18 shows nuclear magnetic resonance analysis (HMBC-NMR) results of 31-O-demethyl-36,37-dihydro-FK506.
Figure 19:
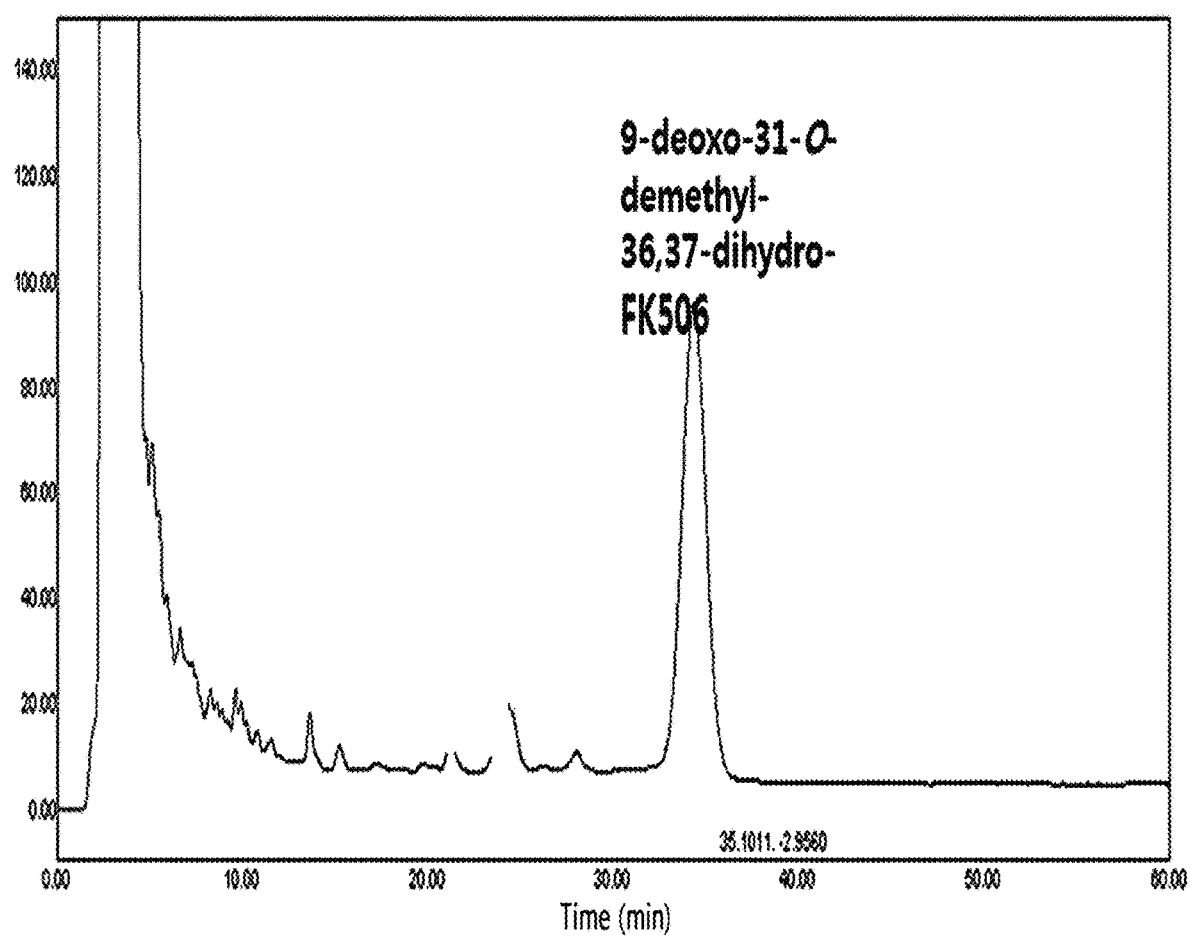
FIG. 19 shows high-performance liquid chromatography analysis results of 9-deoxo-31-O-demethyl-36,37-dihydro-FK506.
Figure 20:
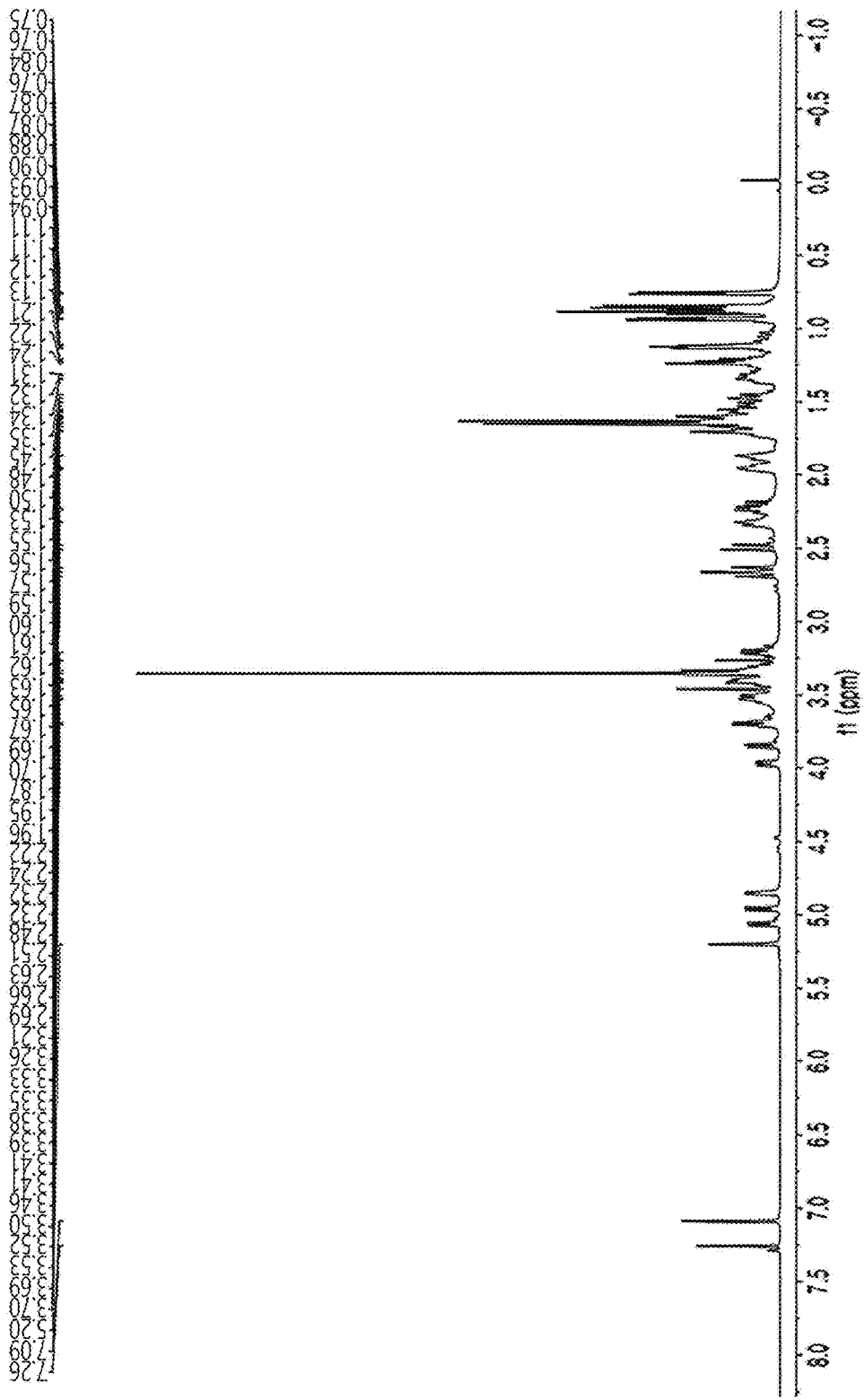
FIG. 20 shows nuclear magnetic resonance analysis ($^1$H-NMR) results of 9-deoxo-31-O-demethyl-36,37-dihydro-FK506.
Figure 21:
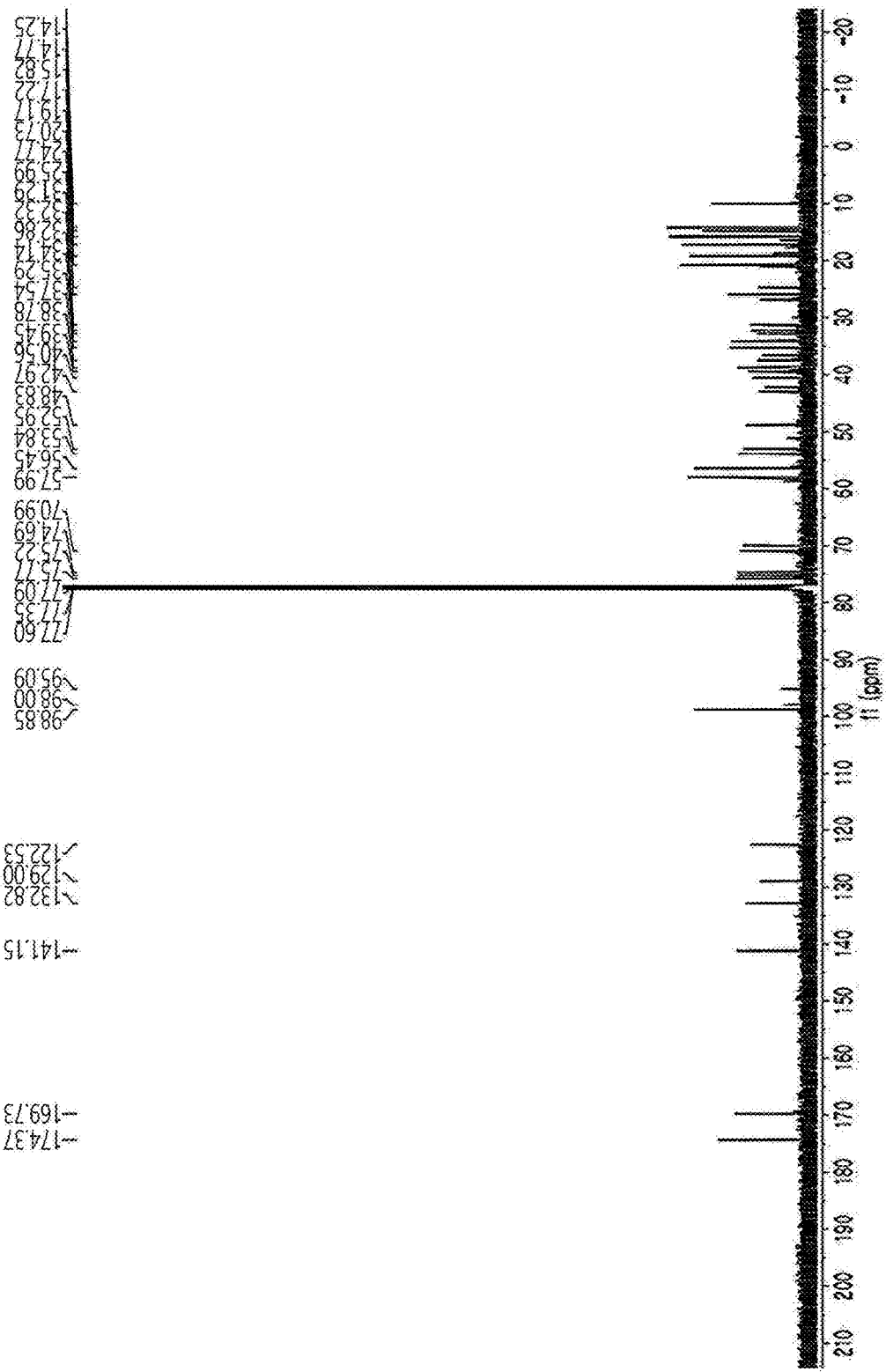
FIG. 21 shows nuclear magnetic resonance analysis ($^{13}$C-NMR) results of 9-deoxo-31-O-demethyl-36,37-dihydro-FK506.
Figure 22:
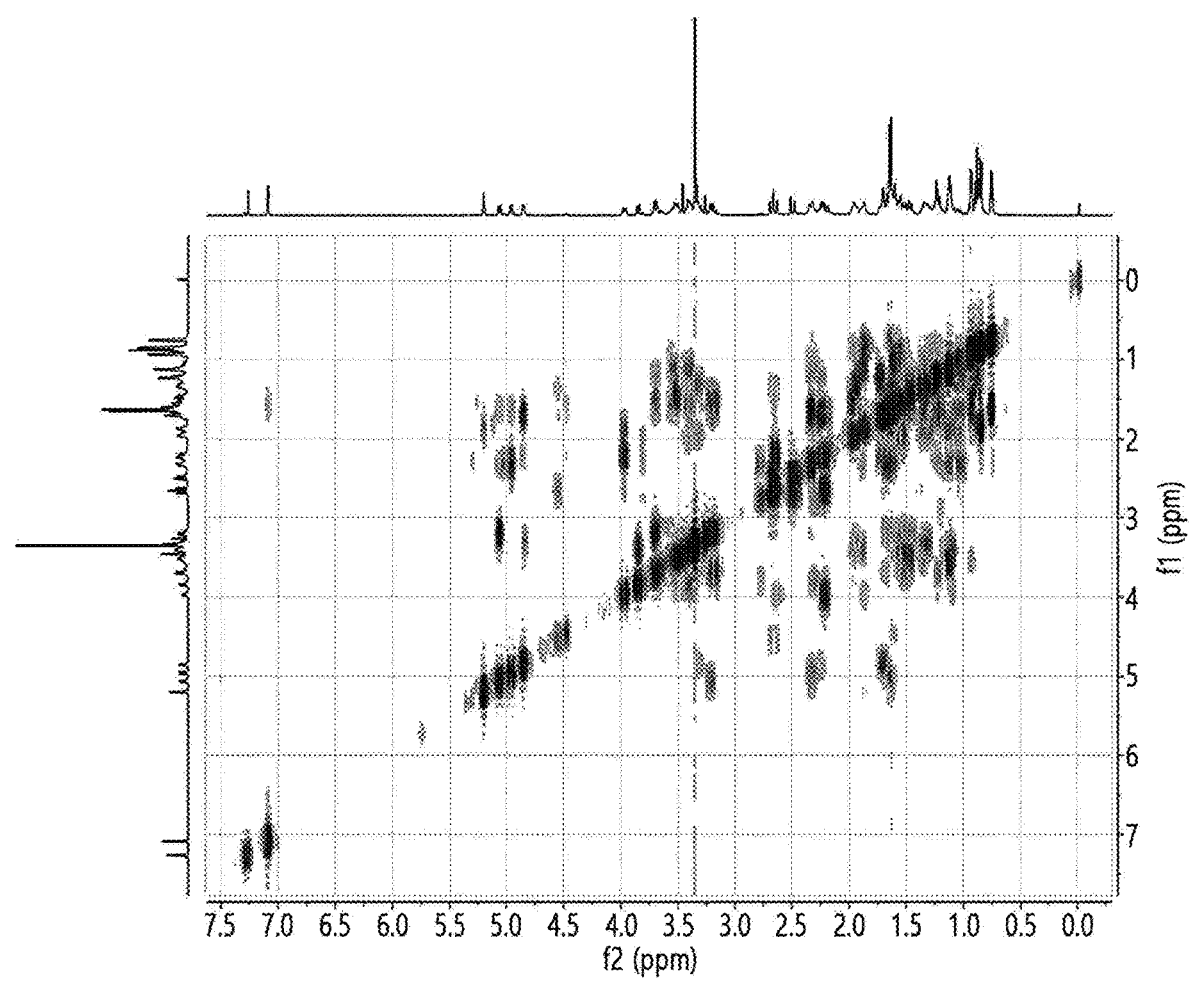
FIG. 22 shows nuclear magnetic resonance analysis (COSY-NMR) results of 9-deoxo-31-O-demethyl-36,37-dihydro-FK506.
Figure 23:
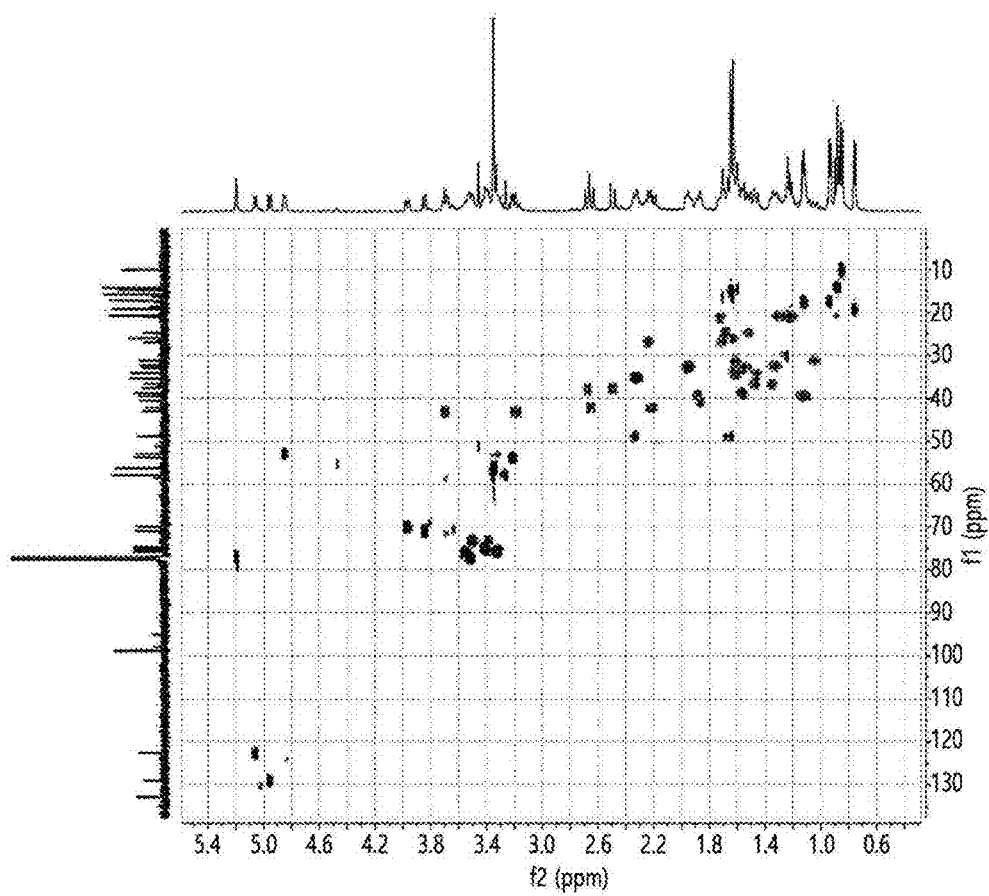
FIG. 23 shows nuclear magnetic resonance analysis (HSQC-NMR) results of 9-deoxo-31-O-demethyl-36,37-dihydro-FK506.
Figure 24:
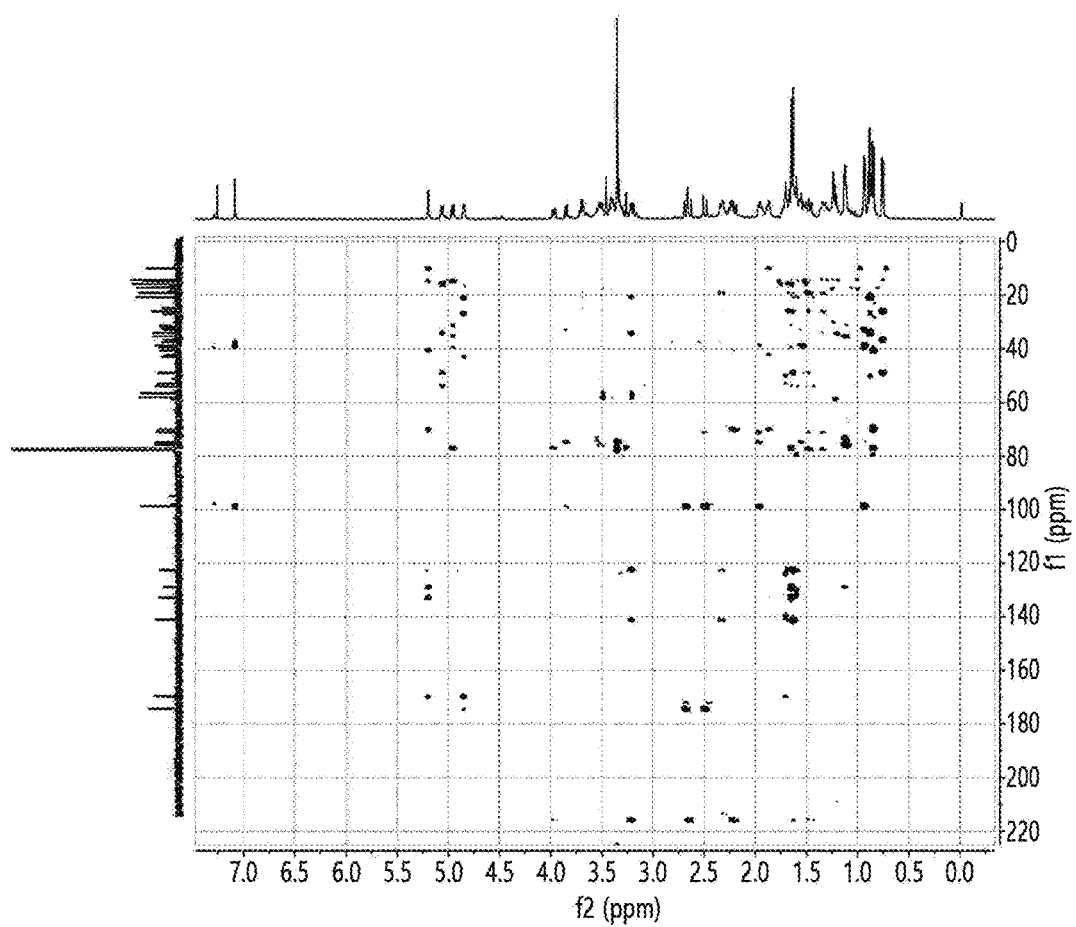
FIG. 24 shows nuclear magnetic resonance analysis (HMBC-NMR) results of 9-deoxo-31-O-demethyl-36,37-dihydro-FK506.
Figure 25:
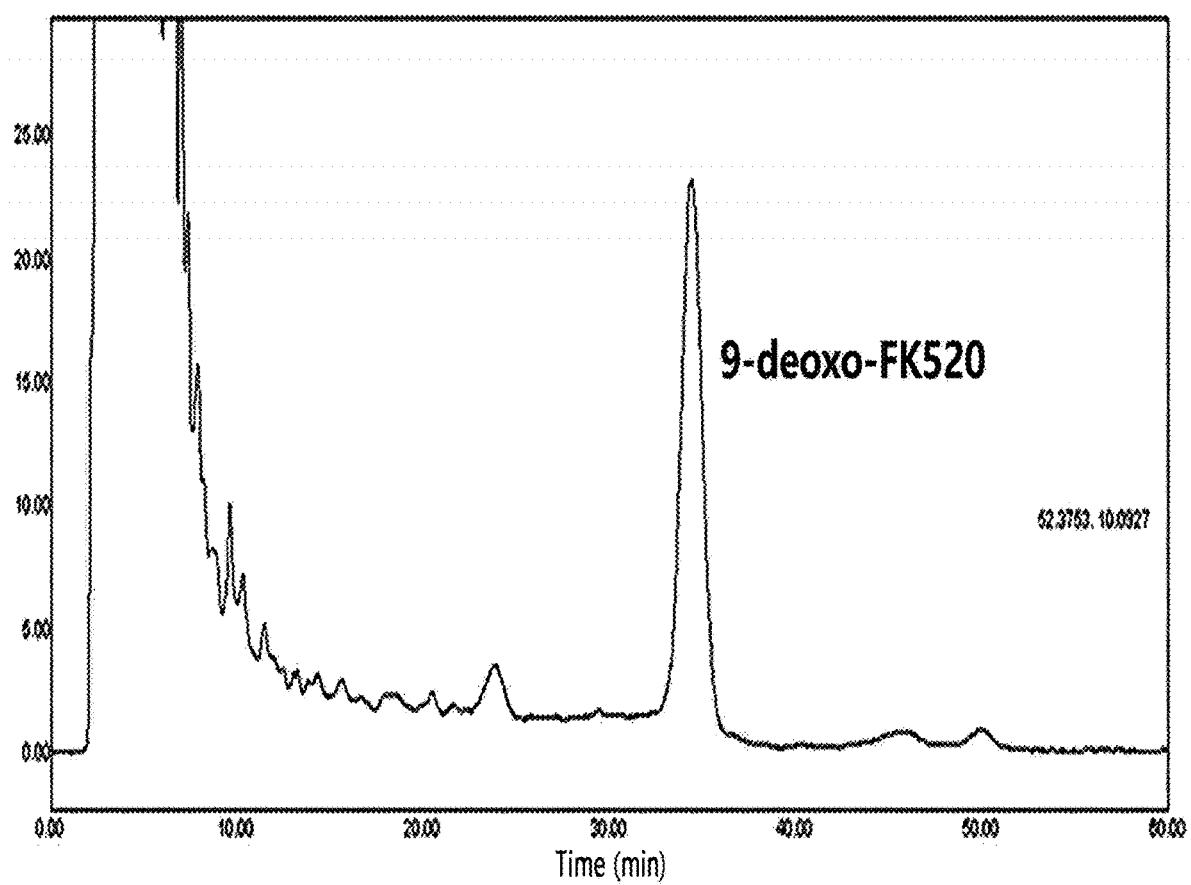
FIG. 25 shows high-performance liquid chromatography analysis results of 9-deoxo-FK520.
Figure 26:
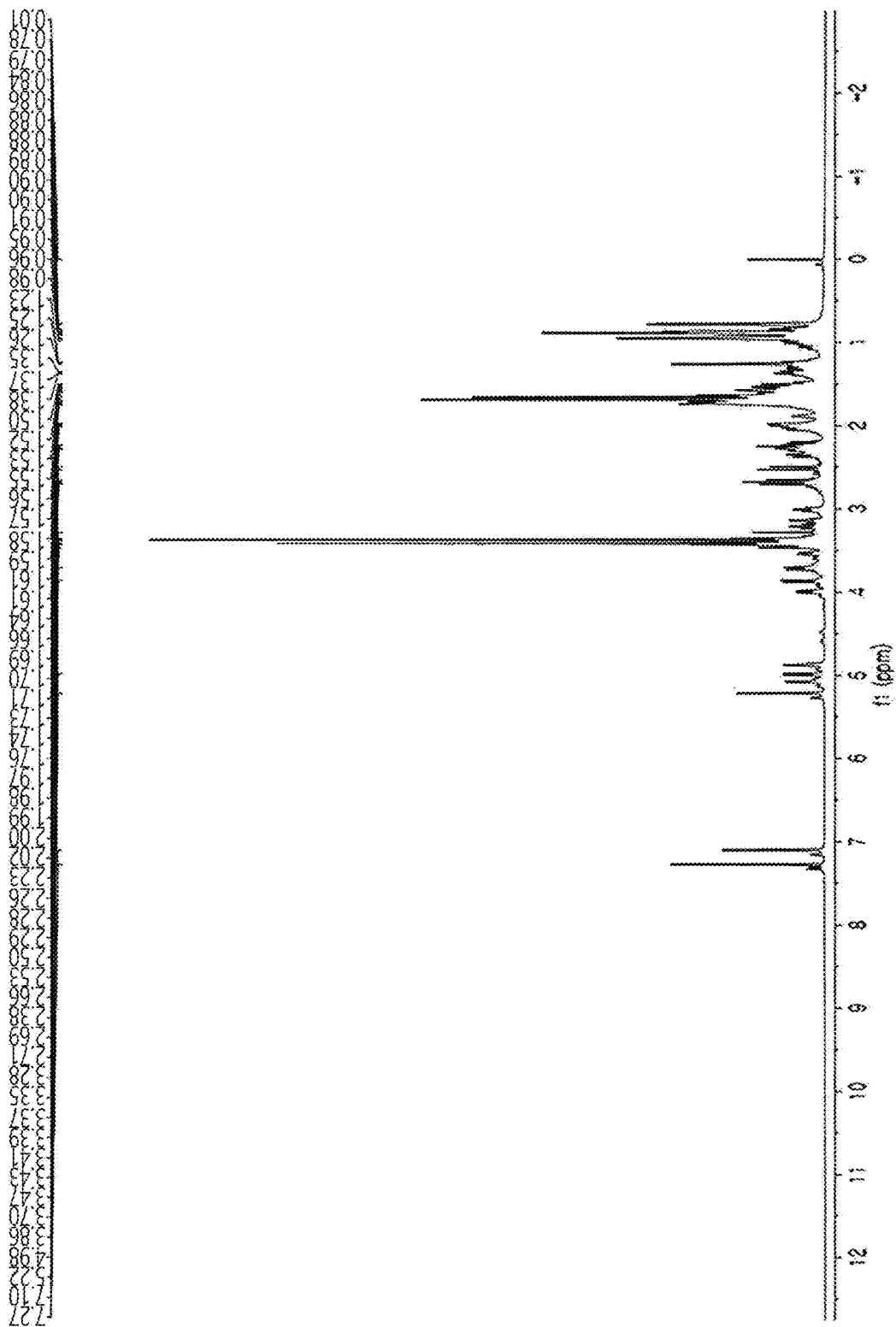
FIG. 26 shows nuclear magnetic resonance analysis ($^1$H-NMR) results of 9-deoxo-FK520.
Figure 27:
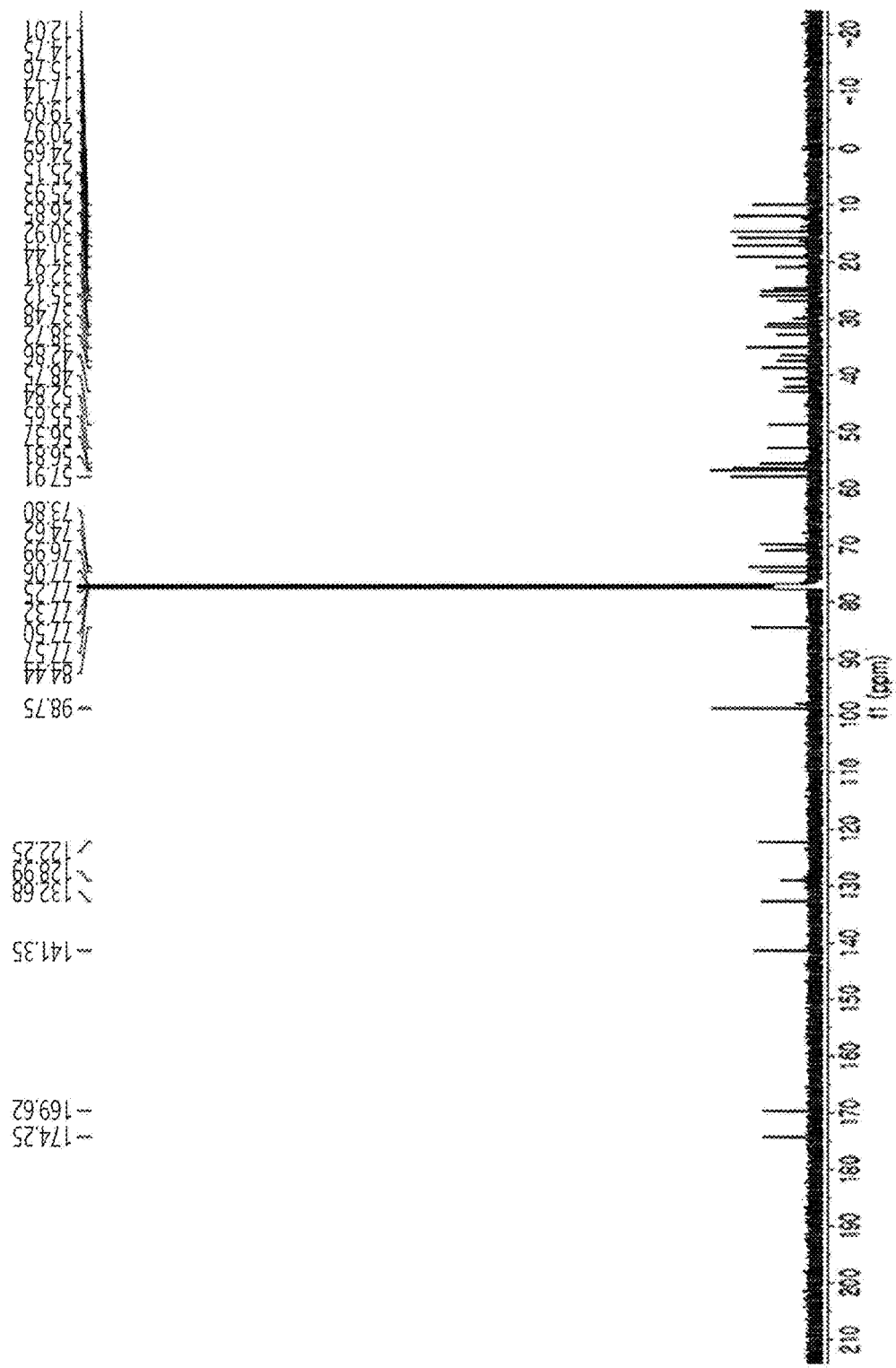
FIG. 27 shows nuclear magnetic resonance analysis ($^{13}$C-NMR) results of 9-deoxo-FK520.
Figure 28:
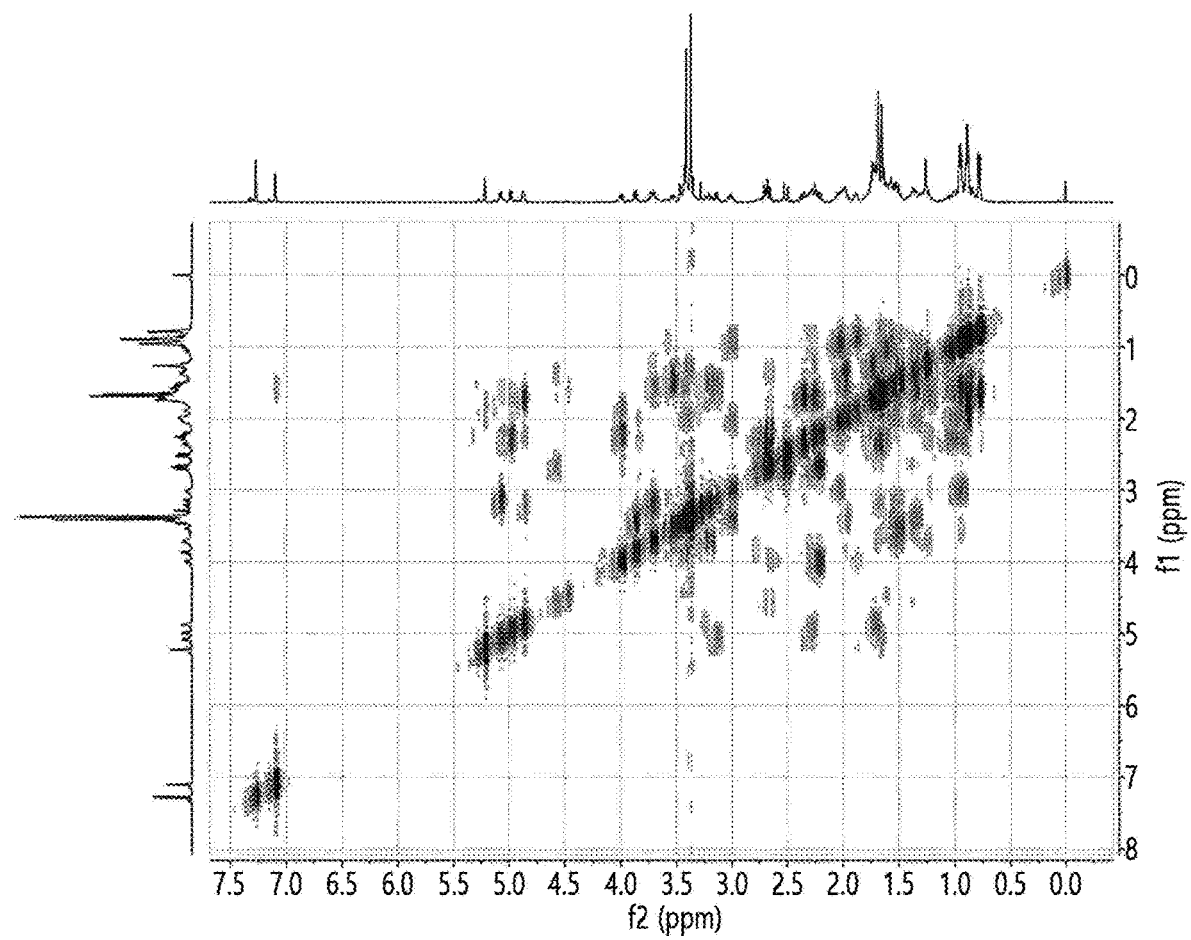
FIG. 28 shows nuclear magnetic resonance analysis (COSY-NMR) results of 9-deoxo-FK520.
Figure 29:
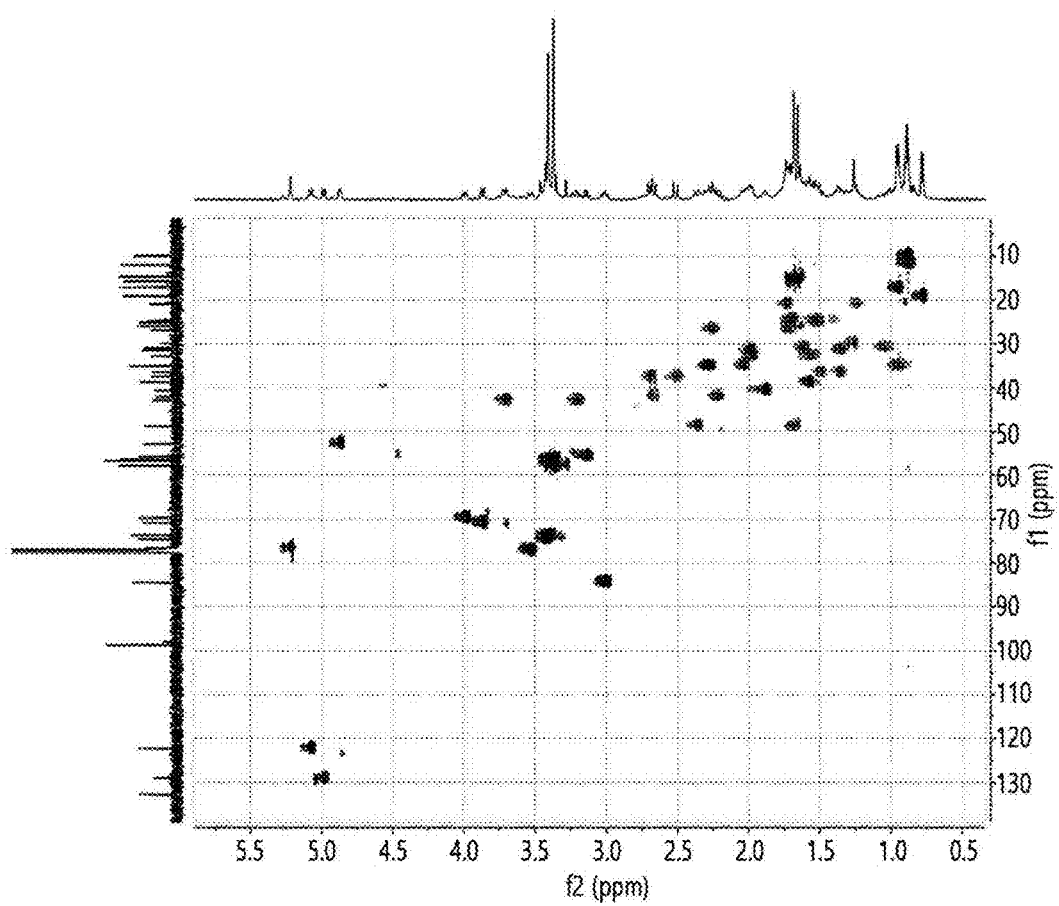
FIG. 29 shows nuclear magnetic resonance analysis (HSQC-NMR) results of 9-deoxo-FK520.
Figure 30:
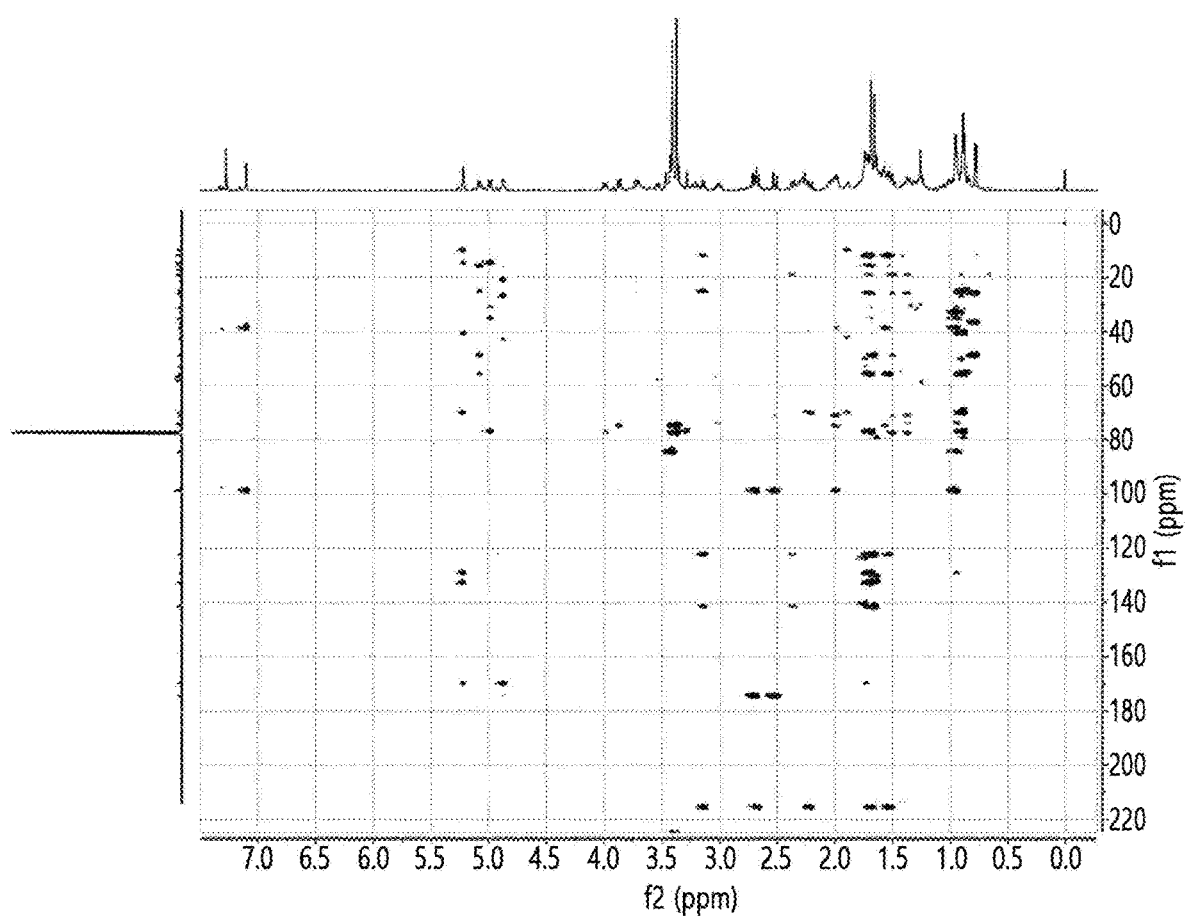
FIG. 30 shows nuclear magnetic resonance analysis (HMBC-NMR) results of 9-deoxo-FK520.
Figure 31:
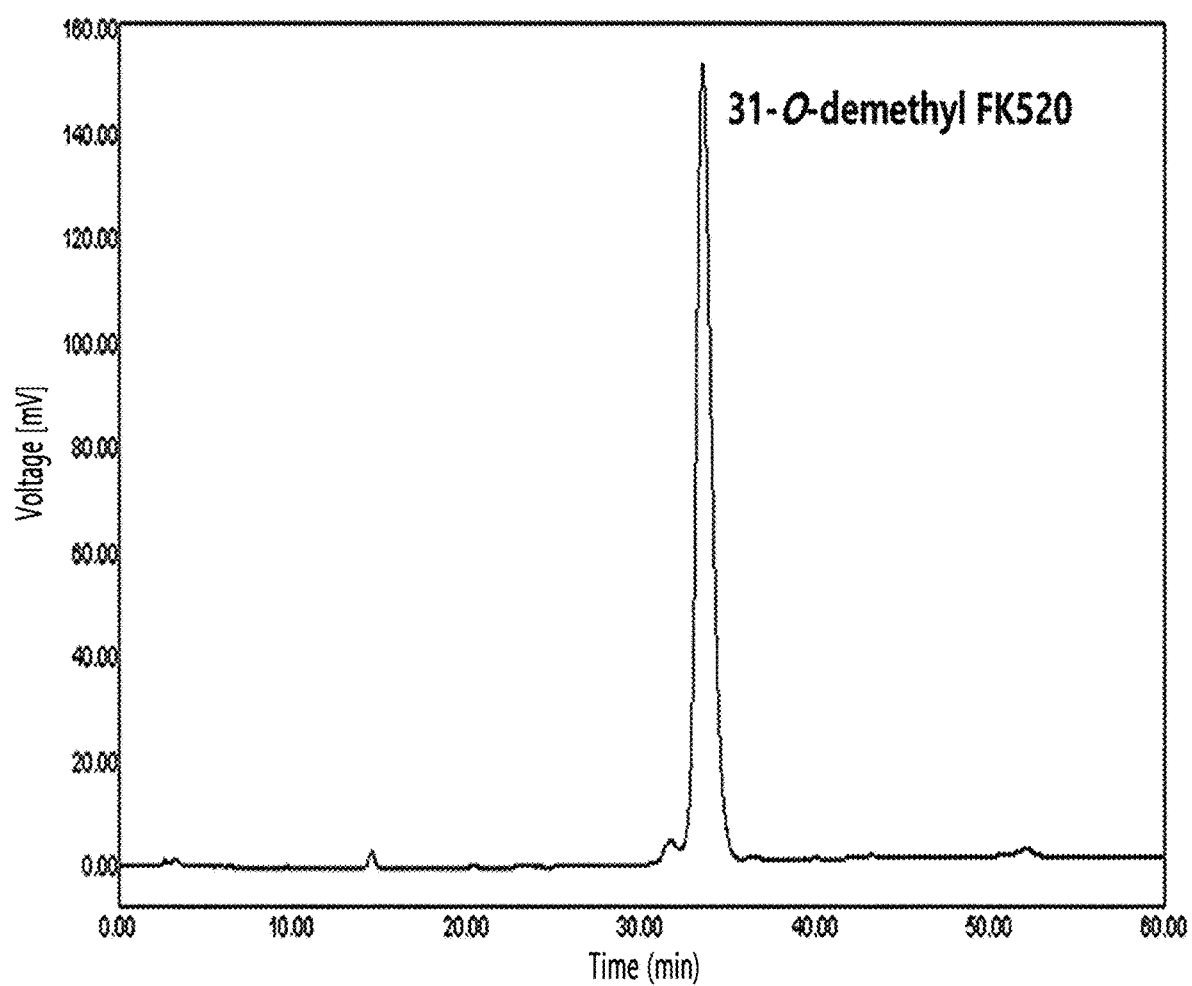
FIG. 31 shows high-performance liquid chromatography analysis results of 31-O-demethyl-FK520.
Figure 32:
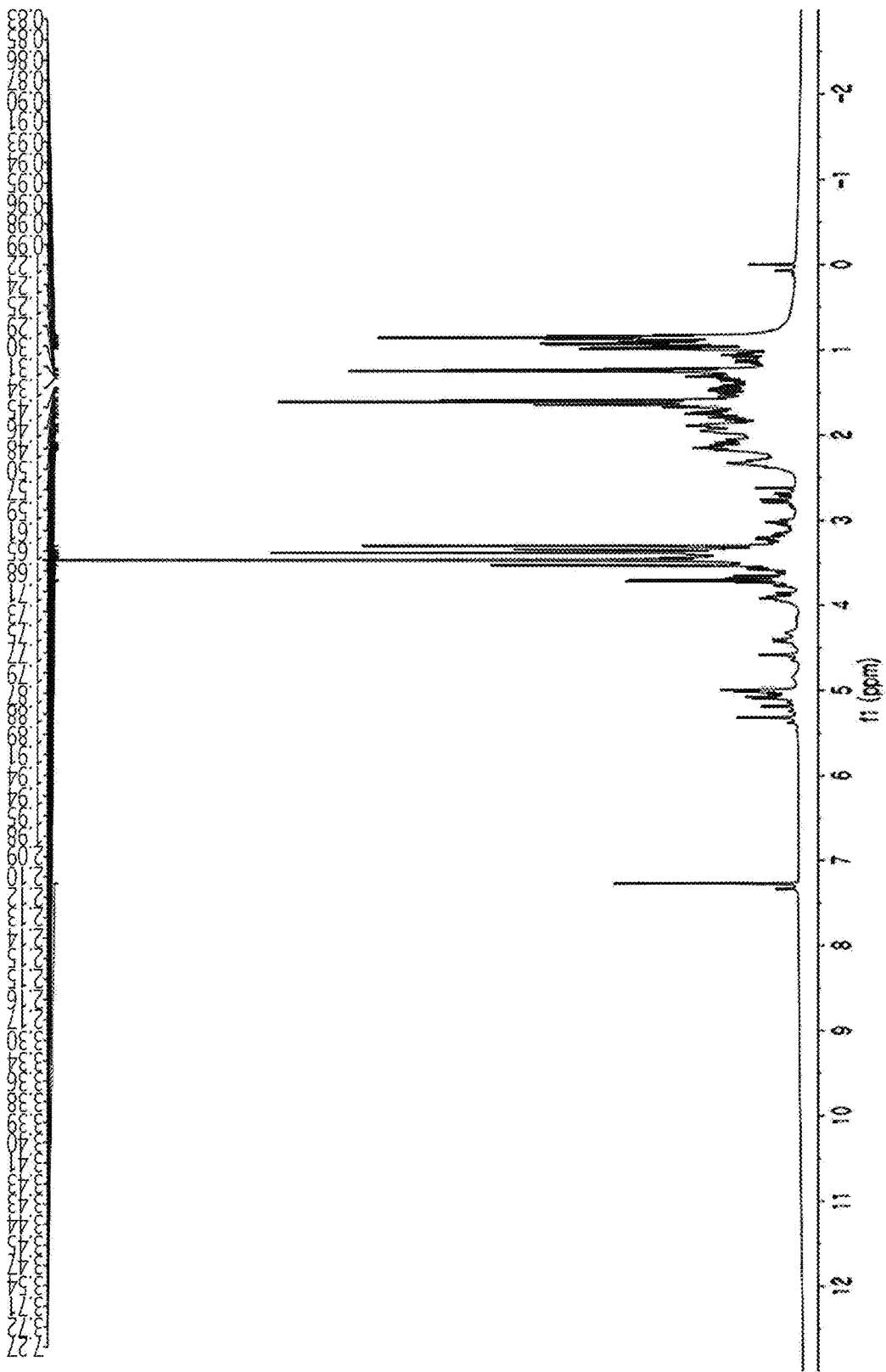
FIG. 32 shows nuclear magnetic resonance analysis ($^1$H-NMR) results of 31-O-demethyl-FK520.
Figure 33:
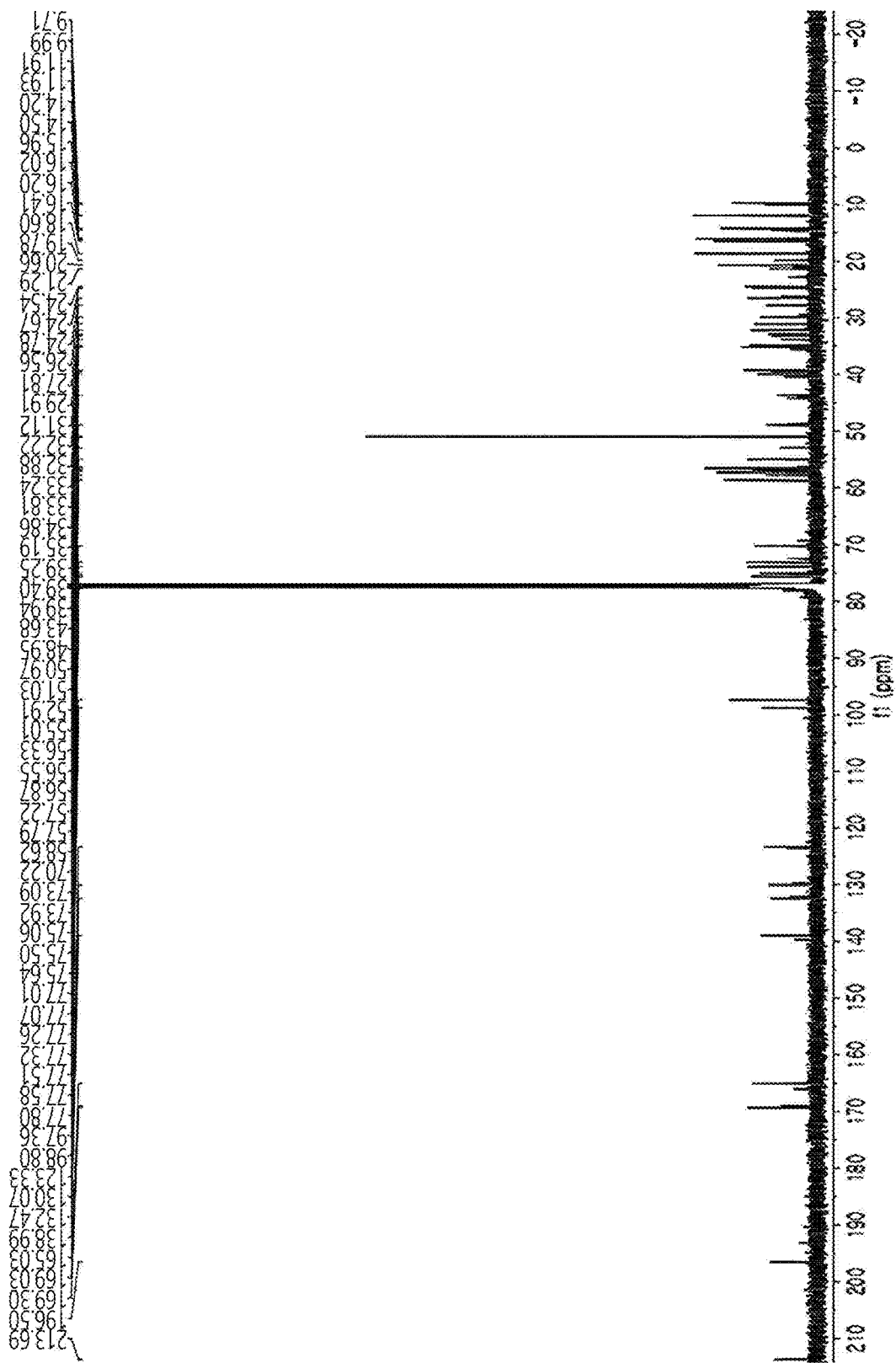
FIG. 33 shows nuclear magnetic resonance analysis ($^{13}$C-NMR) results of 31-O-demethyl-FK520.
Figure 34:
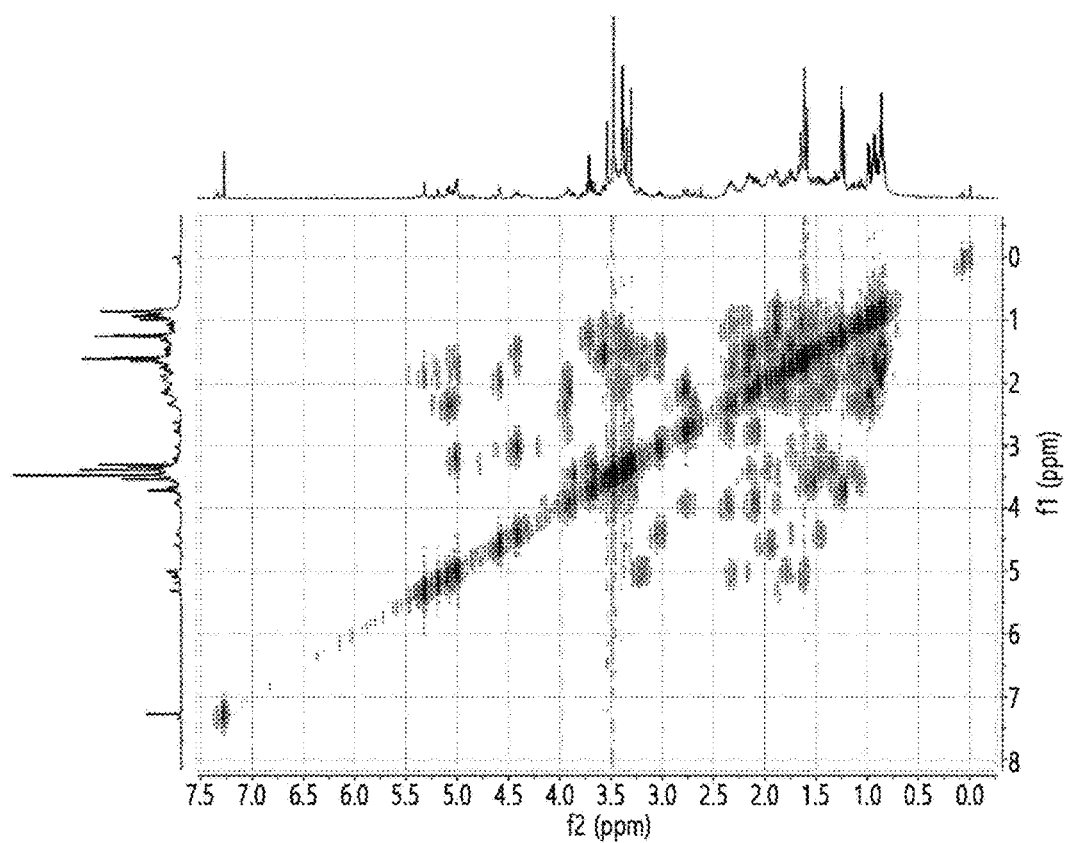
FIG. 34 shows nuclear magnetic resonance analysis (COSY-NMR) results of 31-O-demethyl-FK520.
Figure 35:
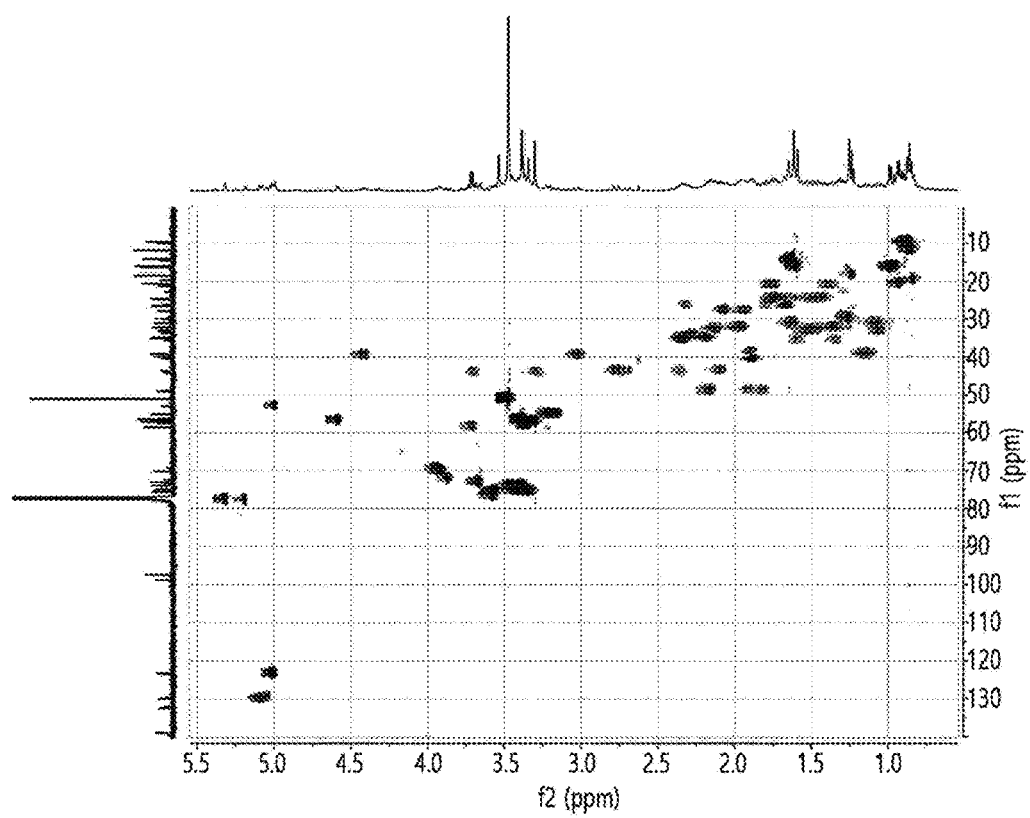
FIG. 35 shows nuclear magnetic resonance analysis (HSQC-NMR) results of 31-O-demethyl-FK520.
Figure 36:
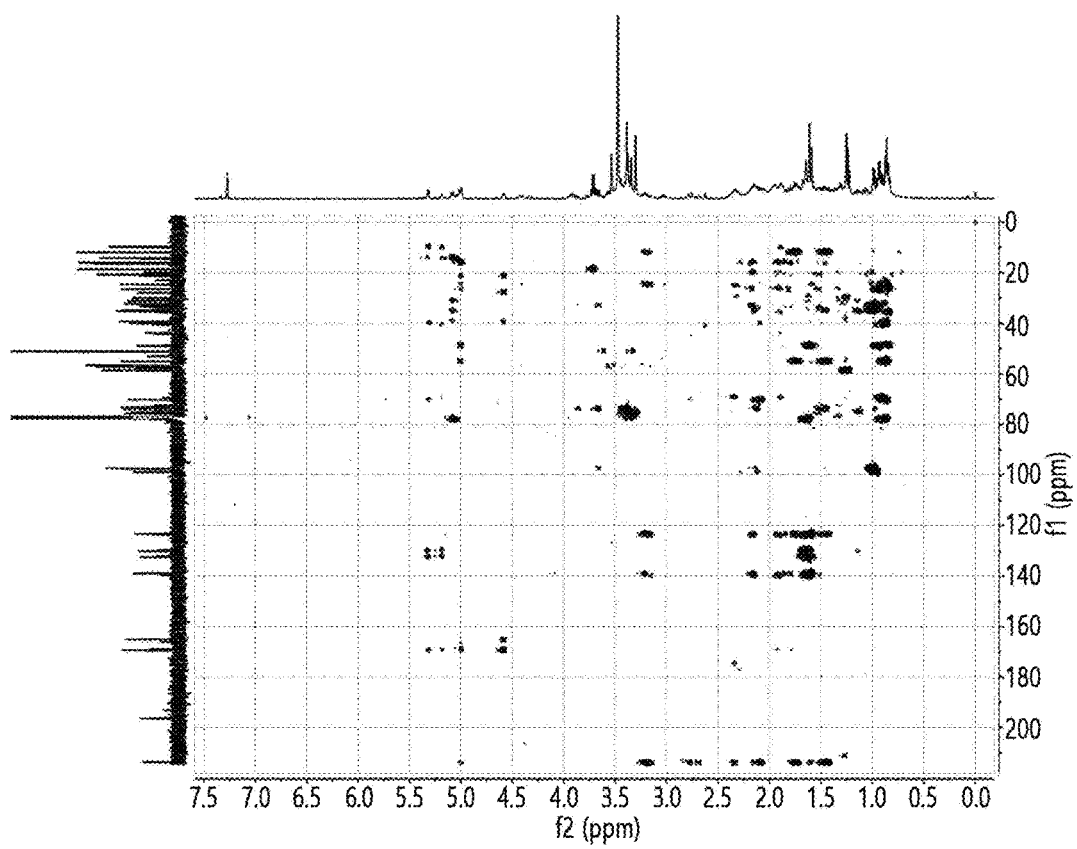
FIG. 36 shows nuclear magnetic resonance analysis (HMBC-NMR) results of 31-O-demethyl-FK520.
Figure 37:
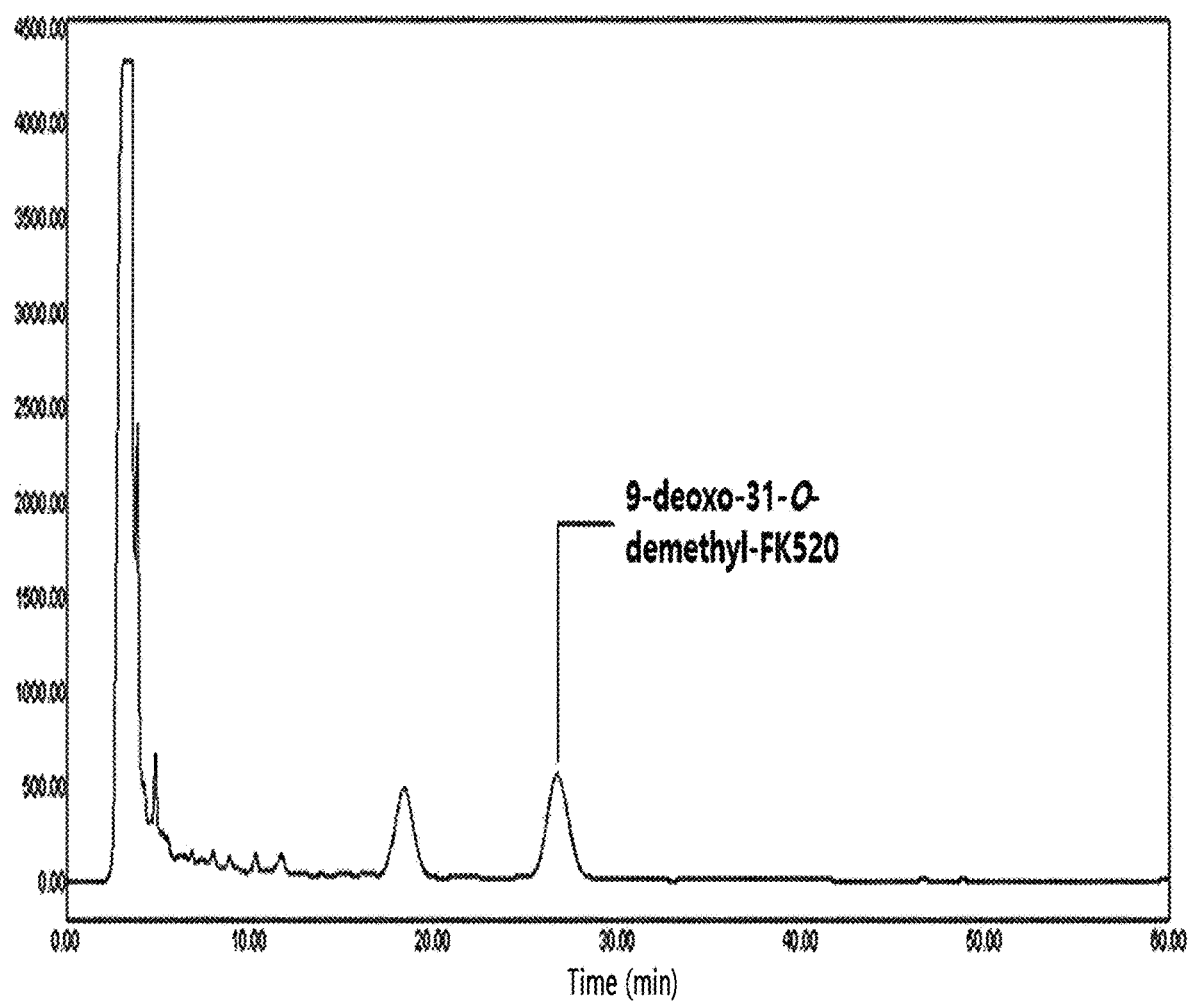
FIG. 37 shows high-performance liquid chromatography analysis results of 9-deoxo-31-O-demethyl-FK520.
Figure 38:
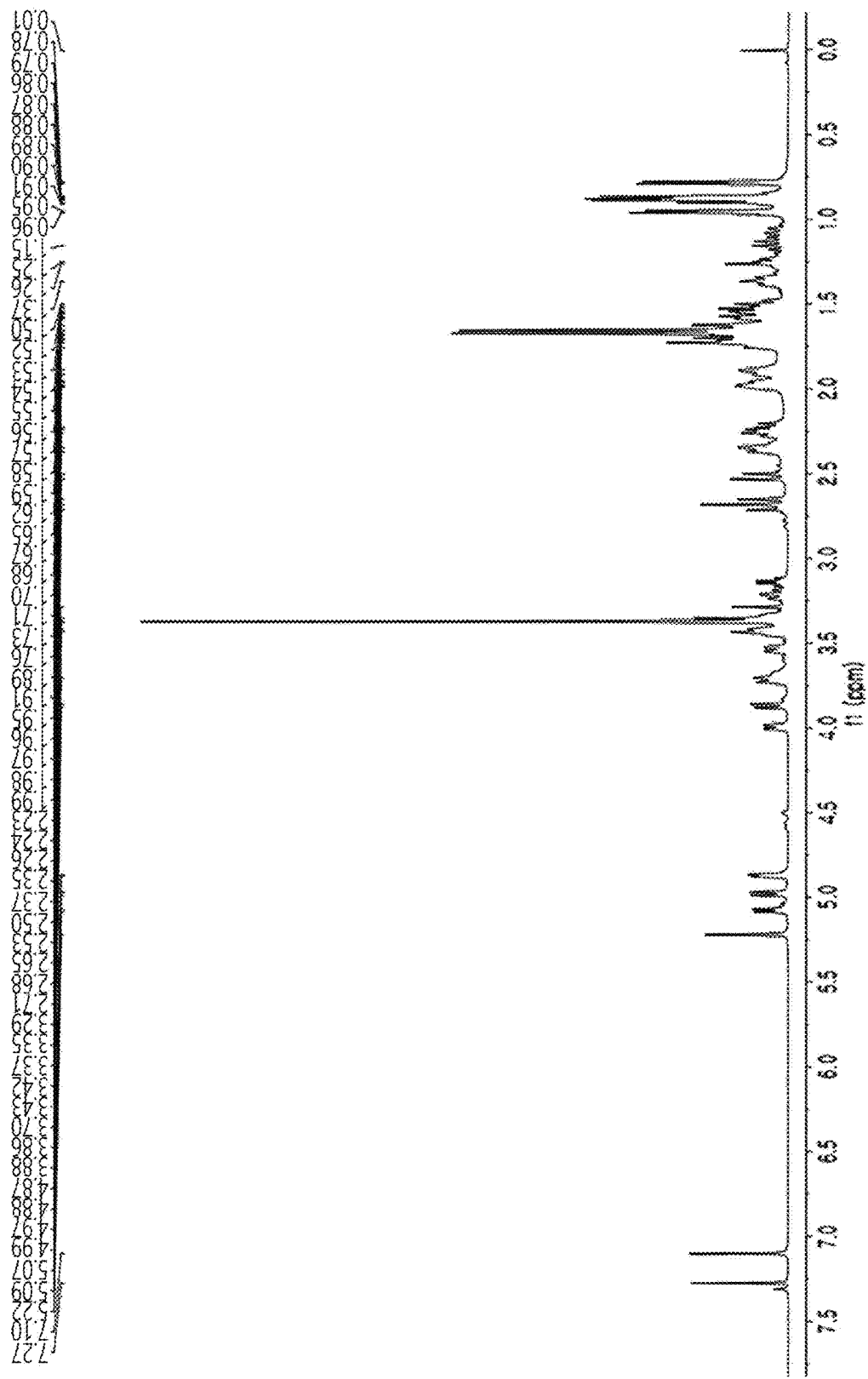
FIG. 38 shows nuclear magnetic resonance analysis ($^1$H-NMR) results of 9-deoxo-31-O-demethyl-FK520.
Figure 39:
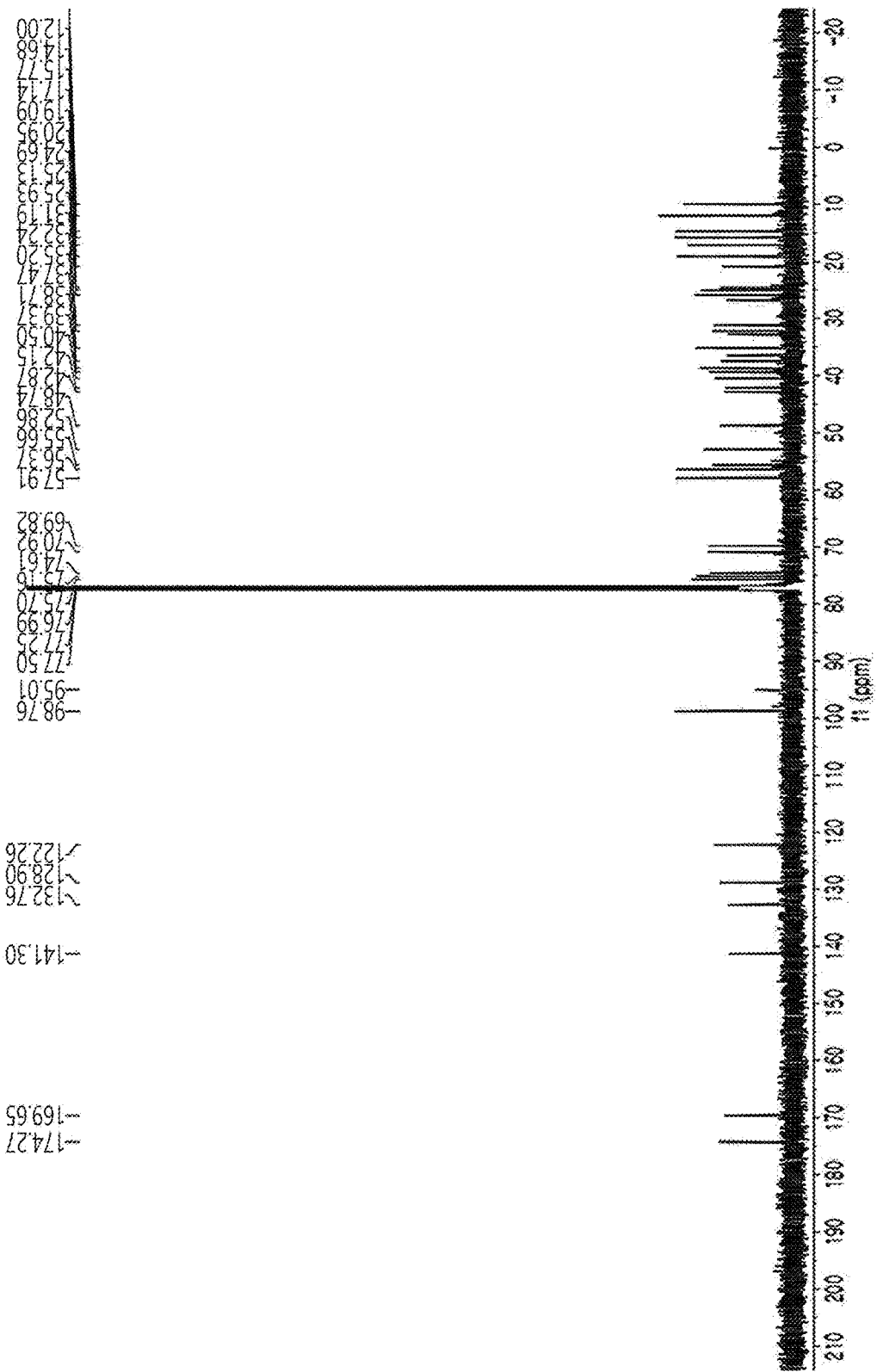
FIG. 39 shows nuclear magnetic resonance analysis ($^{13}$C-NMR) results of 9-deoxo-31-O-demethyl-FK520.
Figure 40:
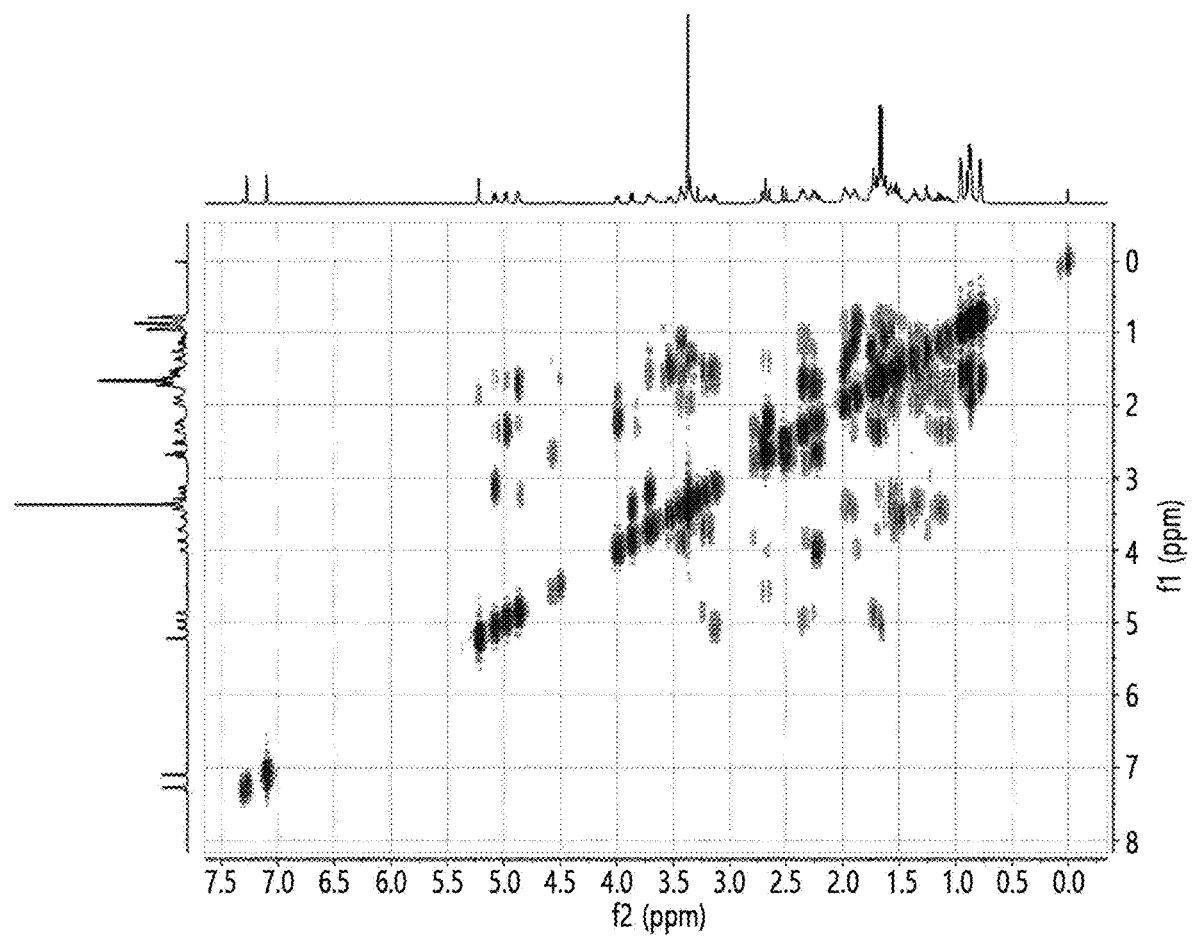
FIG. 40 shows nuclear magnetic resonance analysis (COSY-NMR) results of 9-deoxo-31-O-demethyl-FK520.
Figure 41:
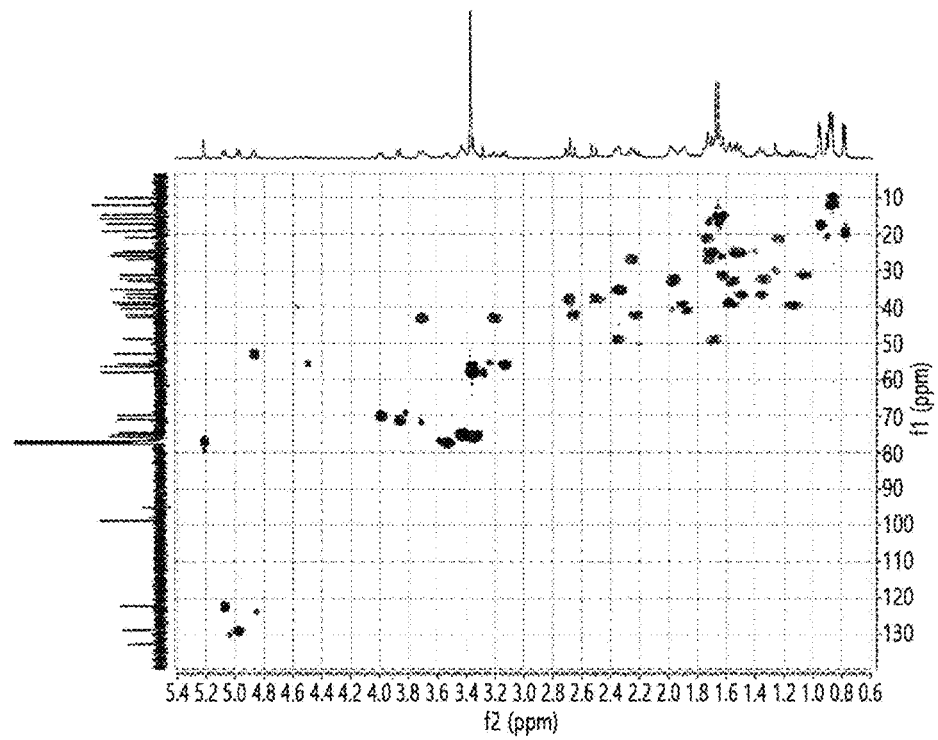
FIG. 41 shows nuclear magnetic resonance analysis (HSQC-NMR) results of 9-deoxo-31-O-demethyl-FK520.
Figure 42:
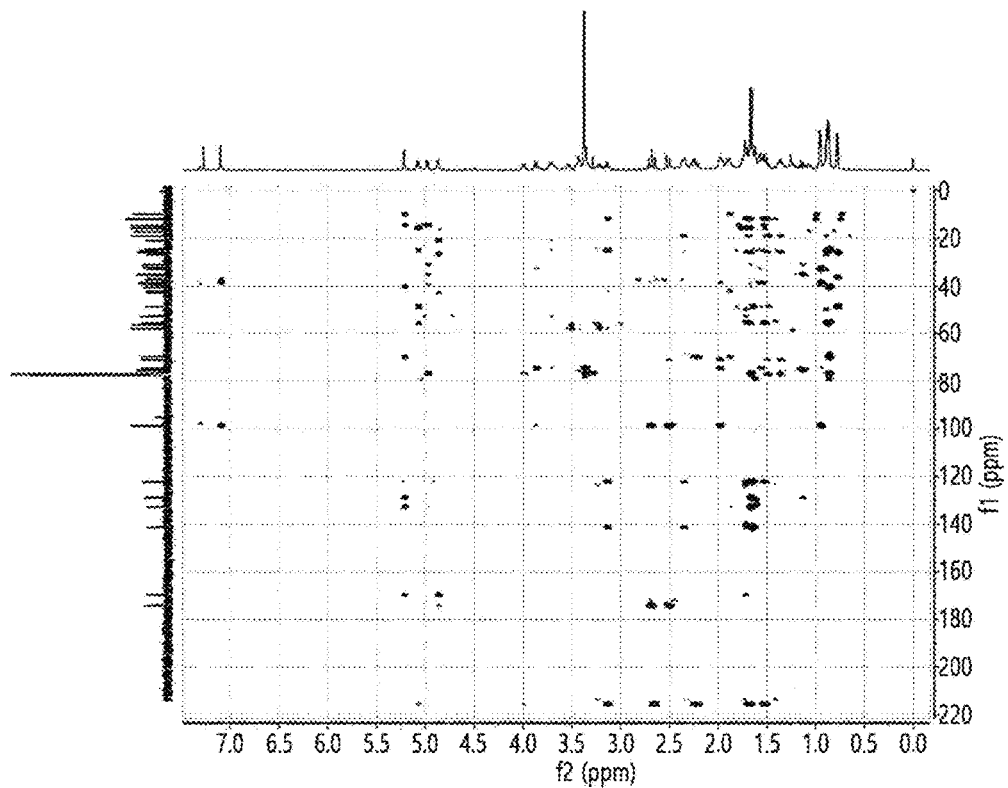
FIG. 42 shows nuclear magnetic resonance analysis (HMBC-NMR) results of 9-deoxo-31-O-demethyl-FK520.
Figure 43:
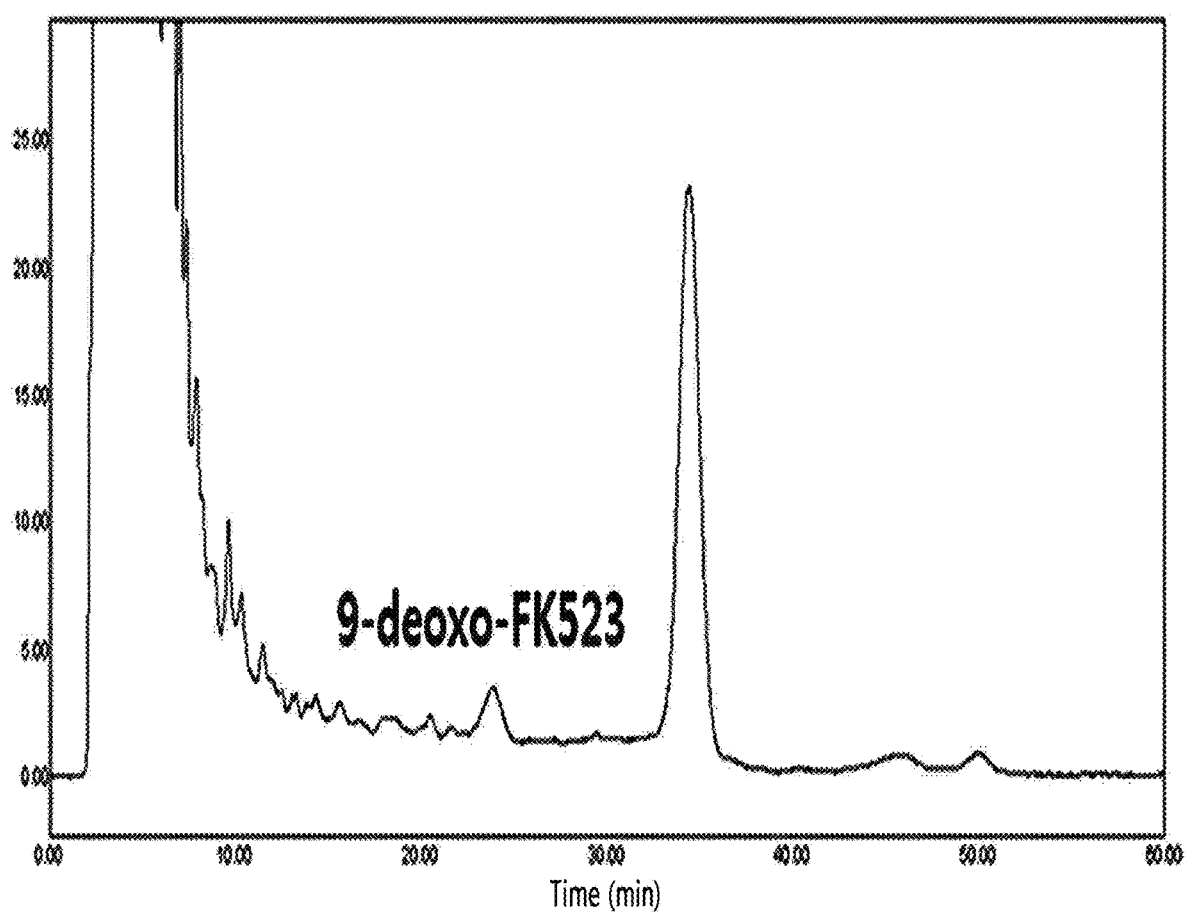
FIG. 43 shows high-performance liquid chromatography analysis results of 9-deoxo-FK523.
Figure 44:
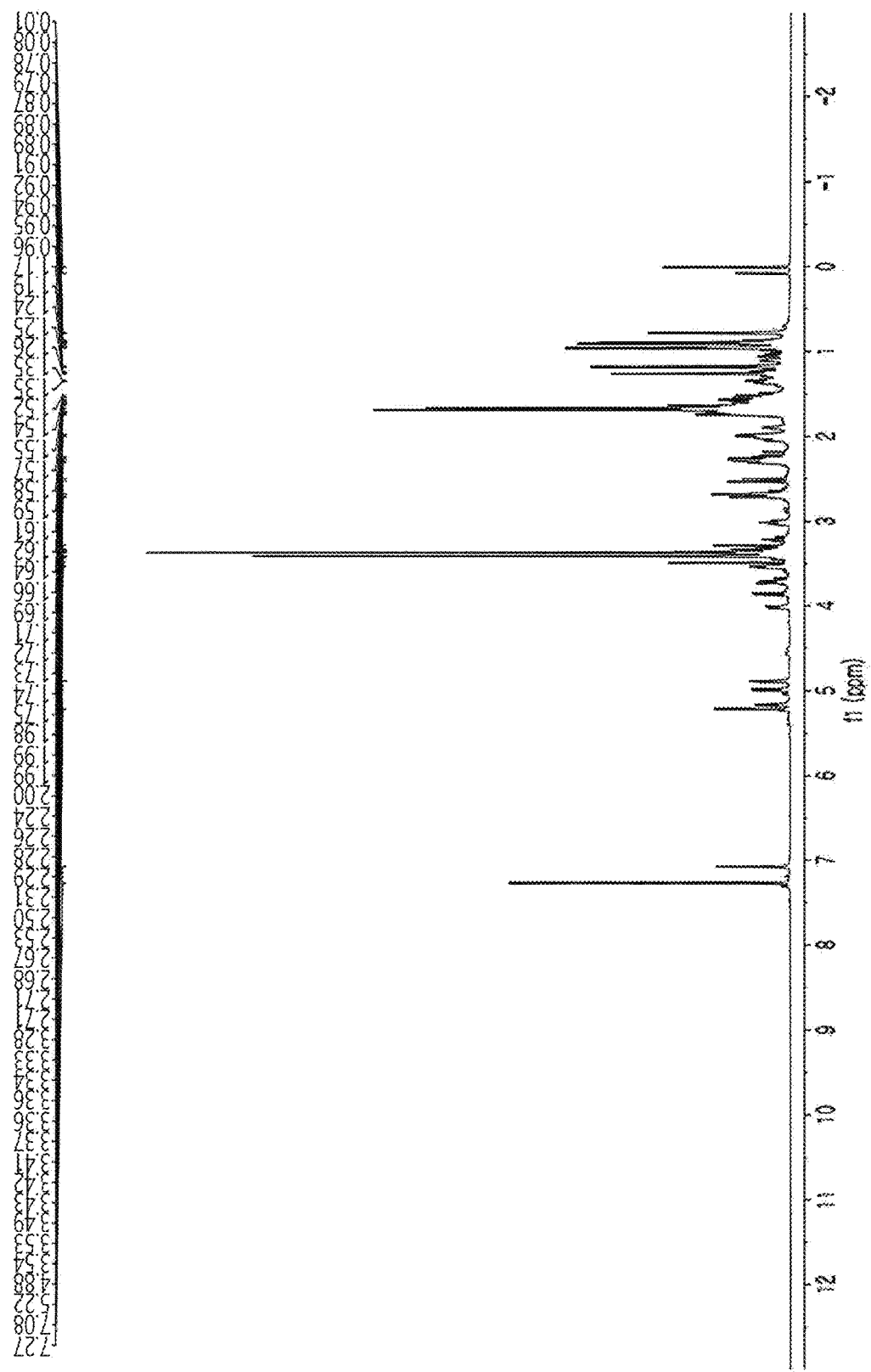
FIG. 44 shows nuclear magnetic resonance analysis ($^1$H-NMR) results of 9-deoxo-FK523.
Figure 45:
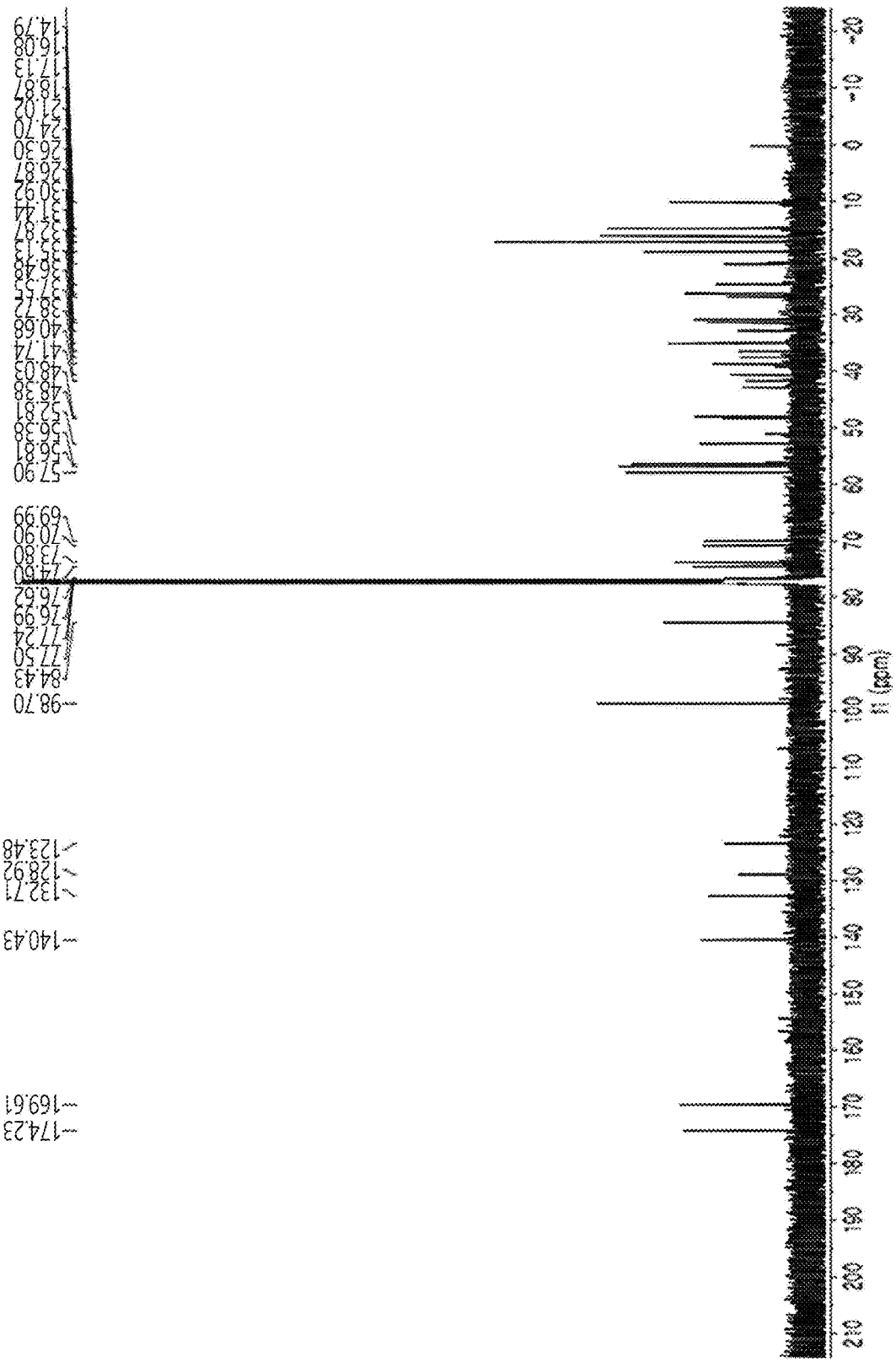
FIG. 45 shows nuclear magnetic resonance analysis ($^{13}$C-NMR) results of 9-deoxo-FK523.
Figure 46:
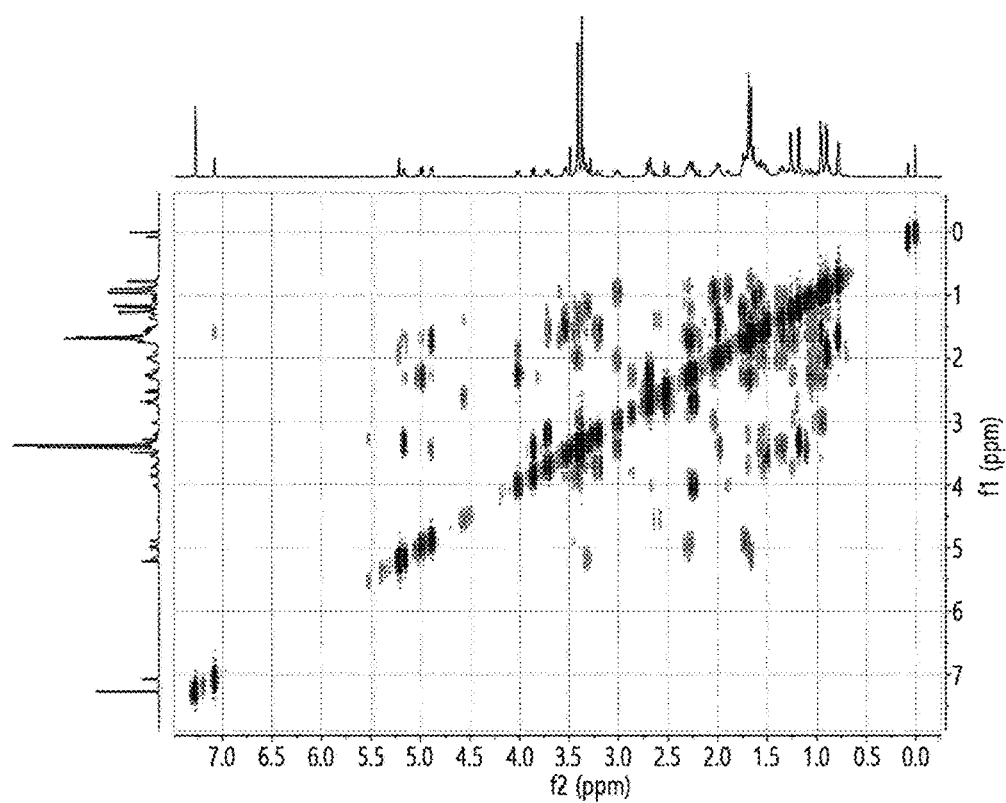
FIG. 46 shows nuclear magnetic resonance analysis (COSY-NMR) results of 9-deoxo-FK523.
Figure 47:
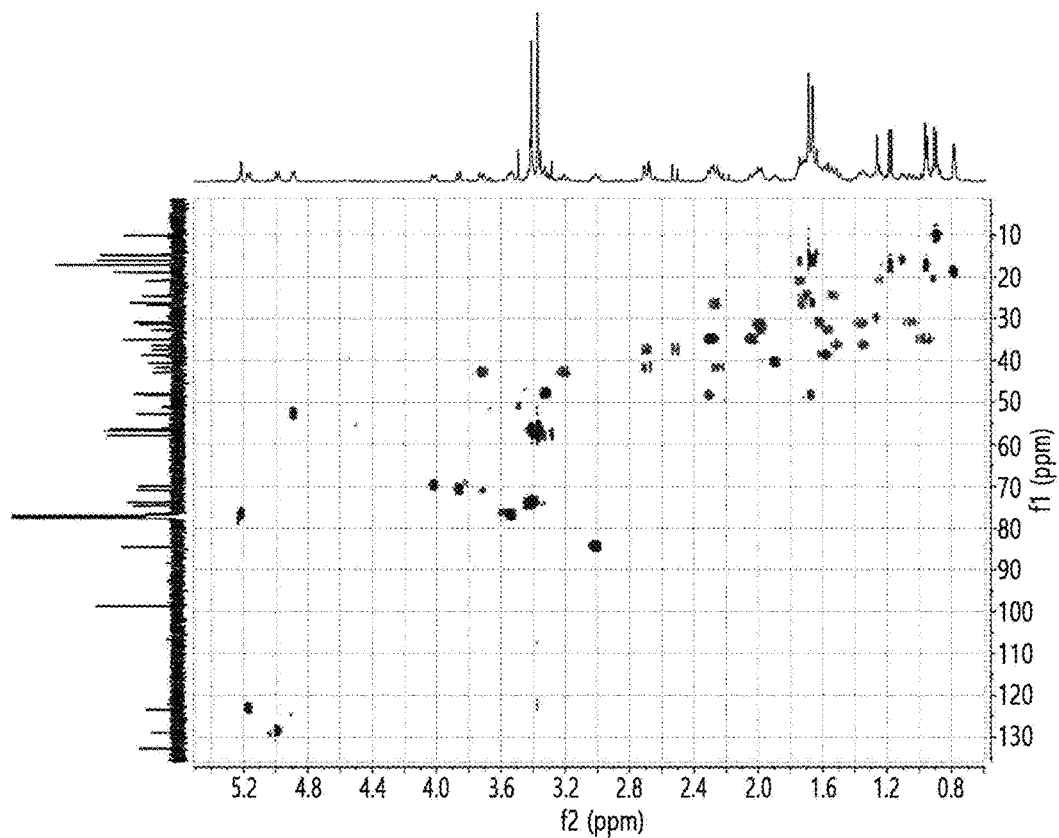
FIG. 47 shows nuclear magnetic resonance analysis (HSQC-NMR) results of 9-deoxo-FK523.
Figure 48:
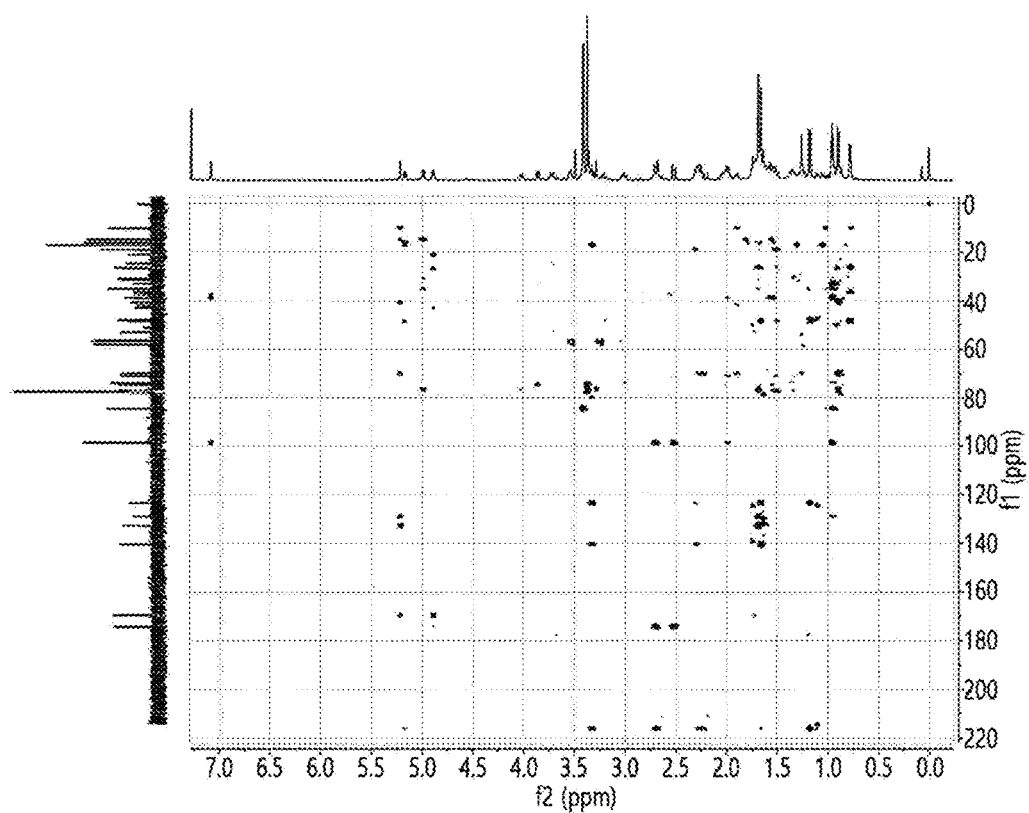
FIG. 48 shows nuclear magnetic resonance analysis (HMBC-NMR) results of 9-deoxo-FK523.
Figure 49:
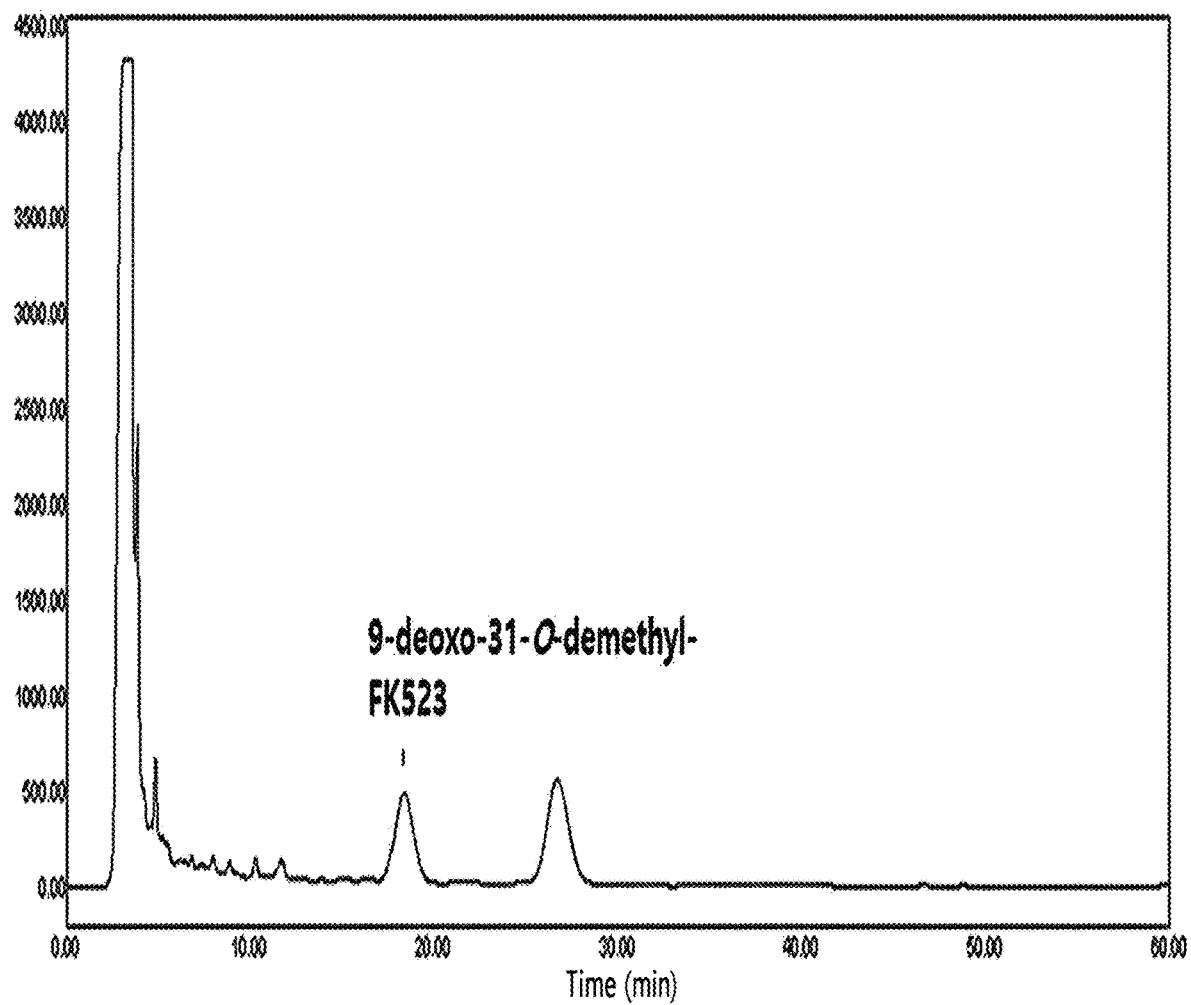
FIG. 49 shows high-performance liquid chromatography analysis results of 9-deoxo-31-O-demethyl-FK523.
Figure 50:
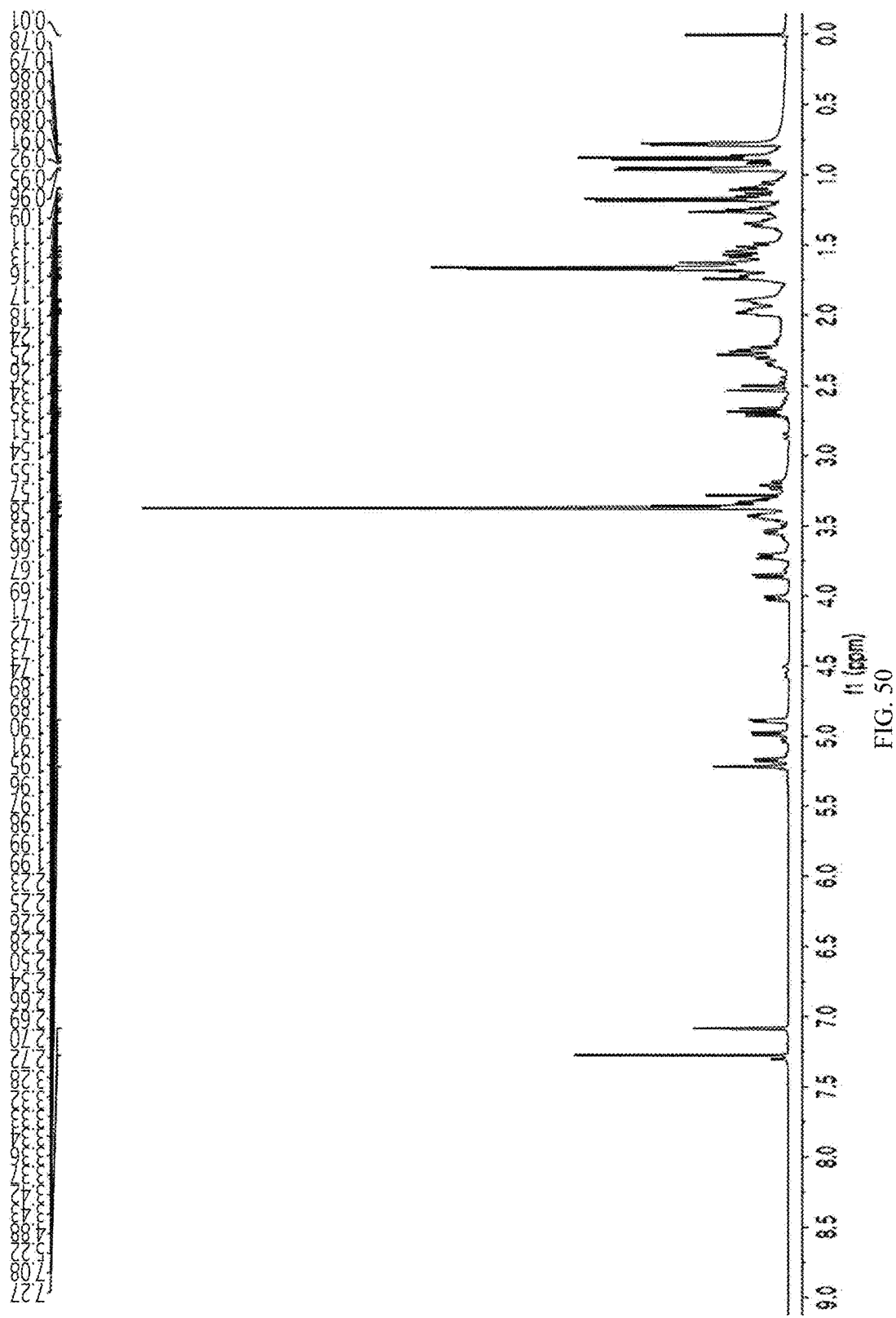
FIG. 50 shows nuclear magnetic resonance analysis ($^1$H-NMR) results of 9-deoxo-31-O-demethyl-FK523.
Figure 51:
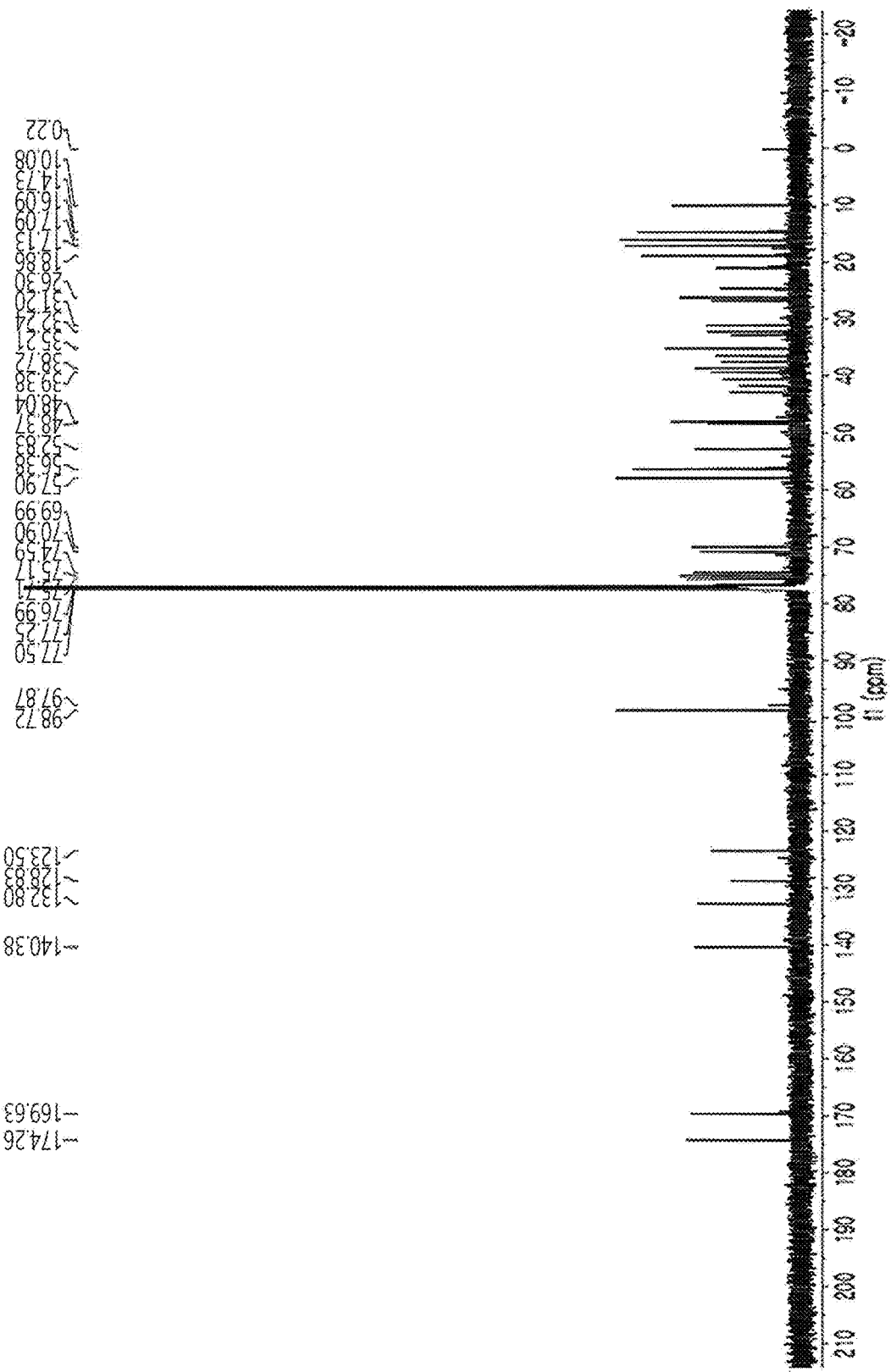
FIG. 51 shows nuclear magnetic resonance analysis ($^{13}$C-NMR) results of 9-deoxo-31-O-demethyl-FK523.
Figure 52:
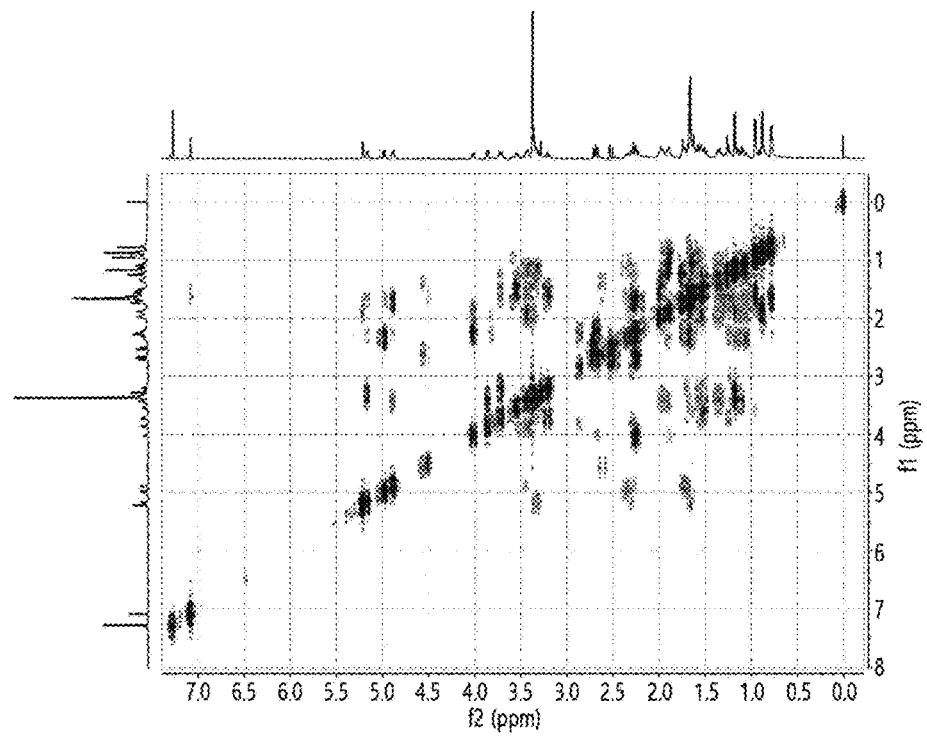
FIG. 52 shows nuclear magnetic resonance analysis (COSY-NMR) results of 9-deoxo-31-O-demethyl-FK523.
Figure 53:
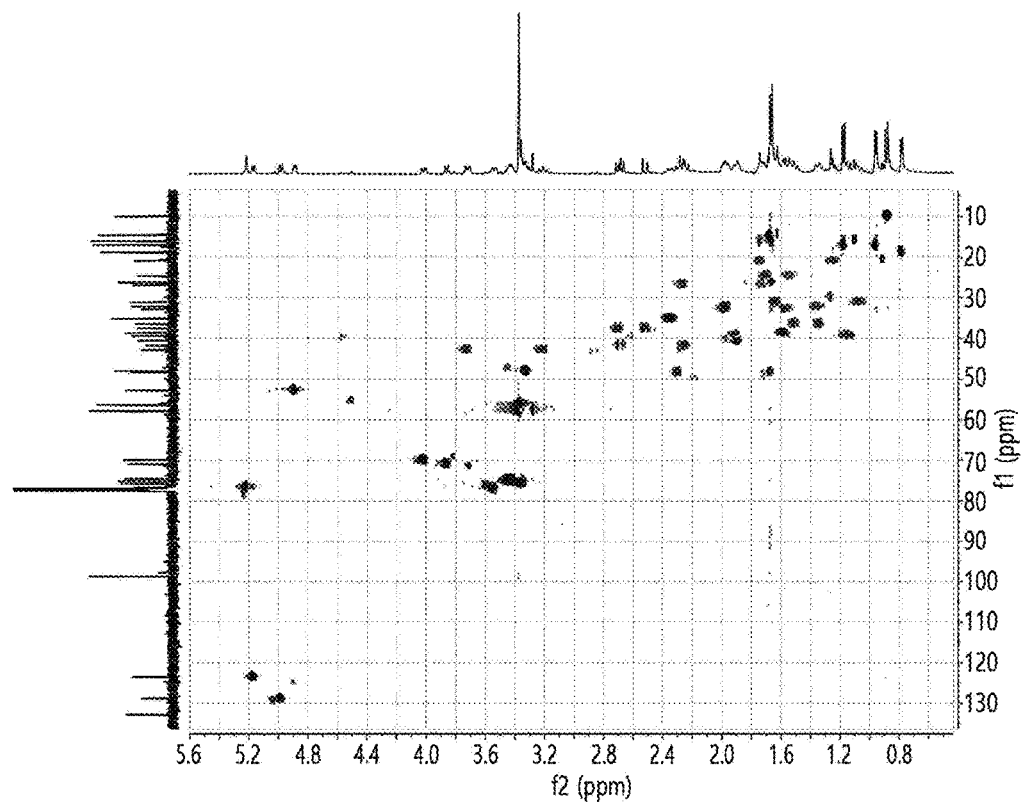
FIG. 53 shows nuclear magnetic resonance analysis (HSQC-NMR) results of 9-deoxo-31-O-demethyl-FK523.
Figure 54:
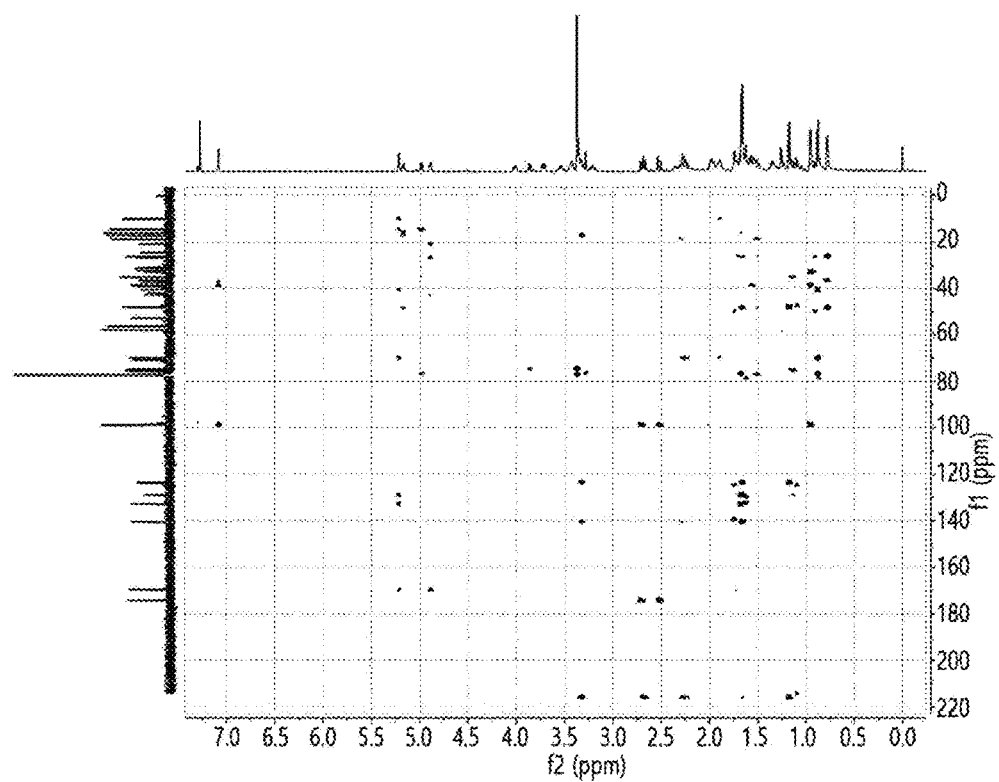
FIG. 54 shows nuclear magnetic resonance analysis (HMBC-NMR) results of 9-deoxo-31-O-demethyl-FK523.

Hereinafter, the present invention will be described in detail.

Meanwhile, each of the descriptions and embodiments disclosed herein may be applied to describe different descriptions and embodiments. That is, all of the combinations of various factors disclosed herein belong to the scope of the present invention. Furthermore, the scope of the present invention should not be limited by the detailed descriptions provided hereinbelow.

Also, those skilled in the art will recognize or be able to ascertain, using no more than routine experimentation, many equivalents to specific embodiments of the present invention. Such equivalents are intended to be encompassed in the scope of the following claims.

To solve these problems, the present invention provides methods of preparing nine novel compounds, compositions for promoting hair growth including each of the novel compounds by application of the preparation methods, and methods of alleviating, preventing, and treating hair loss.

An aspect of the present invention to achieve the above objects provides a compound selected from the group consisting of nine novel compounds, i.e., 9-deoxo-31-O-demethyl-prolyl-FK506 represented by Formula 1 below, 9-deoxo-36,37-dihydro-FK506 represented by Formula 2 below, 31-O-demethyl-36,37-dihydro-FK506 represented by Formula 3 below, 9-deoxo-31-O-demethyl-36,37-dihydro-FK506 represented by Formula 4 below, 9-deoxo-FK520 represented by Formula 5 below, 31-O-demethyl-FK520 represented by Formula 6 below, 9-deoxo-31-O-demethyl-FK520 represented by Formula 7 below, 9-deoxo-FK523 represented by Formula 8 below, and 9-deoxo-31-O-demethyl-FK523 represented by Formula 9 below, an isomer thereof, or a pharmaceutically acceptable salt thereof.

[Formula 1]

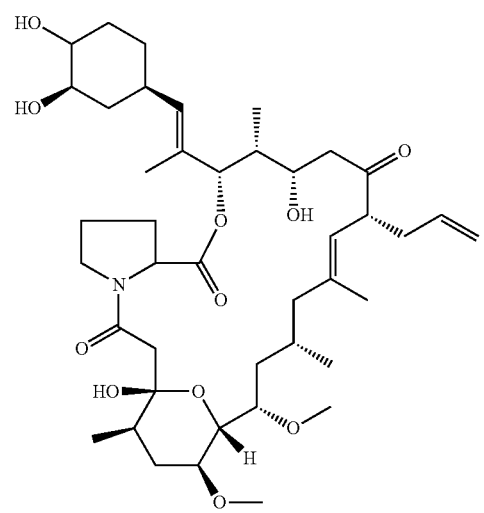

[Formula 2]

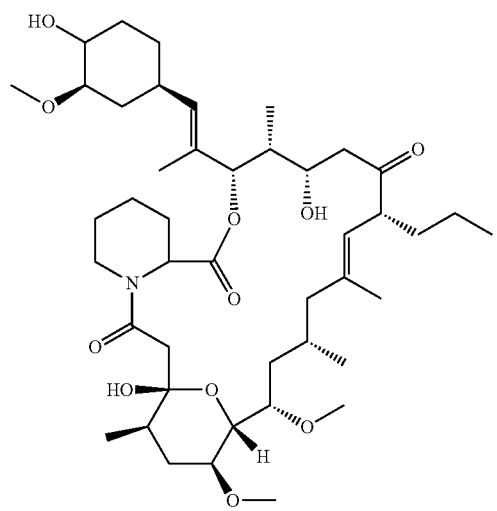

[Formula 3]
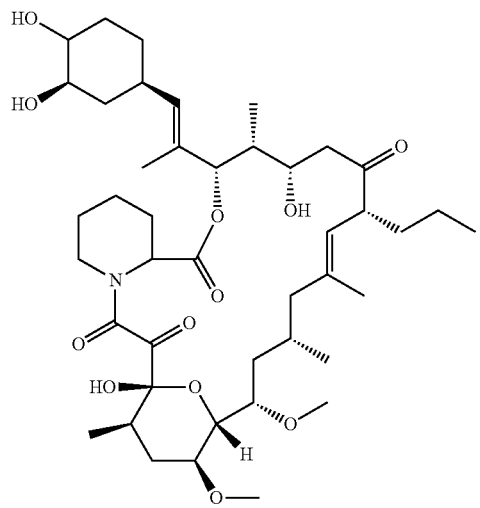
[Formula 4]
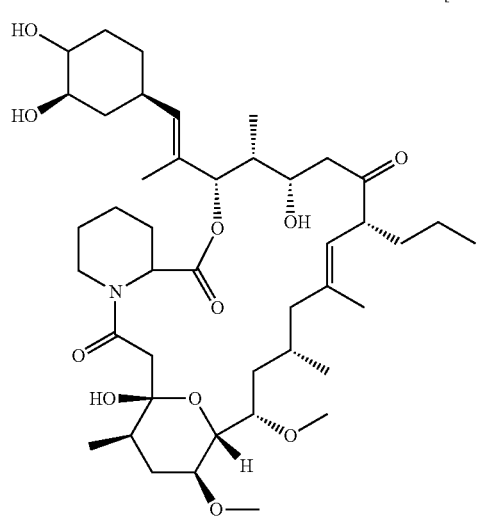
[Formula 5]
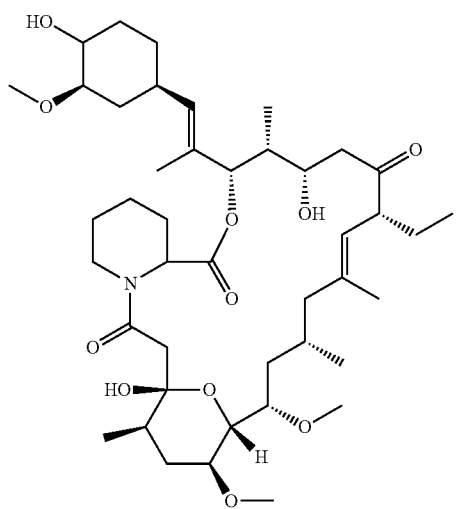
[Formula 6]
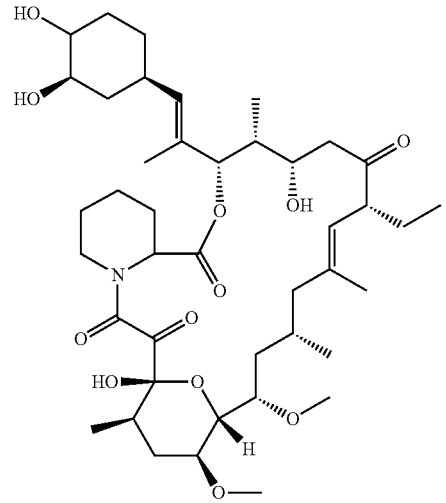
[Formula 7]
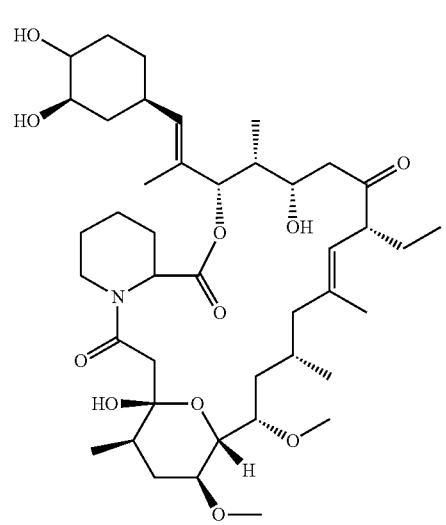
[Formula 8]
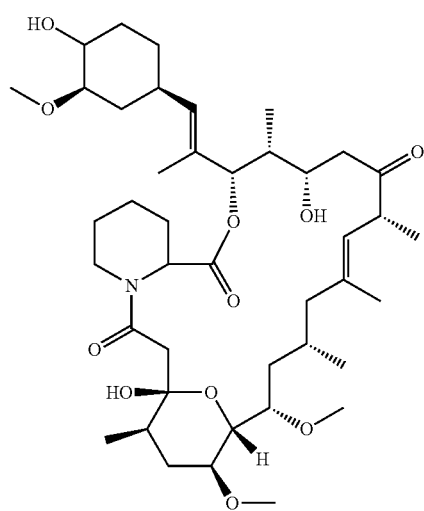

-continued

[Formula 9]

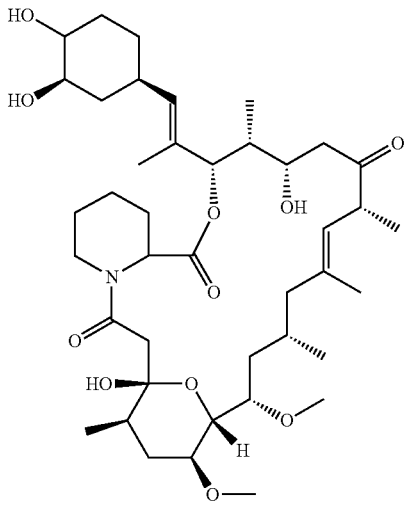

In a specific embodiment, the compound of the present invention may include isomers thereof or pharmaceutically acceptable salts thereof.

Isomers refer to compounds with the same chemical formula but a different atomic arrangement and may include, for example, structural isomers, geometric isomers, optical isomers (enantiomers), stereoisomers, and diastereomers.

The pharmaceutically acceptable salts may refer to any organic or inorganic addition salts of an original compound which do not cause side effects and impairing beneficial effects of the compound in a concentration effective for patients, but which are relatively non-toxic and harmless to the patients. For example, the pharmaceutically acceptable salt may be an acid addition salt formed of a pharmaceutically acceptable free acid. The acid addition salt may be prepared by way of any method commonly used in the art, for example, by dissolving the compound in an excess amount of an aqueous solution and precipitating a salt using a water-miscible organic solvent, e.g., methanol, ethanol, acetone, or acetonitrile. The compound and acid or alcohol (e.g., glycol monomethyl ether) in water in the same molar amount may be heated followed by drying of the mixture by evaporation, or a precipitated salt may be filtered by suction. In this regard, the free acid may be an organic or inorganic acid. The salt may be a pharmaceutically acceptable metal salt prepared using a base.

In another specific embodiment, the compound of the present invention may be in the form of a solvate or pro-drug, which is within the scope of the present invention. The solvate may preferably include a hydrate and an ethanolate.

The composition of the present invention may be used as a single formulation or combined with various drugs known to have preventive or therapeutic effects on hair loss, and the composition may be formulated using a pharmaceutically acceptable carrier or excipient into a single-dose dosage form or a unit dosage form in a multi-dose container.

As used herein, the term "pharmaceutically acceptable carrier" refers to a carrier or diluent used without causing irritation to a living organism and damaging biological activities or properties of the administered compound. Types of the carrier available in the present invention are not particularly limited, and any type of pharmaceutically acceptable carrier commonly used in the art may be used.

Non-limiting examples of the carrier may include a co-surfactant such as Transcutol, polyethylene glycol, Triacetin, and any mixture thereof; a surfactant such as Cremophor, Tween, Myrj, Poloxamer, Pluronic, Lutrol, Imwitor, Span, and Labrafil, alone or in a mixture; an oil such as Miglyol, Captex, and ethyl oleate, alone or in a mixture; and an organic acid such as erythorobic acid and citric acid, alone or in a mixture. These carriers may be used alone or in a mixture of at least two thereof.

Also, if required, the composition may further include any known additive such as an antioxidant, a buffer, and/or a bacteriostatic agent. The composition may be formulated into injectable dosage forms such as aqueous solutions, suspensions, and emulsions, pills, capsules, granules, or tablets, in combination with a diluent, a dispersant, a surfactant, a binder, a lubricant, or the like.

Another aspect of the present invention to achieve the above objects provides methods of preventing or treating hair loss, the methods including administering the composition to an individual.

As used herein, the term "individual" refers to all animals with hair loss or at risk of developing hair loss.

The composition of the present invention may include at least one selected from the nine novel compounds, an isomer thereof, or a salt thereof in a pharmaceutically effective amount. As used herein, the term "pharmaceutically effective amount" refers to an amount sufficient for treating a disease at a reasonable benefit/risk ratio applicable to medical treatment, and a daily dosage of the composition may generally be from 0.001 mg/kg to 1000 mg/kg, preferably 0.05 mg/kg to 200 mg/kg, and more preferably 0.1 mg/kg to 100 mg/kg once to several times per day. However, for the purpose of the present invention, it is preferred that a specific therapeutically effective amount for a specific patient be differently applied depending on various factors including the type and extent of a response to be achieved, a specific composition, including whether other formulations are used according to the case, the age, body weight, general health status, gender, and diet of the patient, administration time, administration route, excretion rate of the composition, duration of treatment, and a drug used in combination or concurrently with the specific composition, and similar factors well known in the medical field.

Although not particularly limited thereto, the composition of the present invention may be administered once a day or several times a day in divided doses.

The composition of the present invention may be administered alone or in combination with other therapeutic agents and may be administered sequentially or simultaneously with existing therapeutic agents. The composition may be administered in a single- or multiple-dosage form. It is important to administer the composition in a minimum amount that may exhibit a maximum effect without causing side effects, considering all of the above-described factors. The amount may be readily determined by those skilled in the art.

As used herein, the term "administration" refers to introducing the composition of the present invention into a patient by way of any appropriate method. The composition of the present invention may be administered by way of any oral or parenteral routes as long as the composition reaches a target tissue.

Administration modes of the composition of the present invention are not particularly limited, and any administration mode commonly available in the art may be used. Non-limiting examples of the administration mode include oral or parenteral administration modes. The composition of the present invention may be prepared into various dosage forms, depending on desired administration modes.

The composition for promoting hair growth of the present invention may be used to alleviate, prevent, or treat hair loss.

In the present invention, alopecia includes both non-cicatricial alopecia, which is temporary hair loss, and cicatricial alopecia caused by permanent destruction of hair follicles or hair roots, and non-cicatricial alopecia includes infectious hair loss, traumatic hair loss, inflammatory hair loss, congenital hair loss, endocrine hair loss, alopecia neoplastica, malnutrition hair loss, drug-induced hair loss, hair loss caused by abnormal hair structure, male-pattern hair loss, female-pattern hair loss, and alopecia areata.

As used herein, the term "alleviation" refers to all actions intended to delay progression of hair loss or alleviate symptoms of hair loss by administering the composition of the present invention to an individual.

As used herein, the term "prevention" refers to all actions intended to inhibit or delay hair loss by administration of the composition of the present invention to an individual.

As used herein, the term "treatment" refers to all actions intended to alleviate or beneficially change symptoms of hair loss by administering the composition of the present invention to an individual suspected to have hair loss. In a specific embodiment of the present invention, immunosuppressive effects of the nine novel compounds were confirmed by in vitro T cell activity assay. As a result, decreased immunosuppressive effects thereof were confirmed compared to those of FK506.

Also, in another specific embodiment of the present invention, effects of the nine novel compounds on promoting the growth of vibrissae were confirmed.

In another specific embodiment of the present invention, the effects of the nine novel compounds on promoting the growth of vibrissae in the length were confirmed, and the cell growth marker was confirmed based on histological results, and thus it was confirmed that the growth of vibrissae was continuously maintained.

These results indicate that the nine novel compounds have effects on promoting hair growth without side effects caused by immunosuppressive activity and can thereby be effectively used to alleviate, prevent, or treat hair loss.

Another aspect of the present invention to achieve the above objects provides biologically manufacturing processes of nine novel compounds, 9-deoxo-31-O-demethyl-prolyl-FK506, 9-deoxo-36,37-dihydro-FK506, 31-O-demethyl-36,37-dihydro-FK506, 9-deoxo-31-O-demethyl-36,37-dihydro-FK506, 9-deoxo-FK520, 31-O-demethyl-FK520, 9-deoxo-31-O-demethyl-FK520, 9-deoxo-FK523, and 9-deoxo-31-O-demethyl-FK523.

In the biological manufacturing processes, a culture temperature adopted in general processes of culturing microorganisms belonging to the genus *Streptomyces* is used. The culture temperature appropriate for the embodiment of the present invention may preferably be in the range of 23° C. to 30° C., more preferably, in the range of 25° C. to 28° C.

Also, in the manufacturing processes, the pH of the culturing process is maintained in the range of 6.5 to 9, preferably in the range of 7 to 8.

Meanwhile, it is important to maintain a high level of dissolved oxygen in the manufacturing processes. When the dissolved oxygen level in the early stage of culturing is assumed to be 100%, it is important to maintain a dissolved oxygen level of 30% or more until the culturing is terminated. To this end, the stirring may be performed at a rate of 800 rpm to 1,500 rpm.

The nine novel compounds produced by the cultured microbial cells in the manufacturing process may be extracted by way of a first extraction process, a second extraction process, and a third extraction process. In the present invention, the first extraction process is performed by way of an organic solvent extraction method, and a solvent used therefor may be ethyl acetate, methanol, or acetone, preferably ethyl acetate or methanol. The second extraction process may be performed using silica gel chromatography, and methanol or methylene chloride may be used as solvents. In addition, the third extraction process may be performed using chromatography, and a solvent used therefor may be acetonitrile, an ammonium acetate buffer, acetic acid, or formic acid, preferably acetonitrile. Application of these methods facilitates the recovery of the nine novel compounds and also increases the yield.

Another aspect of the present invention to achieve the above objects provides production strains available in the manufacture of nine novel compounds, i.e., *Streptomyces kanamyceticus* ΔfkbD-fkbM (accession number: KCTC13581BP), *Streptomyces kanamyceticus* ΔfkbD,tcsD (accession number: KCTC13580BP), *Streptomyces kanamyceticus* ΔfkbM,tcsD (accession number: KCTC13584BP), *Streptomyces kanamyceticus* ΔfkbD-fkbM,tcsD (accession number: KCTC13585BP), *Streptomyces kanamyceticus* ΔfkbD,tcsB (accession number: KCTC13579BP), *Streptomyces kanamyceticus* ΔfkbM,tcsB (accession number: KCTC13583BP), and *Streptomyces kanamyceticus* ΔfkbD-fkbM,tcsB (accession number: KCTC13582BP).

Another object of the present invention is to provide an over-the-counter (OTC) composition for promoting hair growth including at least one compound selected from nine novel compounds, an isomer thereof, or a pharmaceutically acceptable salt thereof as an active ingredient.

When the composition including at least one selected from the nine novel compounds is added to an OTC composition for the purpose of promoting hair growth, the compound may be added as it is or may be used together with other OTC components, and may be used appropriately according to any methods commonly used in the art. A mixing amount of the active ingredient may be appropriately determined according to the purpose of use.

As used herein, the term "OTC composition" refers to fibers or rubber products, or similar products used for the purpose of medical care, alleviation, treatment, or prevention of diseases in humans or animals; non-appliances, non-machinery, or similar products which have insignificant influences on or do not directly act upon the human body; and preparations used for sterilization, insecticide, and purposes similar thereto in order to prevent communicable diseases, and the OTC product does not include products used for the purposes of diagnosis, medical care, alleviation, treatment, or prevention of diseases of humans or animals, excluding appliances, machinery, and equipment; or products, other than appliances, machinery, or equipment, used for the purpose of exerting pharmacological effects upon the structure or functions of humans or animals. The OTC product may include formulations for external application and personal hygiene products.

Although not particularly limited thereto, the skin external agent may be prepared specifically as an ointment, a lotion, a spray, a patch, a cream, a powder, a suspension, a gel agent, or a form of gel. The personal hygiene product may be, but is not particularly limited to, specifically a soap, a cosmetic, a wet tissue, a tissue, a shampoo, a skin cream, a face cream, a toothpaste, a lipstick, a perfume, a makeup base, a foundation, a blusher, a mascara, an eye shadow, a sunscreen lotion, a hair care product, an air freshener gel, or a wash gel.

Also, the OTC composition of the present invention may be a disinfectant cleaner, shower foam, ointment, wet tissue, coating agent, or the like, but is not limited thereto, and formulating methods, dosages, methods of use, components, and the like of the OTC composition may be appropriately selected from conventional techniques known in the art.

The OTC composition of the present invention may further include a pharmaceutically acceptable carrier, excipient, or diluent in addition to the above-described components. The pharmaceutically acceptable carrier, excipient, or diluent is not limited as long as it does not adversely affect the effects of the present invention and may include a filler, an extender, a binder, a humectant, a disintegrant, a surfactant, a lubricant, a sweetener, an aromatic, and a preservative.

In an embodiment of the present invention, it was confirmed that the nine novel compounds have effects on promoting hair growth and may be used as OTC compositions for preventing hair loss and promoting hair growth.

Another object of the present invention is to provide a functional food composition for promoting hair growth including at least one of the nine novel compounds, an isomer thereof, or a sitologically acceptable salt thereof as an active ingredient.

Because hair growth-promoting effects and significantly reduced immunosuppressive activity are confirmed, the composition including at least one compound selected from the nine novel compounds may be prepared in the form of foods for preventing or alleviating hair loss-related diseases.

As used herein, the term "functional food" is the same as food for special health use, health functional food, and health food, and refers to a food having high medicinal and medical effects which is processed to effectively exert a body-regulating function as well as to supply nutrients. The food may be prepared in various forms such as tablets, capsules, powders, granules, liquids, and pills to obtain a beneficial effect in preventing or alleviating diseases related to hair loss.

The functional food of the present invention may be prepared by way of a method commonly used in the art and by adding raw materials and ingredients which are generally added in the art during preparation. In addition, the formulation of the functional food may be prepared without limitation as long as the formulation is acceptable as a food. The functional food of the present invention may be prepared in various types of formulations. Unlike general drugs, the food composition includes a food as a raw material, and therefore, it has advantages of being free from side effects that may occur when taken for a long period of time. The food composition is also excellent in portability, and therefore, the food of the present invention may be taken as a supplement agent for enhancing hair growth-promoting effects.

Specifically, the functional food is a food prepared by adding at least one compound selected from the nine novel compounds or an isomer thereof to a food material such as beverages, teas, flavors, gums, confectionery, or a food prepared as a capsule, powder, or suspension, which may be used as various foods such as beverages, gum, teas, vitamin complexes, and functional foods.

The food may be prepared in formulations such as tablets, granules, powders, capsules, liquid solutions, and pills according to any known manufacturing methods, and the amount of the composition of the present invention may be adjusted according to the formulation. The other ingredients except for the at least one compound selected from the nine novel compounds according to the present invention, as an active ingredient, are not particularly limited, and the composition may further include various flavoring agents or natural carbohydrates as an additional ingredient.

Examples of the natural carbohydrate include typical sugars, e.g.: monosaccharides such as glucose and fructose; disaccharides such as maltose and sucrose; and polysaccharides such as dextrin and cyclodextrin, and sugar alcohols such as xylitol, sorbitol, and erythritol. In addition to the foregoing, flavoring agents including natural flavoring agents such as taumatin and stevia extracts (e.g., rebaudioside A and glycyrrhizin) and synthetic flavoring agents (e.g., saccharin and aspartame) may advantageously be used.

Additionally, the composition or the functional food of the present invention may include a variety of nutrients, vitamins, minerals (electrolytes), synthetic and natural flavoring agents, colorants and fillers (cheese, chocolate, etc.), pectic acid or salts thereof, alginic acid or salts thereof, organic acids, protective colloidal thickeners, pH modifiers, stabilizers, preservatives, glycerin, alcohols, and carbonating agents used in carbonated beverages.

In addition, the functional food of the present invention may include fruit pulp for natural fruit juice, fruit juice drinks, and vegetable drinks. These ingredients may be used alone or in combination.

When the formulation is powder, the carrier may be lactose, talc, silica, aluminum hydroxide, calcium silicate, polyamide powder, or any mixture thereof.

When the formulation of the present invention is a solution or emulsion, the carrier may be a solvent, a solubilizer, or an emulsifier, e.g., water, ethanol, isopropanol, ethyl carbonate, ethyl acetate, benzyl alcohol, benzyl benzoate, propylene glycol, 1,3-butyl glycol oil, specifically cotton seed oil, peanut oil, corn seed oil, olive oil, castor oil, sesame oil, glycerol, an aliphatic ester, polyethylene glycol, or a fatty acid ester of sorbitan.

When the formulation is a suspension, the carrier may be a liquid diluent such as water, ethanol, or propylene glycol, a suspending agent such as ethoxylated isostearyl alcohol, polyoxyethylene sorbitol ester, and polyoxyethylene sorbitan ester, microcrystalline cellulose, aluminum metahydroxide, bentonite, agar, or tragacanth.

Another object of the present invention is to provide a cosmetic composition for promoting hair growth including at least one compound selected from the nine novel compounds, an isomer thereof, or a cosmetically acceptable salt thereof as an active ingredient.

As used herein, the "cosmetic composition" may be prepared in any formulation that is commercially manufactured, for example, a solution, an emulsion, a suspension, a paste, a cream, a lotion, a gel, a powder, a spray, a surfactant-containing cleaner, an oil, a soap, a liquid cleaner, a bath bomb, a foundation, a makeup base, an essence, a nourishing lotion, a foam, a pack, a softening water, a sunscreen cream, a sun oil, or the like.

When the formulation of the present invention is a solution or emulsion, the carrier may be a solvent, a solubilizer, or an emulsifier such as water, ethanol, isopropanol, ethyl carbonate, ethyl acetate, benzyl alcohol, benzyl benzoate, propylene glycol, 1,3-butyl glycol oil, glycerol, an aliphatic ester, polyethylene glycol, or a fatty acid ester of sorbitan.

When the formulation is a suspension, the carrier may be a liquid diluent such as water, ethanol, or propylene glycol, a suspending agent such as ethoxylated isostearyl alcohol, polyoxyethylene sorbitol ester, and polyoxyethylene sorbitan ester, microcrystalline cellulose, aluminum metahydroxide, bentonite, agar, or tragacanth.

When the formulation of the present invention is a paste, a cream, or a gel, the carrier may be animal oil, vegetable oil, wax, paraffin, starch, tragacanth, a cellulose derivative, polyethylene glycol, silicone, bentonite, silica, talc, or zinc oxide.

When the formulation of the present invention is a powder or spray, the carrier may be lactose, talc, silica, aluminum hydroxide, calcium silicate, or polyamide powder. Particularly, in the case of a spray, the formulation may further include a propellant such as a chlorofluorohydrocarbon, propane/butane, or dimethyl ether.

When the formulation of the present invention is a surfactant-containing cleaner, the carrier may be an aliphatic alcohol sulfate, aliphatic alcohol ether sulfate, sulfosuccinic acid monoester, isethionate, imidazolinium derivative, methyl taurate, sarcosinate, fatty acid amide ether sulfate, alkyl amido betaine, aliphatic alcohol, fatty acid glyceride, fatty acid diethanolamide, vegetable oil, lanolin derivative, or ethoxylated glycerol fatty acid ester.

In an embodiment of the present invention, effects of the nine novel compounds on promoting hair growth were confirmed, and the use of compositions including the same as cosmetic compositions for preventing hair loss and promoting hair growth was confirmed.

Best Mode

In an embodiment of the present invention, effects of the nine novel compounds on promoting hair growth were confirmed, and the use of compositions including the same as cosmetic compositions for preventing hair loss and promoting hair growth was confirmed.

Example 1: Preparation of 9-deoxo-31-O-demethvl-prolyl-FK506

Streptomyces kanamyceticus ΔfkbD-fkbM (accession number: KCTC13581BP), which is a 9-deoxo-31-O-demethyl-prolyl-FK506-producing strain, was constructed by inactivating fkbD-fkbM gene of Streptomyces kanamyceticus, which is an FK506-producing strain, via an in-frame deletion caused by double cross-over homologous recombination, according to a method introduced by Ban, Y. H. et al., (J. Nat. Prod. 2013, 76, 1091-1098).

Specifically, in order to construct a mutant of the FK506-producing Streptomyces kanamyceticus strain from which fkbD and fkbM genes were deleted, each gene was cloned to a pKC1139 vector and transferred to Escherichia coli ET12567/pUZ8002, and then the FK506-producing Streptomyces kanamyceticus strain was transformed with the vector by conjugation.

A method of constructing the strain may be explained more specifically as construction of an in-frame gene deletion plasmid and construction of a gene-deleted strain.

In the construction of the in-frame gene deletion plasmid, the E. coli-Streptomyces shuttle vector pKC1139 was used for in-frame gene deletion. Construction of the plasmid was performed by PCR of left- and right-flanking fragments of a target gene for deletion of Fosmid DNA derived from Streptomyces kanamyceticus. For deletion of the fkbD-fkbM gene, a primer pair of a left-flanking fragment, FkbD-MLF/FkbD-MLR, and a pair of a right-flanking fragment, FkbD-MRF/FkbD-MRR, were designed. All PCR fragments were isolated, digested with HindIII-XbaI or XbaI-EcoRI, and cloned to the pKC1139 vector. Information on the strains, plasmids, and primers used in this example are shown in Tables 1 and 2 below.

The plasmids used for construction of the gene-deleted strain are shown in Table 1. A plasmid for removing both C9 hydroxylase and 31-O-methyltransferase, pΔfkbD-fkbM, was transferred to E. coli ET12567/pUZ8002 and introduced into Streptomyces kanamyceticus by conjugation to delete the target gene by homologous recombination. A strain in which single cross-over occurred between the deletion plasmid and the chromosome of Streptomyces kanamyceticus was selected by culturing an apramycin-resistant transconjugant in the presence of apramycin at 37° C. (non-permissive temperature for replication of a pSG5-based replicon). Then, acquired colonies were proliferated three times at 28° C. without selection to allow second cross-over. The obtained double cross-over mutant, i.e., ΔfkbD-fkbM, was selected as a phenotype of apramycin sensitivity and identified by PCR, and optionally by Southern blotting.

The constructed fkbD-fkbM gene-deleted strain, Streptomyces kanamyceticus ΔfkbD-fkbM, was deposited under the terms of the Budapest Treaty with the International Strain Depositary at the Korean Collection for Type Cultures (KCTC) of the Korea Research Institute of Bioscience and Biotechnology on Jul. 17, 2018 (accession number: KCTC13581BP).

TABLE 1

Information on Strains and Plasmids Used

| Strain/vector | Relevant characteristic |
|---|---|
| Bacterial strains | |
| Escherichia coli | |
| DH5α | Host for general cloning |
| ET12567/pUZ8002 | Donor strain for intergeneric conjugation between E. coli and Streptomyces |
| Streptomyces | |
| Streptomyces kanamyceticus | Wild-type FK506 producing strain |
| ΔfkbD-fkbM | Mutant of S. kanamyceticus with an in-frame deletion of fkbD-fkbM |
| ΔfkbD-fkbM, tcsB | Mutant of S. kanamyceticus with an in-frame deletion of fkbD-fkbM, tcsB |
| ΔfkbD-fkbM, tcsD | Mutant of S. kanamyceticus with an in-frame deletion of fkbD-fkbM, tcsD |
| ΔfkbD, tcsD | Mutant of S. kanamyceticus with an in-frame deletion of fkbD, tcsD |
| ΔfkbD, tcsB | Mutant of S. kanamyceticus with an in-frame deletion of fkbD, tcsB |
| ΔfkbM, tcsD | Mutant of S. kanamyceticus with an in-frame deletion of fkbM, tcsD |
| ΔfkbM, tcsB | Mutant of S. kanamyceticus with an in-frame deletion of fkbM, tcsB |
| Plasmid | |
| pKC1139 | High-copy-number temperature-sensitive E. coli-Streptomyces shuttle vector |
| pΔfkbD | Deletion plasmid with in-frame deletion of 51 bp internal fkbD fragment |
| pΔfkbM | Deletion plasmid with in-frame deletion of 507 bp internal fkbM fragment |
| pΔfkbD-fkbM | Deletion plasmid with in-frame deletion of 1100 bp internal fkbDM fragment |
| pΔtcsB | Deletion plasmid with in-frame deletion of 2090 bp internal tcsB fragment |
| pΔtcsD | Deletion plasmid with in-frame deletion of 1154 bp internal tcsD fragment |

TABLE 2

Information on Primers Used

| Primer | Sequence 5' to 3' (Restriction site underlined) | Restriction enzyme |
|---|---|---|
| FkbDLF | TATAAAGCTTCGGAGCCCCGGTGGACCT | HindIII |
| FkbDLR | TTAATCTAGACGTCGCCTCGTCGTCGCT | XbaI |
| FkbDRF | GTAATCTAGAGTCGGCTACTGCCTCTAC | XbaI |
| FkbDRR | GAATGAATTCCGACGAACAGCGGTTCCT | EcoRI |
| FkbMLF | TACGAAGCTTTCTGTTCGGCATCCAGCA | HindIII |
| FkbMLR | TAGCTCTAGAGTCACCCGGGAGCAGTTC | XbaI |
| FkbMRF | TATATCTAGAGACACCGAAGGCGCGCTC | XbaI |
| FkbMRR | TTAAGAATTCGAACACCGAGGCCGTCCA | EcoRI |
| FkbD-MLF | TATAAAGCTTCGGAGCCCCGGTGGACCT | HindIII |
| FkbD-MLR | TTAATCTAGACGTCGCCTCGTCGTCGCT | XbaI |
| FkbD-MRF | TATATCTAGAGACACCGAAGGCGCGCTC | XbaI |
| FkbD-MRR | TTAAGAATTCGAACACCGAGGCCGTCCA | EcoRI |
| TcsBLF | GACAAGCTTATGCTGGCGGTGAAGGCG | HindIII |
| TcsBLR | CCGTCTAGACCAGAAGGAATCGAGCCGGAA | XbaI |
| TcsBRF | CAGTCTAGAGTGATCCGTGCCCTGCACTCC | XbaI |
| TcsBRR | GCCGAATTCGATGACGATGTCCGGGTCG | EcoRI |
| TcsDLF | GCTAAGCTTCTCAGGCGTCTGCGGATGC | HidIII |
| TcsDLR | ATCGGATCCTTCGCTCACCGGGGCTGCC | BamHI |
| TcsDRF | AGCAGATCTGGCATGTTCTGGTCAGTCC | BglI |
| TcsDRR | GTCGAATTCCATGCCACGAACGGGTCGA | EcoRI |

9-Deoxo-31-O-demethyl-prolyl-FK506 was prepared by culturing the constructed production strain, *Streptomyces kanamyceticus* ΔfkbD-fkbM (accession number: KCTC13581BP). This will be described in more detail. 50 mL of an R2YE medium (including 103 g/L sucrose, 10 g/L glucose, 0.25 g/L K$_2$SO$_4$, 10.12 g/L MgCl$_2$·6H$_2$O, 0.1 g/L casamino acid, 50 mL/L yeast extract (10%), 100 mL/L TES buffer (5.73%, pH 7.2), 10 mL/L potassium phosphate (0.5%), 80 mL/L CaCl$_2$·2H$_2$O (3.68%), 15 mL/L L-proline (20%), 2 mL/L trace element solution, and 5 mL/L NaOH (1 N)) was added to a 250 mL baffled flask, and the production strain was inoculated thereinto. Then, the strain was pre-incubated in a rotary shaker incubator at 28° C. and 180 rpm for two days. Subsequently, 10 mL of the pre-incubated culture was inoculated into 1 L of the R2YE medium contained in a 3 L Erlenmeyer flask. After inoculation, the strain was incubated at 28° C. and 180 rpm for 6 days. After 6 days of the incubation, 9-deoxo-31-O-demethyl-prolyl-FK506 was extracted by using a first extraction process.

The first extraction process was performed as follows. First, methanol was added to the culture broth in an equal volume and mixed for 30 minutes, and the microbial cells were removed by centrifugation, and then an extract from which the microbial cells were removed was concentrated using a rotary evaporator. After the concentrated extract was reconstituted in water, ethyl acetate was added in twice the volume of the water and shaken for the extraction. The mixture was left until aqueous and organic layers were separated. After the layers were separated, an upper layer, i.e., an organic solvent layer, was recovered and concentrated using a rotary evaporator, and a weight after concentration was measured. The extract obtained by way of the first extraction process was passed through a column filled with silica gel. In this case, an amount of the silica gel was 15 times the weight of the extract obtained by way of the first extraction process, and methanol and methylene chloride mixed in five ratios (Aliquot 1. 0:100, Aliquot 2. 1:100, Aliquot 3. 1:10, Aliquot 4. 1:1, and Aliquot 5. 100:0) were used as mobile phases. In Aliquot 3, 9-deoxo-31-O-demethyl-prolyl-FK506 was confirmed. Aliquot 3 obtained as described above was concentrated using a rotary evaporator and ultimately purified by HPLC.

The concentrate was lyophilized to obtain 9-deoxo-31-O-demethyl-prolyl-FK506 represented by Formula 1 in the form of powder.

The prepared 9-deoxo-31-O-demethyl-prolyl-FK506 was identified as follows. Specifically, high-performance liquid chromatography analysis, mass spectrometry, and nuclear magnetic resonance analysis were conducted. Analysis results of 9-deoxo-31-O-demethyl-prolyl-FK506 are shown in Table 3 and FIGS. 1 to 6, and it was confirmed that 9-deoxo-31-O-demethyl-prolyl-FK506 was produced by the constructed production strain *Streptomyces kanamyceticus* ΔfkbD-fkbM based on the results.

Analysis results of 9-deoxo-31-O-demethyl-prolyl-FK506 (molecular formula: $C_{41}H_{57}NO_{11}$ and molecular weight: 749.4714) are shown in Table 3 below.

TABLE 3

| Analysis method | Analysis results | | |
|---|---|---|---|
| High-performance liquid chromatography analysis | HPLC was performed using a 45-55% acetonitrile aqueous solution as a mobile phase at a flow rate of 1 mL/min and analyzed using a UV detector at 205 nm. In this regard, a retention time of 9-deoxo-31-O-demethyl-prolyl-FK506 was 22 minutes. | | |
| Mass spectrometry | (ESI-HR-MS) Calcd. for $C_{42}H_{67}NNaO_{11}^+$: 784.4606, found: m/z 784.4611. | | |
| | No. | carbon (ppm) | proton (ppm) |
| Nuclear magnetic resonance analysis | 1 | 170.09 | |
| | 2 | 59.06 | 4.36 (1H, dd, J = 10.5 Hz, 3.5 Hz) |
| | 3 | 29.35 | 1.97 (1H, m), 2.19 (1H, m) |

TABLE 3-continued

| | | |
|---|---|---|
| 4 | 24.89 | 1.96 (1H, m), 1.98 (1H, m) |
| 5 | | |
| 6 | 47.61 | 3.55 (1H, m), 3.64 (1H, m) |
| 7 | 171.99 | |
| 8 | 39.34 | 2.56 (1H, d, J = 15.0 Hz), 2.63 (1H, d, J = 15.0 Hz) |
| 9 | 98.73 | |
| 10 | 38.72 | 1.59 (1H, m) |
| 11 | 32.86 | 1.56 (1H, m), 1.99 (1H, m) |
| 12 | 74.73 | 3.43 (1H, m) |
| 13 | 71.14 | 3.85 (1H, dd, J = 10.0 Hz, 5.0 Hz) |
| 14 | 77.39 | 3.54 (1H, m) |
| 15 | 36.57 | 1.34 (1H, m), 1.47 (1H, m) |
| 16 | 25.72 | 1.61 (1H, m) |
| 17 | 49.17 | 1.70 (1H, m), 2.35 (1H, m) |
| 18 | 141.22 | |
| 19 | 122.04 | 4.99 (1H, d, J = 5.0 Hz) |
| 20 | 53.54 | 3.38 (1H, d, J = 5.0 Hz) |
| 21 | 214.00 | |
| 22 | 44.25 | 2.35 (1H, m), 2.67 (1H, m) |
| 23 | 69.23 | 4.04 (1H, br d, J = 10.0 Hz) |
| 24 | 41.26 | 1.83 (1H, dd, J = 10.0 Hz, 2.0 Hz) |
| 25 | 78.28 | 5.18 (1H, d, J = 2.0 Hz) |
| 26 | 132.64 | |
| 27 | 129.79 | 5.01 (1H, d, J = 2.0 Hz) |
| 28 | 35.23 | 2.35 (1H, m) |
| 29 | 39.39 | 1.14 (1H, m), 1.90 (1H, m) |
| 30 | 75.81 | 3.35 (1H, m) |
| 31 | 75.28 | 3.44 (1H, m) |
| 32 | 32.29 | 1.36 (1H, m), 1.98 (1H, m) |
| 33 | 31.22 | 1.06 (1H, m), 1.61 (1H, m) |
| 34 | 35.78 | 2.25 (1H, m), 2.45 (1H, m) |
| 35 | 135.80 | 5.72 (1H, m) |
| 36 | 116.84 | 5.00 (1H, dd, J = 15.0 Hz, 10.0 Hz), 5.03 (1H, dd, J = 15.0 Hz, 5.0 Hz) |
| 37 | 17.20 | 0.96 (3H, d, J = 5 Hz) |
| 38 | 19.10 | 0.77 (3H, d, J = 5 Hz) |
| 39 | 15.90 | 1.67 (3H, s) |
| 40 | 10.13 | 0.90 (3H, d, J = 5 Hz) |
| 41 | 14.41 | 1.65 (3H, s) |
| 42 | 56.48 | 3.38 (3H, s) |
| 43 | 57.98 | 3.37 3H, s) |

Based on $^1$H-NMR and $^{13}$C-NMR results, a ketone carbon ($\delta_C$ 214.00), two carbonyl carbons ($\delta_C$ 171.99 and 170.09), an exomethylene backbone ($\delta_C$ 116.84 and 135.80), and 2 olefin backbones ($\delta_C$ 141.22 and 122.04; and $\delta_C$ 132.64 and 129.79) were confirmed as characteristic functional groups, and a dioxygenated quaternary carbon ($\delta_C$ 98.73), 7 oxygenated methine carbons ($\delta_C$ 78.28, 77.39, 75.28, 75.81, 74.73, 71.14, and 69.23), 2 methoxy carbons ($\delta_C$ 57.98 and 56.48), and 5 methyl carbons ($\delta_C$ 19.10, 17.20, 15.90, 14.41, and 10.13) were observed. The obtained compound was confirmed as an FK506 derivative consisting of 42 carbon atoms. In order to accurately identify the structure of the compound, 2D-NMR was confirmed. As a result of identifying proton coupling using gCOSY, it was confirmed that the compound is not FK506 having a pipecolyl backbone but a compound including a prolyl backbone without a CH$_2$ functional group, based on couplings of H-2 to H-4. Based on gHMBC data, it was confirmed that C-9 of the compound was not a ketone but a backbone reduced to CH$_2$ based on correlation of H-9 ($\delta_H$ 2.56, 2.63) with C-8 ($\delta_C$ 171.99) and C-10 ($\delta_C$ 98.73). In addition, since two methoxy functional groups are linked to C-13 and C-15, it was confirmed that a methoxy group was not present at C-31. In conclusion, the compound was confirmed as 9-deoxo-31-O-demethyl-prolyl-FK506.

Example 2: Preparation of 9-deoxo-36,37-dihydro-FK506

*Streptomyces kanamyceticus* ΔfkbD,tcsD (accession number: KCTC13580BP), which is a 9-deoxo-36,37-dihydro-FK506-producing strain, was constructed by inactivating fkbD and tcsD genes of *Streptomyces kanamyceticus*, which is an FK506-producing strain, via an in-frame deletion caused by double cross-over homologous recombination, according to a method introduced by Ban, Y. H. et al., (*J. Nat. Prod.* 2013, 76, 1091-1098).

Specifically, in order to construct a mutant of the FK506-producing *Streptomyces kanamyceticus* strain from which fkbD and tcsD genes were deleted, each gene was cloned to a pKC1139 vector and transferred to *Escherichia coli* ET12567/pUZ8002, and then the FK506-producing *Streptomyces kanamyceticus* strain was transformed with the vector by conjugation.

A method of constructing the strain may be explained more specifically as construction of an in-frame gene deletion plasmid and construction of a gene-deleted strain.

In the construction of the in-frame gene deletion plasmid, the *E. coli*-*Streptomyces* shuttle vector pKC1139 was used for in-frame gene deletion. Construction of the plasmid was performed by PCR of left- and right-flanking fragments of a target gene for deletion of Fosmid DNA derived from *Streptomyces kanamyceticus*. For deletion of the fkbD gene, a primer pair of a left-flanking fragment, FkbDLF/FkbDLR, and a pair of a right-flanking fragment, FkbDRF/FkbDRR, were designed. For deletion of the tcsD gene, a primer pair of a left-flanking fragment, TcsDLF/TcsDLR, and a pair of a right-flanking fragment, TcsDRF/TcsDRR, were designed. All PCR fragments were isolated, digested with HindIII-XbaI or XbaI-EcoRI, and cloned to the pKC1139 vector. Information on the strains, plasmids, and primers used in this example are shown in Tables 1 and 2.

The plasmids used for construction of the gene-deleted strain are shown in Table 1. A plasmid for removing C9 hydroxylase, pΔfkbD, was transferred to *E. coli* ET12567/pUZ8002 and introduced into *Streptomyces kanamyceticus* by conjugation to delete the target gene by homologous recombination. A strain in which single cross-over occurred between the deletion plasmid and the chromosome of *Streptomyces kanamyceticus* was selected by culturing an apramycin-resistant transconjugant in the presence of apramycin at 37° C. (non-permissive temperature for replication of a pSG5-based replicon). Then, acquired colonies were proliferated three times at 28° C. without selection to allow second cross-over. The obtained double cross-over mutant, i.e., ΔfkbD, was selected as a phenotype of apramycin sensitivity and identified by PCR, and optionally by Southern blotting.

The tcsD gene was deleted using the same method as that used in deletion of the fkbD gene by introducing pΔtcsD into the constructed fkbD gene-deleted *Streptomyces kanamyceticus* ΔfkbD. ΔfkbD,tcsD was selected as a phenotype of apramycin sensitivity and identified by PCR, and optionally by Southern blotting.

The constructed strain *Streptomyces kanamyceticus* ΔfkbD,tcsD from which fkbD and tcsD genes were deleted was deposited under the terms of the Budapest Treaty with the International Strain Depositary at the Korean Collection for Type Cultures (KCTC) of the Korea Research Institute of Bioscience and Biotechnology on Jul. 17, 2018 (accession number: KCTC13580BP).

9-Deoxo-36,37-dihydro-FK506 was prepared by culturing the mutant strain, *Streptomyces kanamyceticus* ΔfkbD, tcsD (accession number: KCTC13580BP). This will be described in more detail. 50 mL of an R2YE medium (including 103 g/L sucrose, 10 g/L glucose, 0.25 g/L $K_2SO_4$, 10.12 g/L $MgCl_2 \cdot 6H_2O$, 0.1 g/L casamino acid, 50 mL/L yeast extract (10%), 100 mL/L TES buffer (5.73%, pH 7.2), 10 mL/L potassium phosphate (0.5%), 80 mL/L $CaCl_2 \cdot 2H_2O$ (3.68%), 15 mL/L L-proline (20%), 2 mL/L trace element solution, and 5 mL/L NaOH (1 N)) was added to a 250 mL baffled flask, and the production strain was inoculated thereinto. Then, the strain was pre-incubated in a rotary shaker incubator at 28° C. and 180 rpm for two days. Subsequently, 10 mL of the pre-incubated culture was inoculated into 1 L of the R2YE medium contained in a 3 L Erlenmeyer flask. After inoculation, the strain was incubated at 28° C. and 180 rpm for 6 days. After 6 days of the incubation, 9-deoxo-36,37-dihydro-FK506 produced thereby was extracted by using a first extraction process.

The first extraction process was performed as follows. First, methanol was added to the culture broth in an equal volume and mixed for 30 minutes, and the microbial cells were removed by centrifugation, and then the supernatant was concentrated using a rotary evaporator. After the concentrated extract was dissolved in water, ethyl acetate was added in twice the volume and mixed. The mixture was left until layers were separated. After the layers were separated, an upper layer, i.e., an organic solvent layer, was recovered and concentrated using a rotary evaporator, and a weight after concentration was measured. The extract obtained by way of the first extraction process was passed through a column filled with silica gel. In this case, an amount of the silica gel was 15 times the weight of the extract obtained by way of the first extraction process, and methanol and methylene chloride mixed in five ratios (Aliquot 1. 0:100, Aliquot 2. 1:100, Aliquot 3. 1:10, Aliquot 4. 1:1, and Aliquot 5. 100:0) were used as mobile phases. In Aliquot 3, 9-deoxo-36,37-dihydro-FK506 was confirmed. Aliquot 3 obtained as described above was concentrated using a rotary evaporator and ultimately purified by HPLC.

The concentrate was lyophilized to obtain 9-deoxo-36, 37-dihydro-FK506 represented by Formula 2 in the form of powder.

The prepared 9-deoxo-36,37-dihydro-FK506 was identified as follows. Specifically, high-performance liquid chromatography analysis, mass spectrometry, and nuclear magnetic resonance analysis were conducted. Analysis results of 9-deoxo-36,37-dihydro-FK506 are shown in Table 4 and FIGS. 7 to 12, and it was confirmed that 9-deoxo-36,37-dihydro-FK506 was produced by the constructed production strain *Streptomyces kanamyceticus* ΔfkbD,tcsD based on the results.

Analysis results of 9-deoxo-36,37-dihydro-FK506 (molecular formula: $C_{44}H_{73}NO_{11}$ and molecular weight: 792.06) are shown in Table 4 below.

TABLE 4

| Analysis method | Analysis results |
| --- | --- |
| High-performance liquid chromatography analysis | HPLC was performed using a 45-55% acetonitrile aqueous solution as a mobile phase at a flow rate of 1 mL/min and analyzed using a UV detector at 205 nm. In this regard, a retention time of 9-deoxo-36,37-dihydro-FK506 was 51 minutes. |
| Mass spectrometry | (ESI-HR-MS) Calcd. for $C_{44}H_{73}NNaO_{11}^+$: 814.5076, found: m/z 814.5083 |

TABLE 4-continued

| | No. | carbon (ppm) | proton (ppm) |
|---|---|---|---|
| Nuclear magnetic resonance analysis | 1 | 169.39 | |
| | 2 | 52.59 | 4.85 (1H, br d, J = 5.0 Hz) |
| | 3 | 26.58 | 1.70 (1H, m), 2.24 (1H, m) |
| | 4 | 20.70 | 1.31 (1H, m), 1.72 (1H, m) |
| | 5 | 24.42 | 1.51 (1H, m), 1.68 (1H, m) |
| | 6 | 42.65 | 3.19 (1H, m), 3.69 (1H, m) |
| | 7 | 173.96 | |
| | 8 | 36.25 | 2.49 (1H, d, J = 15.0 Hz), 2.66 (1H, d, J = 15.0 Hz) |
| | 9 | 98.50 | |
| | 10 | 38.39 | 1.56 (1H, m) |
| | 11 | 31.12 | 1.60 (1H, m), 1.94 (1H, m) |
| | 12 | 74.33 | 3.40 (1H, m) |
| | 13 | 70.6 | 3.84 (1H, dd, J = 10.0 Hz, 5.0 Hz) |
| | 14 | 77.11 | 3.53 (1H, m) |
| | 15 | 36.57 | 1.34 (1H, m), 1.47 (1H, m) |
| | 16 | 25.64 | 1.50 (1H, m) |
| | 17 | 48.49 | 1.65 (1H, m), 2.32 (1H, m) |
| | 18 | 140.82 | |
| | 19 | 122.20 | 5.05 (1H, d, J = 5.0 Hz) |
| | 20 | 53.45 | 3.21 (1H, d, J = 5.0 Hz) |
| | 21 | 215.35 | |
| | 22 | 41.74 | 2.21 (1H, br d, J = 15 Hz), 2.66 (1H, br d, J = 15 Hz) |
| | 23 | 69.64 | 3.97 (1H, m) |
| | 24 | 40.26 | 1.87 (1H, m) |
| | 25 | 76.50 | 5.19 (1H, br s) |
| | 26 | 132.42 | |
| | 27 | 128.71 | 4.97 (1H, d, J = 5.0 Hz) |
| | 28 | 34.81 | 2.35 (1H, m) |
| | 29 | 34.84 | 0.93 (1H, m), 2.01 (1H, m) |
| | 30 | 84.13 | 3.00 (1H, m) |
| | 31 | 73.58 | 3.39 (1H, m) |
| | 32 | 30.64 | 1.34 (1H, m), 1.98 (1H, m) |
| | 33 | 31.15 | 1.06 (1H, m), 1.61 (1H, m) |
| | 34 | 33.82 | 1.42 (1H, m), 1.65 (1H, m) |
| | 35 | 20.41 | 1.21 (2H, m) |
| | 36 | 13.91 | 0.88 (3H, t, J = 7.5 Hz) |
| | 37 | 16.87 | 0.93 (3H, d, J = 5 Hz) |
| | 38 | 18.84 | 0.76 (3H, d, J = 5 Hz) |
| | 39 | 15.45 | 1.63 (3H, s) |
| | 40 | 10.13 | 0.90 (3H, d, J = 5 Hz) |
| | 41 | 13.91 | 1.66 (3H, s) |
| | 42 | 56.10 | 3.35 (3H, s) |
| | 43 | 57.64 | 3.36 (3H, s) |
| | 44 | 56.56 | 3.38 3H, s) |

Based on $^1$H-NMR, $^{13}$C-NMR, and gHSQC results, the obtained compound consists of a total of 44 carbon atoms, and one methoxy group ($\delta_H$ 3.39 and $\delta_C$ 56.56) and one CH$_2$ group ($\delta_H$ 2.24, $\delta_H$ 1.70, and $\delta_C$ 20.70) were additionally observed, the exomethylene functional group was not observed, and a triplet coupling of a methyl group ($\delta$H 0.88 and $\delta_C$ 13.91) and a CH$_2$ group ($\delta_H$ 1.21 and $\delta_C$ 20.41) was observed. In order to accurately identify the structure, 2D-NMR was performed. As a result of identifying proton coupling by gCOSY, it was confirmed that the compound is FK506 including a pipecolyl backbone, and one CH$_2$ functional group ($\delta_H$ 2.24, $\delta_H$ 1.70, and $\delta_C$ 20.70) is present on the pipecolyl backbone based on couplings of H-2 to H-5. Based on gHMBC, it was confirmed that three methoxy hydrogens ($\delta_H$ 3.39, 3.36, and 3.35) were correlated with C-31 ($\delta_C$ 77.11), C-15 ($\delta_C$ 77.11), and C-13 ($\delta_C$ 74.33) respectively, and the methyl group ($\delta_H$ 0.88 and $\delta_C$ 13.91) and the CH$_2$ group ($\delta_H$ 1.21 and $\delta_C$ 20.41) observed in a triplet coupled state were correlated with C-21/33. Therefore, as a compound produced by the tcsD gene-deleted strain, 9-deoxo-36,37-dihydro-FK506 was determined to have a structure in the form where a double bond present between C-36/37 was reduced.

Example 3: Preparation of 31-O-demethyl-36,37-dihydro-FK506

*Streptomyces kanamyceticus* ΔfkbM,tcsD (accession number: KCTC13584BP), which is a 31-O-demethyl-36,37-dihydro-FK506-producing strain, was constructed by inactivating fkbM and tcsD genes of *Streptomyces kanamyceticus*, which is an FK506-producing strain, via an in-frame deletion caused by double cross-over homologous recombination, according to a method introduced by Ban, Y. H. et al., (*J. Nat. Prod.* 2013, 76, 1091-1098).

Specifically, in order to construct a mutant of the FK506-producing *Streptomyces kanamyceticus* strain from which fkbM and tcsD genes were deleted, each gene was cloned to a pKC1139 vector and transferred to *Escherichia coli* ET12567/pUZ8002, and then the FK506-producing *Streptomyces kanamyceticus* strain was transformed with the vector by conjugation.

A method of constructing the strain may be explained more specifically as construction of an in-frame gene deletion plasmid and construction of a gene-deleted strain.

In the construction of the in-frame gene deletion plasmid, the *E. coli-Streptomyces* shuttle vector pKC1139 was used for in-frame gene deletion. Construction of the plasmid was performed by PCR of left- and right-flanking fragments of a target gene for deletion of Fosmid DNA derived from *Streptomyces kanamyceticus*. For deletion of the fkbM gene, a primer pair of a left-flanking fragment, FkbMLF/FkbMLR, and a pair of a right-flanking fragment, FkbMRF/FkbMRR, were designed. For deletion of the tcsD gene, a primer pair of a left-flanking fragment, TcsDLF/TcsDLR, and a pair of a right-flanking fragment, TcsDRF/TcsDRR, were designed. All PCR fragments were isolated, digested with HindIII-XbaI or XbaI-EcoRI, and cloned to the pKC1139 vector. Information on the strains, plasmids, and primers used in this example are shown in Tables 1 and 2.

The plasmids used for construction of the gene-deleted strain are shown in Table 1. A plasmid for removing 31-O-methyltransferase, pΔfkbM, was transferred to *E. coli* ET12567/pUZ8002 and introduced into *Streptomyces kanamyceticus* by conjugation to delete the target gene by homologous recombination. A strain in which single cross-over occurred between the deletion plasmid and the chromosome of *Streptomyces kanamyceticus* was selected by culturing an apramycin-resistant transconjugant in the presence of apramycin at 37° C. (non-permissive temperature for replication of a pSG5-based replicon). Then, acquired colonies were proliferated three times at 28° C. without selection to allow second cross-over. The obtained double cross-over mutant, i.e., ΔfkbM, was selected as a phenotype of apramycin sensitivity and identified by PCR, and optionally by Southern blotting.

The tcsD gene was deleted using the same method as that used in deletion of the fkbM gene by introducing pΔtcsD into the constructed fkbM gene-deleted *Streptomyces kanamyceticus* ΔfkbM. ΔfkbM,tcsD was selected as a phenotype of apramycin sensitivity and identified by PCR, and optionally by Southern blotting.

The constructed strain *Streptomyces kanamyceticus* ΔfkbM,tcsD from which fkbM and tcsD genes were deleted was deposited under the terms of the Budapest Treaty with the International Strain Depositary at the Korean Collection for Type Cultures (KCTC) of the Korea Research Institute of Bioscience and Biotechnology on Jul. 17, 2018 (accession number: KCTC13584BP).

31-O-demethyl-36,37-dihydro-FK506 was prepared by culturing the constructed production strain, *Streptomyces kanamyceticus* ΔfkbM,tcsD (accession number: KCTC13584BP). This will be described in more detail. 50 mL of an R2YE medium (including 103 g/L sucrose, 10 g/L glucose, 0.25 g/L $K_2SO_4$, 10.12 g/L $MgCl_2 \cdot 6H_2O$, 0.1 g/L casamino acid, 50 mL/L yeast extract (10%), 100 mL/L TES buffer (5.73%, pH 7.2), 10 mL/L potassium phosphate (0.5%), 80 mL/L $CaCl_2 \cdot 2H_2O$ (3.68%), 15 mL/L L-proline (20%), 2 mL/L trace element solution, and 5 mL/L NaOH (1 N)) was added to a 250 mL baffled flask, and the production strain was inoculated thereinto. Then, the strain was pre-incubated in a rotary shaker incubator at 28° C. and 180 rpm for two days. Subsequently, 10 mL of the pre-incubated culture was inoculated into 1 L of the R2YE medium contained in a 3 L Erlenmeyer flask. After inoculation, the strain was incubated at 28° C. and 180 rpm for 6 days. After 6 days of the incubation, 31-O-demethyl-36,37-dihydro-FK506 produced thereby was extracted by using a first extraction process.

The first extraction process was performed as follows. First, methanol was added to the culture broth in an equal volume and mixed for 30 minutes, and the microbial cells were removed by centrifugation, and then an extract from which the microbial cells were removed was concentrated using a rotary evaporator. After the concentrated extract was dissolved in water, ethyl acetate was added in twice the volume of the extract and mixed, and the mixture was left until layers were separated. After the layers were separated, an upper layer, i.e., an organic solvent layer, was recovered and concentrated using a rotary evaporator, and a weight after concentration was measured. The extract obtained by way of the first extraction process was passed through a column filled with silica gel. In this case, an amount of the silica gel was 15 times the weight of the extract obtained by way of the first extraction process, and methanol and methylene chloride mixed in five ratios (Aliquot 1. 0:100, Aliquot 2. 1:100, Aliquot 3. 1:10, Aliquot 4. 1:1, and Aliquot 5. 100:0) were used as mobile phases. In Aliquot 3, 31-O-demethyl-36,37-dihydro-FK506 was confirmed. Aliquot 3 obtained as described above was concentrated using a rotary evaporator and ultimately purified by HPLC.

The concentrate was lyophilized to obtain 31-O-demethyl-36,37-dihydro-FK506 represented by Formula 3 in the form of powder.

The prepared 31-O-demethyl-36,37-dihydro-FK506 was identified as follows. Specifically, high-performance liquid chromatography analysis, mass spectrometry, and nuclear magnetic resonance analysis were conducted. Analysis results of 31-O-demethyl-36,37-dihydro-FK506 are shown in Table 5 and FIGS. 13 to 18, and it was confirmed that 31-O-demethyl-36,37-dihydro-FK506 was produced by the constructed production strain *Streptomyces kanamyceticus* ΔfkbM,tcsD based on the results.

Analysis results of 31-O-demethyl-36,37-dihydro-FK506 (molecular formula: $C_{43}H_{69}NO_{12}$ and molecular weight: 792.02) are shown in Table 5 below.

TABLE 5

| Analysis method | Analysis results |
| --- | --- |
| High-performance liquid chromatography analysis | HPLC was performed using a 45-55% acetonitrile aqueous solution as a mobile phase at a flow rate of 1 mL/min and analyzed using a UV detector at 205 nm. In this regard, a retention time of 31-O-demethyl-36,37-dihydro-FK506 was 43 minutes. |

TABLE 5-continued

| | | Mass spectrometry | (ESI-HR-MS) Calcd. for $C_{43}H_{69}NNaO_{12}^+$: 814.4712, found: m/z 814.4715 | |
|---|---|---|---|---|
| | No. | carbon (ppm) | proton (ppm) | |
| Nuclear magnetic resonance analysis | 1 | 169.35 | | |
| | 2 | 56.64 | 4.58 (1H, br d, J = 5.0 Hz) | |
| | 3 | 27.92 | 2.05 (1H, m), 1.90 (1H, m) | |
| | 4 | 21.42 | 1.38 (1H, m), 1.74 (1H, m) | |
| | 5 | 24.80 | 1.51 (1H, m), 1.68 (1H, m) | |
| | 6 | 39.58 | 3.03 (1H, m), 4.44 (1H, m) | |
| | 7 | 165.08 | | |
| | 8 | 196.54 | | |
| | 9 | 97.42 | | |
| | 10 | 35.28 | 2.32 (1H, m) | |
| | 11 | 33.01 | 1.52 (1H, m), 2.16 (1H, m) | |
| | 12 | 74.03 | 3.39 (1H, m) | |
| | 13 | 73.22 | 3.68 (1H, dd, J = 10.0 Hz, 5.0 Hz) | |
| | 14 | 75.21 | 3.39 (1H, m) | |
| | 15 | 35.79 | 1.35 (1H, m), 1.56 (1H, m) | |
| | 16 | 26.67 | 1.66 (1H, m) | |
| | 17 | 49.02 | 1.80 (1H, m), 2.17 (1H, m) | |
| | 18 | 138.80 | | |
| | 19 | 123.64 | 5.03 (1H, d, J = 5.0 Hz) | |
| | 20 | 53.34 | 3.28 (1H, d, J = 5.0 Hz) | |
| | 21 | 213.76 | | |
| | 22 | 43.64 | 2.10 (1H, br d, J = 15 Hz), 2.77 (1H, br d, J = 15 Hz) | |
| | 23 | 70.36 | 3.92 (1H, m) | |
| | 24 | 39.97 | 1.89 (1H, m) | |
| | 25 | 77.82 | 5.33 (1H, br s) | |
| | 26 | 132.63 | | |
| | 27 | 130.03 | 5.09 (1H, d, J = 5.0 Hz) | |
| | 28 | 34.93 | 2.18 (1H, m) | |
| | 29 | 39.36 | 1.14 (1H, m), 1.91 (1H, m) | |
| | 30 | 75.79 | 3.59 (1H, m) | |
| | 31 | 75.58 | 3.36 (1H, m) | |
| | 32 | 32.36 | 1.35 (1H, m), 1.98 (1H, m) | |
| | 33 | 31.23 | 1.06 (1H, m), 1.61 (1H, m) | |
| | 34 | 33.34 | 1.42 (1H, m), 1.66 (1H, m) | |
| | 35 | 20.76 | 1.27 (2H, m) | |
| | 36 | 14.37 | 0.90 (3H, t, J = 7.5 Hz) | |
| | 37 | 16.54 | 1.00 (3H, d, J = 5 Hz) | |
| | 38 | 20.75 | 0.93 (3H, d, J = 5 Hz) | |
| | 39 | 16.18 | 1.59 (3H, s) | |
| | 40 | 9.79 | 0.87 (3H, d, J = 5 Hz) | |
| | 41 | 14.43 | 1.62 (3H, s) | |
| | 42 | 56.64 | 3.40 (3H, s) | |
| | 43 | 57.32 | 3.30 3H, s) | |

Based on $^1$H-NMR, $^{13}$C-NMR, and gHSQC results, the obtained compound consists of a total of 43 carbon atoms, and since a ketone carbon ($\delta_C$ 196.54) was additionally observed, and two methoxy groups were observed, it may be inferred that the compound was derived from 31-O-demethyl generated by the ΔfkbM gene. Based on gHMBC, it was confirmed that two methoxy hydrogens ($\delta_H$ 3.40 and 3.30) were correlated with C-15 ($\delta_C$ 75.21) and C-13 ($\delta_C$ 74.03), respectively. As a compound produced by the tcsD gene-deleted strain, 31-O-demethyl-35,37-dihydro-FK506 was determined to have a structure in which a double bond present between C-36/37 was reduced.

Example 4: Preparation of 9-deoxo-31-O-demethyl-36,37-dihydro-FK506

*Streptomyces kanamyceticus* ΔfkbD-fkbM,tcsD (accession number: KCTC13585BP), which is a 9-deoxo-31-O-demethyl-36,37-dihydro-FK506-producing strain, was constructed by inactivating fkbD-fkbM and tcsD genes of *Streptomyces kanamyceticus*, which is an FK506-producing strain, via an in-frame deletion caused by double cross-over homologous recombination, according to a method introduced by Ban, Y. H. et al., (*J. Nat. Prod.* 2013, 76, 1091-1098).

Specifically, in order to construct a mutant of the FK506-producing *Streptomyces kanamyceticus* strain from which fkbD-fkbM and tcsD genes were deleted, each gene was cloned to a pKC1139 vector and transferred to *Escherichia coli* ET12567/pUZ8002, and then the FK506-producing *Streptomyces kanamyceticus* strain was transformed with the vector by conjugation.

A method of constructing the strain may be explained more specifically as construction of an in-frame gene deletion plasmid and construction of a gene-deleted strain.

In the construction of the in-frame gene deletion plasmid, the *E. coli-Streptomyces* shuttle vector pKC1139 was used for in-frame gene deletion. Construction of the plasmid was performed by PCR of left- and right-flanking fragments of a target gene for deletion of Fosmid DNA derived from *Streptomyces kanamyceticus*. For deletion of the fkbD-fkbM gene, a primer pair of a left-flanking fragment, FkbD-MLF/FkbD-MLR, and a pair of a right-flanking fragment, FkbD-MRF/FkbD-MRR, were designed. For deletion of the tcsD gene, a primer pair of a left-flanking fragment, TcsDLF/TcsDLR, and a pair of a right-flanking fragment, TcsDRF/TcsDRR, were designed. All PCR fragments were isolated, digested with HindIII-XbaI or XbaI-EcoRI, and cloned to the pKC1139 vector. Information on the strains, plasmids, and primers used in this example are shown in Tables 1 and 2.

The plasmids used for construction of the gene-deleted strain are shown in Table 1. A plasmid for removing both C9 hydroxylase and 31-O-methyltransferase, pΔfkbD-fkbM, was transferred to *E. coli* ET12567/pUZ8002 and introduced into *Streptomyces kanamyceticus* by conjugation to delete the target gene by homologous recombination. A strain in which single cross-over occurred between the deletion plasmid and the chromosome of *Streptomyces kanamyceticus* was selected by culturing an apramycin-resistant transconjugant in the presence of apramycin at 37° C. (non-permissive temperature for replication of a pSG5-based replicon). Then, acquired colonies were proliferated three times at 28° C. without selection to allow second cross-over. The obtained double cross-over mutant, i.e., ΔfkbD-fkbM, was selected as a phenotype of apramycin sensitivity and identified by PCR, and optionally by Southern blotting.

The tcsD gene was deleted using the same method as that used in deletion of the fkbD-fkbM gene by introducing pΔtcsD into the constructed fkbD-fkbM gene-deleted *Streptomyces kanamyceticus* ΔfkbD-fkbM. ΔfkbD-fkbM,tcsD was selected as a phenotype of apramycin sensitivity and identified by PCR, and optionally by Southern blotting.

The constructed strain *Streptomyces kanamyceticus* ΔfkbD-fkbM,tcsD from which fkbD-fkbM and tcsD genes were deleted was deposited under the terms of the Budapest Treaty with the International Strain Depositary at the Korean Collection for Type Cultures (KCTC) of the Korea Research Institute of Bioscience and Biotechnology on Jul. 17, 2018 (accession number: KCTC13585BP).

9-Deoxo-31-O-demethyl-36,37-dihydro-FK506 was prepared by culturing the constructed production strain, *Streptomyces kanamyceticus* ΔfkbD-fkbM,tcsD (accession number: KCTC13585BP). This will be described in more detail. 50 mL of an R2YE medium (including 103 g/L sucrose, 10 g/L glucose, 0.25 g/L $K_2SO_4$, 10.12 g/L $MgCl_2 \cdot 6H_2O$, 0.1 g/L casamino acid, 50 mL/L yeast extract (10%), 100 mL/L TES buffer (5.73%, pH 7.2), 10 mL/L potassium phosphate (0.5%), 80 mL/L $CaCl_2 \cdot 2H_2O$ (3.68%), 15 mL/L L-proline (20%), 2 mL/L trace element solution, and 5 mL/L NaOH (1 N)) was added to a 250 mL baffled flask, and the production strain was inoculated thereinto. Then, the strain was pre-incubated in a rotary shaker incubator at 28° C. and 180 rpm for two days. Subsequently, 10 mL of the pre-incubated culture was inoculated into 1 L of the R2YE medium contained in a 3 L Erlenmeyer flask. After inoculation, the strain was incubated at 28° C. and 180 rpm for 6 days. After 6 days of the incubation, 9-deoxo-31-O-demethyl-36,37-dihydro-FK506 produced thereby was extracted by using a first extraction process.

The first extraction process was performed as follows. First, methanol was added to the culture broth in an equal volume and mixed for 30 minutes, and the microbial cells were removed by centrifugation, and then an extract from which the microbial cells were removed was concentrated using a rotary evaporator. After the concentrated extract was dissolved in water, ethyl acetate was added in twice the volume of the extract and mixed, and the mixture was left until layers were separated. After the layers were separated, an upper layer, i.e., an organic solvent layer, was recovered and concentrated using a rotary evaporator, and a weight after concentration was measured. The extract obtained by way of the first extraction process was passed through a column filled with silica gel. In this case, an amount of the silica gel was 15 times the weight of the extract obtained by way of the first extraction process, and methanol and methylene chloride mixed in five ratios (Aliquot 1. 0:100, Aliquot 2. 1:100, Aliquot 3. 1:10, Aliquot 4. 1:1, and Aliquot 5. 100:0) were used as mobile phases. In Aliquot 3, 9-deoxo-31-O-demethyl-36,37-dihydro-FK506 was confirmed. Aliquot 3 obtained as described above was concentrated using a rotary evaporator and ultimately purified by HPLC.

The concentrate was lyophilized to obtain 9-deoxo-31-O-demethyl-36,37-dihydro-FK506 represented by Formula 4 in the form of powder.

The prepared 9-deoxo-31-O-demethyl-36,37-dihydro-FK506 was identified as follows. Specifically, high-performance liquid chromatography analysis, mass spectrometry, and nuclear magnetic resonance analysis were conducted. Analysis results of 9-deoxo-31-O-demethyl-36,37-dihydro-FK506 are shown in Table 6 and FIGS. 19 to 24, and it was confirmed that 9-deoxo-31-O-demethyl-36,37-dihydro-FK506 was produced by the constructed production strain *Streptomyces kanamyceticus* ΔfkbD-fkbM,tcsD based on the results.

Analysis results of 9-deoxo-31-O-demethyl-36,37-dihydro-FK506 (molecular formula: $C_{43}H_{71}NO_{11}$ and molecular weight: 778.04) are shown in Table 6 below.

TABLE 6

| Analysis method | Analysis results |
| --- | --- |
| High-performance liquid chromatography analysis | HPLC was performed using a 45-55% acetonitrile aqueous solution as a mobile phase at a flow rate of 1 mL/min and analyzed using a UV detector at 205 nm. In this regard, a retention time of 9-deoxo-31-O-demethyl-36,37-dihydro-FK506 was 34 minutes. |

TABLE 6-continued

| | | | |
|---|---|---|---|
| Mass spectrometry | (ESI-HR-MS) Calcd. for $C_{43}H_{71}NNaO_{11}^+$: 800.4919, found: m/z 800.4924 | | |

| | No. | carbon (ppm) | proton (ppm) |
|---|---|---|---|
| Nuclear magnetic resonance analysis | 1 | 169.73 | |
| | 2 | 52.59 | 4.85 (1H, br d, J = 5.0 Hz) |
| | 3 | 26.94 | 1.70 (1H, m), 2.23 (1H, m) |
| | 4 | 21.03 | 1.32 (1H, m), 1.72 (1H, m) |
| | 5 | 24.77 | 1.52 (1H, m), 1.68 (1H, m) |
| | 6 | 42.97 | 3.19 (1H, m), 3.70 (1H, m) |
| | 7 | 174.37 | |
| | 8 | 37.54 | 2.49 (1H, d, J = 15.0 Hz), 2.67 (1H, d, J = 15.0 Hz) |
| | 9 | 98.85 | |
| | 10 | 38.78 | 1.56 (1H, m) |
| | 11 | 32.86 | 1.60 (1H, m), 1.94 (1H, m) |
| | 12 | 74.69 | 3.40 (1H, m) |
| | 13 | 70.99 | 3.84 (1H, dd, J = 10.0, 5.0 Hz) |
| | 14 | 77.21 | 3.53 (1H, m) |
| | 15 | 36.57 | 1.34 (1H, m), 1.47 (1H, m) |
| | 16 | 26.94 | 1.63 (1H, m) |
| | 17 | 48.49 | 1.64 (1H, m), 2.33 (1H, m) |
| | 18 | 141.15 | |
| | 19 | 122.53 | 5.05 (1H, d, J = 5.0 Hz) |
| | 20 | 53.84 | 3.20 (1H, d, J = 5.0 Hz) |
| | 21 | 215.35 | |
| | 22 | 42.20 | 2.20 (1H, br d, J = 15 Hz), 2.64 (1H, br d, J = 15 Hz) |
| | 23 | 69.96 | 3.97 (1H, m) |
| | 24 | 40.05 | 1.85 (1H, m) |
| | 25 | 76.90 | 5.20 (1H, br s) |
| | 26 | 132.82 | |
| | 27 | 129 | 4.97 (1H, d, J = 5.0 Hz) |
| | 28 | 35.29 | 2.32 (1H, m) |
| | 29 | 39.45 | 1.12 (1H, m), 1.88 (1H, m) |
| | 30 | 75.22 | 3.53 (1H, m) |
| | 31 | 75.22 | 3.40 (1H, m) |
| | 32 | 32.32 | 1.33 (1H, m), 1.95 (1H, m) |
| | 33 | 31.19 | 1.04 (1H, m), 1.59 (1H, m) |
| | 34 | 34.14 | 1.46 (1H, m), 1.62 (1H, m) |
| | 35 | 20.73 | 1.22 (2H, m) |
| | 36 | 14.25 | 0.88 (3H, t, J = 7.5 Hz) |
| | 37 | 17.22 | 0.94 (3H, d, J = 5 Hz) |
| | 38 | 19.17 | 0.76 (3H, d, J = 5 Hz) |
| | 39 | 15.82 | 1.63 (3H, s) |
| | 40 | 10.07 | 0.85 (3H, d, J = 5 Hz) |
| | 41 | 14.77 | 1.65 (3H, s) |
| | 42 | 56.45 | 3.35 (3H, s) |
| | 43 | 57.99 | 3.35 3H, s) |

Based on $^1$H-NMR, $^{13}$C-NMR, and gHSQC results, although the obtained compound consists of a total of 43 carbon atoms, CH$_2$ functional groups ($\delta_H$ 2.67, 2.49, and $\delta_C$ 37.54) were observed instead of ketone by influence of ΔfkbD as in substances 1 and 2. Based on analysis results of 2D-NMR data, the structure of the compound No. 4 was determined as 9-deoxo-31-O-demethyl-35,37-dihydro-FK506 produced from ΔfkbD-fkbM gene.

Example 5: Preparation of 9-deoxo-FK520

*Streptomyces kanamyceticus* ΔfkbD,tcsB (accession number: KCTC13579BP) or *Streptomyces kanamyceticus* ΔfkbD,tcsD (accession number: KCTC13580BP), which is a 9-deoxo-FK520-producing strain, was constructed by inactivating fkbD and tcsB genes or fkbD and tcsD genes of *Streptomyces kanamyceticus*, which is an FK506-producing strain, via an in-frame deletion caused by double cross-over homologous recombination, according to a method introduced by Ban, Y. H. et al., (*J. Nat. Prod.* 2013, 76, 1091-1098).

Specifically, in order to construct a mutant of the FK506-producing *Streptomyces kanamyceticus* strain from which fkbD and tcsB genes or fkbD and tcsD genes were deleted, each gene was cloned to a pKC1139 vector and transferred to *Escherichia coli* ET12567/pUZ8002, and then the FK506-producing *Streptomyces kanamyceticus* strain was transformed with the vector by conjugation.

A method of constructing the strain may be explained more specifically as construction of an in-frame gene deletion plasmid and construction of a gene-deleted strain.

In the construction of the in-frame gene deletion plasmid, the E. coli-Streptomyces shuttle vector pKC1139 was used for in-frame gene deletion. Construction of the plasmid was performed by PCR of left- and right-flanking fragments of a target gene for deletion of Fosmid DNA derived from Streptomyces kanamyceticus. For deletion of the fkbD gene, a primer pair of a left-flanking fragment, FkbDLF/FkbDLR, and a pair of a right-flanking fragment, FkbDRF/FkbDRR, were designed. For deletion of the tcsB gene, a primer pair of a left-flanking fragment, TcsBLF/TcsBLR, and a pair of a right-flanking fragment, TcsBRF/TcsBRR, were designed. For deletion of the tcsD gene, a primer pair of a left-flanking fragment, TcsDLF/TcsDLR, and a pair of a right-flanking fragment, TcsDRF/TcsDRR, were designed. All PCR fragments were isolated, digested with HindIII-XbaI or XbaI-EcoRI, and cloned to the pKC1139 vector. Information on the strains, plasmids, and primers used in this example are shown in Tables 1 and 2.

The plasmids used for construction of the gene-deleted strain are shown in Table 1. A plasmid for removing C9 hydroxylase, pΔfkbD, was transferred to E. coli ET12567/pUZ8002 and introduced into Streptomyces kanamyceticus by conjugation to delete the target gene by homologous recombination. A strain in which single cross-over occurred between the deletion plasmid and the chromosome of Streptomyces kanamyceticus was selected by culturing an apramycin-resistant transconjugant in the presence of apramycin at 37° C. (non-permissive temperature for replication of a pSG5-based replicon). Then, acquired colonies were proliferated three times at 28° C. without selection to allow second cross-over. The obtained double cross-over mutant, i.e., ΔfkbD, was selected as a phenotype of apramycin sensitivity and identified by PCR, and optionally by Southern blotting.

The tcsB gene or the tcsD gene was deleted using the same method as that used in deletion of the fkbD gene by introducing pΔtcsB or pΔtcsD into the constructed fkbD gene-deleted Streptomyces kanamyceticus ΔfkbD. ΔfkbD, tcsB or ΔfkbD,tcsD was selected as a phenotype of apramycin sensitivity and identified by PCR, and optionally by Southern blotting.

The constructed strain Streptomyces kanamyceticus ΔfkbD,tcsB from which fkbD and tcsB genes were deleted was deposited under the terms of the Budapest Treaty with the International Strain Depositary at the Korean Collection for Type Cultures (KCTC) of the Korea Research Institute of Bioscience and Biotechnology on Jul. 17, 2018 (accession number: KCTC13579BP), and the constructed strain Streptomyces kanamyceticus ΔfkbD,tcsD from which fkbD and tcsD genes were deleted was also deposited under the terms of the Budapest Treaty with the International Strain Depositary at the Korean Collection for Type Cultures (KCTC) of the Korea Research Institute of Bioscience and Biotechnology on Jul. 17, 2018 (accession number: KCTC13580BP).

9-Deoxo-FK520 was prepared by culturing the constructed production strain Streptomyces kanamyceticus ΔfkbD,tcsB (accession number: KCTC13579BP) or Streptomyces kanamyceticus ΔfkbD,tcsD (accession number: KCTC13580BP). This will be described in more detail. 50 mL of an R2YE medium (including 103 g/L sucrose, 10 g/L glucose, 0.25 g/L $K_2SO_4$, 10.12 g/L $MgCl_2 \cdot 6H_2O$, 0.1 g/L casamino acid, 50 mL/L yeast extract (10%), 100 mL/L TES buffer (5.73%, pH 7.2), 10 mL/L potassium phosphate (0.5%), 80 mL/L $CaCl_2 \cdot 2H_2O$ (3.68%), 15 mL/L L-proline (20%), 2 mL/L trace element solution, and 5 mL/L NaOH (1 N)) was added to a 250 mL baffled flask, and the production strain was inoculated thereinto. Then, the strain was pre-incubated in a rotary shaker incubator at 28° C. and 180 rpm for two days. Subsequently, 10 mL of the pre-incubated culture was inoculated into 1 L of the R2YE medium contained in a 3 L Erlenmeyer flask. After inoculation, the strain was incubated at 28° C. and 180 rpm for 6 days. After 6 days of the incubation, 9-deoxo-FK520 produced thereby was extracted by using a first extraction process.

The first extraction process was performed as follows. First, methanol was added to the culture broth in an equal volume and mixed for 30 minutes, and the microbial cells were removed by centrifugation, and then an extract from which the microbial cells were removed was concentrated using a rotary evaporator. After the concentrated extract was dissolved in water, ethyl acetate was added in twice the volume of the extract and mixed, and the mixture was left until layers were separated. After the layers were separated, an upper layer, i.e., an organic solvent layer, was recovered and concentrated using a rotary evaporator, and a weight after concentration was measured. The extract obtained by way of the first extraction process was passed through a column filled with silica gel. In this case, an amount of the silica gel was 15 times the weight of the extract obtained by way of the first extraction process, and methanol and methylene chloride mixed in five ratios (Aliquot 1. 0:100, Aliquot 2. 1:100, Aliquot 3. 1:10, Aliquot 4. 1:1, and Aliquot 5. 100:0) were used as mobile phases. In Aliquot 3, 9-deoxo-FK520 was confirmed. Aliquot 3 obtained as described above was concentrated using a rotary evaporator and ultimately purified by HPLC.

The concentrate was lyophilized to obtain 9-deoxo-FK520 represented by Formula 5 in the form of powder.

The prepared 9-deoxo-FK520 was identified as follows. Specifically, high-performance liquid chromatography analysis, mass spectrometry, and nuclear magnetic resonance analysis were conducted. Analysis results of 9-deoxo-FK520 are shown in Table 7 and FIGS. 25 to 30, and it was confirmed that 9-deoxo-FK520 was produced by the constructed production strain Streptomyces kanamyceticus ΔfkbD,tcsB or Streptomyces kanamyceticus ΔfkbD,tcsD based on the results.

Analysis results of 9-deoxo-FK520 (molecular formula: $C_{43}H_{71}NO_{11}$ and molecular weight: 778.04) are shown in Table 7 below.

TABLE 7

| Analysis method | Analysis results |
|---|---|
| High-performance liquid chromatography analysis | HPLC was performed using a 45-55% acetonitrile aqueous solution as a mobile phase at a flow rate of 1 mL/min and analyzed using a UV detector at 205 nm. In this regard, a retention time of 9-deoxo-31-O-demethyl-36,37-dihydro-FK506 was 34 minutes. |

TABLE 7-continued

| | | No. | carbon (ppm) | proton (ppm) |
|---|---|---|---|---|
| Mass spectrometry | | (ESI-HR-MS) Calcd. for $C_{43}H_{71}NNaO_{11}^+$: 800.4919, found: m/z 800.4924 | | |
| Nuclear magnetic resonance analysis | | 1 | 169.73 | |
| | | 2 | 52.59 | 4.85 (1H, br d, J = 5.0 Hz) |
| | | 3 | 26.94 | 1.70 (1H, m), 2.23 (1H, m) |
| | | 4 | 21.03 | 1.32 (1H, m), 1.72 (1H, m) |
| | | 5 | 24.77 | 1.52 (1H, m), 1.68 (1H, m) |
| | | 6 | 42.97 | 3.19 (1H, m), 3.70 (1H, m) |
| | | 7 | 174.37 | |
| | | 8 | 37.54 | 2.49 (1H, d, J = 15.0 Hz), 2.67 (1H, d, J = 15.0 Hz) |
| | | 9 | 98.85 | |
| | | 10 | 38.78 | 1.56 (1H, m) |
| | | 11 | 32.86 | 1.60 (1H, m), 1.94 (1H, m) |
| | | 12 | 74.69 | 3.40 (1H, m) |
| | | 13 | 70.99 | 3.84 (1H, dd, J = 10.0 Hz, 5.0 Hz) |
| | | 14 | 77.21 | 3.53 (1H, m) |
| | | 15 | 36.57 | 1.34 (1H, m), 1.47 (1H, m) |
| | | 16 | 26.94 | 1.63 (1H, m) |
| | | 17 | 48.49 | 1.64 (1H, m), 2.33 (1H, m) |
| | | 18 | 141.15 | |
| | | 19 | 122.53 | 5.05 (1H, d, J = 5.0 Hz) |
| | | 20 | 53.84 | 3.20 (1H, d, J = 5.0 Hz) |
| | | 21 | 215.35 | |
| | | 22 | 42.20 | 2.20 (1H, br d, J = 15 Hz), 2.64 (1H, br d, J = 15 Hz) |
| | | 23 | 69.96 | 3.97 (1H, m) |
| | | 24 | 40.05 | 1.85 (1H, m) |
| | | 25 | 76.90 | 5.20 (1H, br s) |
| | | 26 | 132.82 | |
| | | 27 | 129 | 4.97 (1H, d, J = 5.0 Hz) |
| | | 28 | 35.29 | 2.32 (1H, m) |
| | | 29 | 39.45 | 1.12 (1H, m), 1.88 (1H, m) |
| | | 30 | 75.22 | 3.53 (1H, m) |
| | | 31 | 75.22 | 3.40 (1H, m) |
| | | 32 | 32.32 | 1.33 (1H, m), 1.95 (1H, m) |
| | | 33 | 31.19 | 1.04 (1H, m), 1.59 (1H, m) |
| | | 34 | 34.14 | 1.46 (1H, m), 1.62 (1H, m) |
| | | 35 | 20.73 | 1.22 (2H, m) |
| | | 36 | 14.25 | 0.88 (3H, t, J = 7.5 Hz) |
| | | 37 | 17.22 | 0.94 (3H, d, J = 5 Hz) |
| | | 38 | 19.17 | 0.76 (3H, d, J = 5 Hz) |
| | | 39 | 15.82 | 1.63 (3H, s) |
| | | 40 | 10.07 | 0.85 (3H, d, J = 5 Hz) |
| | | 41 | 14.77 | 1.65 (3H, s) |
| | | 42 | 56.45 | 3.35 (3H, s) |
| | | 43 | 57.99 | 3.35 (3H, s) |

Based on $^1$H-NMR, $^{13}$C-NMR, and gHSQC data, although the compound consisting of a total of 43 carbon atoms was similar to 9-deoxo-31-O-demethyl-36,37-dihydro-FK506, the compound was confirmed as a structural isomer since a methoxy group ($\delta_H$ 3.41 and $\delta_C$ 56.81) was additionally observed, and one fewer $CH_2$ functional group was observed. As a result of identifying proton coupling by gCOSY, it was confirmed that the compound had a pipecolyl backbone based on couplings of H-2 to H-5. Based on the methyl group in which the triplet couplings are observed from gHMBC, and the $CH_2$ group ($\delta_H$ 1.72 and 1.52, and $\delta_C$ 20.41) which is formed by the correlation between C-21 ($\delta_H$ 1.72 and 1.52, and $\delta_C$ 20.41), it was confirmed that an ethyl group constituting FK520, not a propyl group of FK506, was present at C-21. Based thereon, the structure of the compound No. 5 was determined as 9-deoxo-FK520.

Example 6: Preparation of 31-O-demethyl-FK520

*Streptomyces kanamyceticus* ΔfkbM,tcsB (accession number: KCTC13583BP) or *Streptomyces kanamyceticus* ΔfkbM,tcsD (accession number: KCTC13584BP), which is a 31-O-demethyl-FK520-producing strain, was constructed by inactivating fkbM and tcsB genes or fkbM and tcsD genes of *Streptomyces kanamyceticus*, which is an FK506-producing strain, via an in-frame deletion caused by double cross-over homologous recombination, according to a method introduced by Ban, Y. H. et al., (*J. Nat. Prod.* 2013, 76, 1091-1098).

Specifically, in order to construct a mutant of the FK506-producing *Streptomyces kanamyceticus* strain from which fkbM and tcsB genes or fkbM and tcsD genes were deleted, each gene was cloned to a pKC1139 vector and transferred to *Escherichia coli* ET12567/pUZ8002, and then the FK506-producing *Streptomyces kanamyceticus* strain was transformed with the vector by conjugation.

A method of constructing the strain may be explained more specifically as construction of an in-frame gene deletion plasmid and construction of a gene-deleted strain.

In the construction of the in-frame gene deletion plasmid, the *E. coli-Streptomyces* shuttle vector pKC1139 was used for in-frame gene deletion. Construction of the plasmid was performed by PCR of left- and right-flanking fragments of a target gene for deletion of Fosmid DNA derived from *Streptomyces kanamyceticus*. For deletion of the fkbM gene, a primer pair of a left-flanking fragment, FkbMLF/FkbMLR, and a pair of a right-flanking fragment, FkbMRF/FkbMRR, were designed. For deletion of the tcsB gene, a primer pair of a left-flanking fragment, TcsBLF/TcsBLR, and a pair of a right-flanking fragment, TcsBRF/TcsBRR, were designed. For deletion of the tcsD gene, a primer pair of a left-flanking fragment, TcsDLF/TcsDLR, and a pair of a right-flanking fragment, TcsDRF/TcsDRR, were designed. All PCR fragments were isolated, digested with HindIII-XbaI or XbaI-EcoRI, and cloned to the pKC1139 vector. Information on the strains, plasmids, and primers used in this example are shown in Tables 1 and 2.

The plasmids used for construction of the gene-deleted strain are shown in Table 1. A plasmid for removing 31-O-methyltransferase, pΔfkbM, was transferred to *E. coli* ET12567/pUZ8002 and introduced into *Streptomyces kanamyceticus* by conjugation to delete the target gene by homologous recombination. A strain in which single crossover occurred between the deletion plasmid and the chromosome of *Streptomyces kanamyceticus* was selected by culturing an apramycin-resistant transconjugant in the presence of apramycin at 37° C. (non-permissive temperature for replication of a pSG5-based replicon). Then, acquired colonies were proliferated three times at 28° C. without selection to allow second cross-over. The obtained double cross-over mutant, i.e., ΔfkbM, was selected as a phenotype of apramycin sensitivity and identified by PCR, and optionally by Southern blotting.

The tcsB gene or the tcsD gene was deleted using the same method as that used in deletion of the fkbM gene by introducing pΔtcsB or pΔtcsD into the constructed fkbM gene-deleted *Streptomyces kanamyceticus* ΔfkbM. ΔfkbM, tcsB or ΔfkbM,tcsD was selected as a phenotype of apramycin sensitivity and identified by PCR, and optionally by Southern blotting.

The constructed strain *Streptomyces kanamyceticus* ΔfkbM,tcsB from which fkbM and tcsB genes were deleted was deposited under the terms of the Budapest Treaty with the International Strain Depositary at the Korean Collection for Type Cultures (KCTC) of the Korea Research Institute of Bioscience and Biotechnology on Jul. 17, 2018 (accession number: KCTC13583BP), and the constructed strain *Streptomyces kanamyceticus* ΔfkbM,tcsD from which fkbM and tcsD genes were deleted was also deposited under the terms of the Budapest Treaty with the International Strain Depositary at the Korean Collection for Type Cultures (KCTC) of the Korea Research Institute of Bioscience and Biotechnology on Jul. 17, 2018 (accession number: KCTC13584BP).

31-O-Demethyl-FK520 was prepared by culturing the constructed production strain *Streptomyces kanamyceticus* ΔfkbM,tcsB (accession number: KCTC13583BP) or *Streptomyces kanamyceticus* ΔfkbM,tcsD (accession number: KCTC13584BP). This will be described in more detail. 50 mL of an R2YE medium (including 103 g/L sucrose, 10 g/L glucose, 0.25 g/L $K_2SO_4$, 10.12 g/L $MgCl_2·6H_2O$, 0.1 g/L casamino acid, 50 mL/L yeast extract (10%), 100 mL/L TES buffer (5.73%, pH 7.2), 10 mL/L potassium phosphate (0.5%), 80 mL/L $CaCl_2·2H_2O$ (3.68%), 15 mL/L L-proline (20%), 2 mL/L trace element solution, and 5 mL/L NaOH (1 N)) was added to a 250 mL baffled flask, and the production strain was inoculated thereinto. Then, the strain was pre-incubated in a rotary shaker incubator at 28° C. and 180 rpm for two days. Subsequently, 10 mL of the pre-incubated culture was inoculated into 1 L of the R2YE medium contained in a 3 L Erlenmeyer flask. After inoculation, the strain was incubated at 28° C. and 180 rpm for 6 days. After 6 days of the incubation, 31-O-demethyl-FK520 produced thereby was extracted by using a first extraction process.

The first extraction process was performed as follows. First, methanol was added to the culture broth in an equal volume and mixed for 30 minutes, and the microbial cells were removed by centrifugation, and then an extract from which the microbial cells were removed was concentrated using a rotary evaporator. After the concentrated extract was dissolved in water, ethyl acetate was added in twice the volume of the extract and mixed, and the mixture was left until layers were separated. After the layers were separated, an upper layer, i.e., an organic solvent layer, was recovered and concentrated using a rotary evaporator, and a weight after concentration was measured. The extract obtained by way of the first extraction process was passed through a column filled with silica gel. In this case, an amount of the silica gel was 15 times the weight of the extract obtained by way of the first extraction process, and methanol and methylene chloride mixed in five ratios (Aliquot 1. 0:100, Aliquot 2. 1:100, Aliquot 3. 1:10, Aliquot 4. 1:1, and Aliquot 5. 100:0) were used as mobile phases. In Aliquot 3, 31-O-demethyl-FK520 was confirmed. Aliquot 3 obtained as described above was concentrated using a rotary evaporator and ultimately purified by HPLC.

The concentrate was lyophilized to obtain 31-O-demethyl-FK520 represented by Formula 6 in the form of powder.

The prepared 31-O-demethyl-FK520 was identified as follows. Specifically, high-performance liquid chromatography analysis, mass spectrometry, and nuclear magnetic resonance analysis were conducted. Analysis results of 31-O-demethyl-FK520 are shown in Table 8 and FIGS. 31 to 36, and it was confirmed that 31-O-demethyl-FK520 was produced by the constructed production strain *Streptomyces kanamyceticus* ΔfkbM,tcsB or *Streptomyces kanamyceticus* ΔfkbM,tcsD based on the results.

Analysis results of 31-O-demethyl-FK520 (molecular formula: $C_{42}H_{67}NO_{12}$ and molecular weight: 777.99) are shown in Table 8 below.

TABLE 8

| Analysis method | Analysis results |
| --- | --- |
| High-performance liquid chromatography analysis | HPLC was performed using a 45-55% acetonitrile aqueous solution as a mobile phase at a flow rate of 1 mL/min and analyzed using a UV detector at 205 nm. In this regard, a retention time of 31-O-demethyl-FK520 was 34 minutes. |

TABLE 8-continued

| | | | |
|---|---|---|---|
| Mass spectrometry | (ESI-HR-MS) Calcd. for $C_{42}H_{67}NNaO_{12}^{+}$: 800.4555, found: m/z 800.4561 | | |

| | No. | carbon (ppm) | proton (ppm) |
|---|---|---|---|
| Nuclear magnetic resonance analysis | 1 | 169.30 | |
| | 2 | 56.64 | 4.58 (1H, br d, J = 5.0 Hz) |
| | 3 | 27.92 | 2.05 (1H, m), 1.90 (1H, m) |
| | 4 | 21.42 | 1.38 (1H, m), 1.74 (1H, m) |
| | 5 | 24.54 | 1.51 (1H, m), 1.68 (1H, m) |
| | 6 | 39.58 | 3.03 (1H, m), 4.42 (1H, m) |
| | 7 | 165.03 | |
| | 8 | 196.50 | |
| | 9 | 97.36 | |
| | 10 | 35.28 | 2.32 (1H, m) |
| | 11 | 33.01 | 1.52 (1H, m), 2.16 (1H, m) |
| | 12 | 73.92 | 3.39 (1H, m) |
| | 13 | 73.09 | 3.68 (1H, dd, J = 10.0 Hz, 5.0 Hz) |
| | 14 | 75.06 | 3.42 (1H, m) |
| | 15 | 35.79 | 1.35 (1H, m), 1.56 (1H, m) |
| | 16 | 26.67 | 1.66 (1H, m) |
| | 17 | 49.02 | 1.80 (1H, m), 2.17 (1H, m) |
| | 18 | 138.99 | |
| | 19 | 123.33 | 5.01 (1H, d, J = 5.0 Hz) |
| | 20 | 53.34 | 3.28 (1H, d, J = 5.0 Hz) |
| | 21 | 213.69 | |
| | 22 | 43.64 | 2.10 (1H, br d, J = 15 Hz), 2.77 (1H, br d, J = 15 Hz) |
| | 23 | 70.22 | 3.92 (1H, m) |
| | 24 | 39.97 | 1.89 (1H, m) |
| | 25 | 77.80 | 5.33 (1H, br s) |
| | 26 | 132.47 | |
| | 27 | 130.07 | 5.09 (1H, d, J = 5.0 Hz) |
| | 28 | 34.93 | 2.18 (1H, m) |
| | 29 | 39.36 | 1.14 (1H, m), 1.91 (1H, m) |
| | 30 | 75.64 | 3.57 (1H, m) |
| | 31 | 75.50 | 3.36 (1H, m) |
| | 32 | 32.36 | 1.35 (1H, m), 1.98 (1H, m) |
| | 33 | 31.23 | 1.06 (1H, m), 1.61 (1H, m) |
| | 34 | 24.78 | 1.45 (1H, m), 1.72 (1H, m) |
| | 35 | 11.91 | 0.86 (3H, t, J = 7.5 Hz) |
| | 36 | 16.41 | 0.99 (3H, d, J = 5 Hz) |
| | 37 | 20.66 | 0.93 (3H, d, J = 5 Hz) |
| | 38 | 16.02 | 1.59 (3H, s) |
| | 39 | 9.71 | 0.90 (3H, d, J = 5 Hz) |
| | 40 | 14.20 | 1.62 (3H, s) |
| | 41 | 56.55 | 3.38 (3H, s) |
| | 42 | 57.22 | 3.30 3H, s) |

Although compound No. 6 has a molecular weight of 800.4563, which is very similar to molecular weights of 800.4924 and 800.4927, it was confirmed that the compound consisting of a total of 42 carbon atoms had one carbon-atom difference due to one fewer methoxy group based on $^1$H-NMR, $^{13}$C-NMR, and gHSQC data, and a ketone carbon ($\delta_C$ 196.50) was observed. Based on 2D-NMR data, the structure of the compound was determined as 31-O-demethyl-FK520.

Example 7: Preparation of 9-deoxo-31-O-demethyl-FK520

*Streptomyces kanamyceticus* ΔfkbD-fkbM,tcsB (accession number: KCTC13582BP) or *Streptomyces kanamyceticus* ΔfkbD-fkbM,tcsD (accession number: KCTC13585BP), which is a 9-deoxo-31-O-demethyl-FK520-producing strain, was constructed by inactivating fkbD-fkbM and tcsB genes or fkbD-fkbM and tcsD genes of *Streptomyces kanamyceticus*, which is an FK506-producing strain, via an in-frame deletion caused by double cross-over homologous recombination, according to a method introduced by Ban, Y. H. et al., (*J. Nat. Prod.* 2013, 76, 1091-1098).

Specifically, in order to construct a mutant of the FK506-producing *Streptomyces kanamyceticus* strain from which fkbD-fkbM and tcsB genes or fkbD-fkbM and tcsD genes were deleted, each gene was cloned to a pKC1139 vector and transferred to *Escherichia coli* ET12567/pUZ8002, and then the FK506-producing *Streptomyces kanamyceticus* strain was transformed with the vector by conjugation.

A method of constructing the strain may be explained more specifically as construction of an in-frame gene deletion plasmid and construction of a gene-deleted strain.

In the construction of the in-frame gene deletion plasmid, the *E. coli-Streptomyces* shuttle vector pKC1139 was used for in-frame gene deletion. Construction of the plasmid was performed by PCR of left- and right-flanking fragments of a target gene for deletion of Fosmid DNA derived from *Streptomyces kanamyceticus*. For deletion of the fkbD-fkbM gene, a primer pair of a left-flanking fragment, FkbD-MLF/FkbD-MLR, and a pair of a right-flanking fragment, FkbD-MRF/FkbD-MRR, were designed. For deletion of the tcsB gene, a primer pair of a left-flanking fragment, TcsBLF/TcsBLR, and a pair of a right-flanking fragment, TcsBRF/TcsBRR, were designed. For deletion of the tcsD gene, a primer pair of a left-flanking fragment, TcsDLF/TcsDLR, and a pair of a right-flanking fragment, TcsDRF/TcsDRR, were designed. All PCR fragments were isolated, digested with HindIII-XbaI or XbaI-EcoRI, and cloned to the pKC1139 vector. Information on the strains, plasmids, and primers used in this example are shown in Tables 1 and 2.

The plasmids used for construction of the gene-deleted strain are shown in Table 1. A plasmid for removing both C9 hydroxylase and 31-O-methyltransferase, pΔfkbD-fkbM, was transferred to *E. coli* ET12567/pUZ8002 and introduced into *Streptomyces kanamyceticus* by conjugation to delete the target gene by homologous recombination. A strain in which single cross-over occurred between the deletion plasmid and the chromosome of *Streptomyces kanamyceticus* was selected by culturing an apramycin-resistant transconjugant in the presence of apramycin at 37° C. (non-permissive temperature for replication of a pSG5-based replicon). Then, acquired colonies were proliferated three times at 28° C. without selection to allow second cross-over. The obtained double cross-over mutant, i.e., ΔfkbD-fkbM, was selected as a phenotype of apramycin sensitivity and identified by PCR, and optionally by Southern blotting.

The tcsB gene or tcsD gene was deleted using the same method as that used in deletion of the fkbD-fkbM gene by introducing pΔtcsB or pΔtcsD into the constructed fkbD-fkbM gene-deleted *Streptomyces kanamyceticus* ΔfkbD-fkbM. ΔfkbD-fkbM,tcsB or ΔfkbD-fkbM,tcsD was selected as a phenotype of apramycin sensitivity and identified by PCR, and optionally by Southern blotting.

The constructed strain *Streptomyces kanamyceticus* ΔfkbD-fkbM,tcsB from which fkbD-fkbM and tcsB genes were deleted was deposited under the terms of the Budapest Treaty with the International Strain Depositary at the Korean Collection for Type Cultures (KCTC) of the Korea Research Institute of Bioscience and Biotechnology on Jul. 17, 2018 (accession number: KCTC13582BP), and the constructed strain *Streptomyces kanamyceticus* ΔfkbD-fkbM,tcsD from which fkbD-fkbM and tcsD genes were deleted was also deposited under the terms of the Budapest Treaty with the International Strain Depositary at the Korean Collection for Type Cultures (KCTC) of the Korea Research Institute of Bioscience and Biotechnology on Jul. 17, 2018 (accession number: KCTC13585BP).

9-Deoxo-31-O-demethyl-FK520 was prepared by culturing the constructed production strain *Streptomyces kanamyceticus* ΔfkbD-fkbM,tcsB (accession number: KCTC13582BP) or *Streptomyces kanamyceticus* ΔfkbD-fkbM,tcsD (accession number: KCTC13585BP). This will be described in more detail. 50 mL of an R2YE medium (including 103 g/L sucrose, 10 g/L glucose, 0.25 g/L $K_2SO_4$, 10.12 g/L $MgCl_2 \cdot 6H_2O$, 0.1 g/L casamino acid, 50 mL/L yeast extract (10%), 100 mL/L TES buffer (5.73%, pH 7.2), 10 mL/L potassium phosphate (0.5%), 80 mL/L $CaCl_2 \cdot 2H_2O$ (3.68%), 15 mL/L L-proline (20%), 2 mL/L trace element solution, and 5 mL/L NaOH (1 N)) was added to a 250 mL baffled flask, and the production strain was inoculated thereinto. Then, the strain was pre-incubated in a rotary shaker incubator at 28° C. and 180 rpm for two days. Subsequently, 10 mL of the pre-incubated culture was inoculated into 1 L of the R2YE medium contained in a 3 L Erlenmeyer flask. After inoculation, the strain was incubated at 28° C. and 180 rpm for 6 days. After 6 days of the incubation, 9-deoxo-31-O-demethyl-FK520 produced thereby was extracted by using a first extraction process.

The first extraction process was performed as follows. First, methanol was added to the culture broth in an equal volume and mixed for 30 minutes, and the microbial cells were removed by centrifugation, and then an extract from which the microbial cells were removed was concentrated using a rotary evaporator. After the concentrated extract was dissolved in water, ethyl acetate was added in twice the volume of the extract and mixed, and the mixture was left until layers were separated. After the layers were separated, an upper layer, i.e., an organic solvent layer, was recovered and concentrated using a rotary evaporator, and a weight after concentration was measured. The extract obtained by way of the first extraction process was passed through a column filled with silica gel. In this case, an amount of the silica gel was 15 times the weight of the extract obtained by way of the first extraction process, and methanol and methylene chloride mixed in five ratios (Aliquot 1. 0:100, Aliquot 2. 1:100, Aliquot 3. 1:10, Aliquot 4. 1:1, and Aliquot 5. 100:0) were used as mobile phases. In Aliquot 3, 9-deoxo-31-O-demethyl-FK520 was confirmed. Aliquot 3 obtained as described above was concentrated using a rotary evaporator and ultimately purified by HPLC.

The concentrate was lyophilized to obtain 9-deoxo-31-O-demethyl-FK520 represented by Formula 7 in the form of powder.

The prepared 9-deoxo-31-O-demethyl-FK520 was identified as follows. Specifically, high-performance liquid chromatography analysis, mass spectrometry, and nuclear magnetic resonance analysis were conducted. Analysis results of 9-deoxo-31-O-demethyl-FK520 are shown in Table 9 and FIGS. 37 to 42, and it was confirmed that 9-deoxo-31-O-demethyl-FK520 was produced by the constructed production strain *Streptomyces kanamyceticus* fkbD-fkbM,tcsB or *Streptomyces kanamyceticus* ΔfkbD-fkbM,tcsD based on the results.

Analysis results of 9-deoxo-31-O-demethyl-FK520 (molecular formula: $C_{42}H_{69}NO_{11}$ and molecular weight: 764.01) are shown in Table 9 below.

TABLE 9

| Analysis method | Analysis results |
| --- | --- |
| High-performance liquid chromatography analysis | HPLC was performed using a 45-55% acetonitrile aqueous solution as a mobile phase at a flow rate of 1 mL/min and analyzed using a UV detector at 205 nm. In this regard, a retention time of 9-deoxo-31-O-demethyl-FK520 was 24 minutes. |

TABLE 9-continued

| | | | |
|---|---|---|---|
| Mass spectrometry | | (ESI-HR-MS) Calcd. for $C_{42}H_{69}NNaO_{11}^{+}$: 786.4763, found: m/z 786.4769 | |

| | No. | carbon (ppm) | proton (ppm) |
|---|---|---|---|
| Nuclear magnetic resonance analysis | 1 | 169.65 | |
| | 2 | 52.86 | 4.87 (1H, br d, J = 5.0 Hz) |
| | 3 | 26.86 | 1.70 (1H, m), |
| | | | 2.23 (1H, m) |
| | 4 | 20.95 | 1.32 (1H, m), |
| | | | 1.72 (1H, m) |
| | 5 | 24.69 | 1.52 (1H, m), |
| | | | 1.68 (1H, m) |
| | 6 | 42.97 | 3.19 (1H, m), |
| | | | 3.70 (1H, m) |
| | 7 | 174.27 | |
| | 8 | 37.54 | 2.49 (1H, d, J = 15.0 Hz), |
| | | | 2.67 (1H, d, J = 15.0 Hz) |
| | 9 | 98.76 | |
| | 10 | 38.78 | 1.56 (1H, m) |
| | 11 | 32.86 | 1.60 (1H, m), |
| | | | 1.94 (1H, m) |
| | 12 | 74.61 | 3.41 (1H, m) |
| | 13 | 70.92 | 3.86 (1H, dd, J = 10.0 Hz, 5.0 Hz) |
| | 14 | 77.21 | 3.53 (1H, m) |
| | 15 | 36.57 | 1.34 (1H, m), |
| | | | 1.47 (1H, m) |
| | 16 | 25.93 | 1.63 (1H, m) |
| | 17 | 48.49 | 1.64 (1H, m), |
| | | | 2.33 (1H, m) |
| | 18 | 141.30 | |
| | 19 | 122.26 | 5.05 (1H, d, J = 5.0 Hz) |
| | 20 | 55.66 | 3.20 (1H, d, J = 5.0 Hz) |
| | 21 | 215.35 | |
| | 22 | 42.20 | 2.20 (1H, br d, J = 15 Hz), |
| | | | 2.64 (1H, br d, J = 15 Hz) |
| | 23 | 69.82 | 3.98 (1H, m) |
| | 24 | 40.05 | 1.85 (1H, m) |
| | 25 | 76.90 | 5.20 (1H, br s) |
| | 26 | 132.76 | |
| | 27 | 128.90 | 4.97 (1H, d, J = 5.0 Hz) |
| | 28 | 35.29 | 2.32 (1H, m) |
| | 29 | 39.45 | 1.12 (1H, m), |
| | | | 1.88 (1H, m) |
| | 30 | 75.22 | 3.53 (1H, m) |
| | 31 | 75.22 | 3.40 (1H, m) |
| | 32 | 32.32 | 1.33 (1H, m), |
| | | | 1.95 (1H, m) |
| | 33 | 31.19 | 1.04 (1H, m), |
| | | | 1.59 (1H, m) |
| | 34 | 25.13 | 1.52 (1H, m), |
| | | | 1.68 (1H, m) |
| | 35 | 12.00 | 0.88 (3H, t, J = 7.5 Hz) |
| | 36 | 17.14 | 0.95 (3H, d, J = 5 Hz) |
| | 37 | 19.09 | 0.77 (3H, d, J = 5 Hz) |
| | 38 | 15.77 | 1.65 (3H, s) |
| | 39 | 9.98 | 0.86 (3H, d, J = 5 Hz) |
| | 40 | 14.68 | 1.67 (3H, s) |
| | 41 | 56.37 | 3.38 (3H, s) |
| | 42 | 57.91 | 3.39 3H, s) |

Based on $^1$H-NMR, $^{13}$C-NMR, and gHSQC data, although the obtained compound consisting of a total of 42 carbon atoms exhibited similar results to those of 31-O-demethyl-FK520, a $CH_2$ functional group ($\delta_H$ 2.67 and 2.49 and $\delta_C$ 37.54) generated from the ΔfkbD-fkbM gene was observed. Based on 2D-NMR data, the structure of the compound No. 7 was determined as 9-deoxo-31-O-demethyl-FK520.

Example 8: Preparation of 9-deoxo-FK523

*Streptomyces kanamyceticus* ΔfkbD,tcsB (accession number: KCTC13579BP), which is a 9-deoxo-FK523-producing strain, was constructed by inactivating fkbD and tcsB genes of *Streptomyces kanamyceticus*, which is an FK506-producing strain, via an in-frame deletion caused by double cross-over homologous recombination, according to a method introduced by Ban, Y. H. et al., (*J. Nat. Prod.* 2013, 76, 1091-1098).

Specifically, in order to construct a mutant of the FK506-producing *Streptomyces kanamyceticus* strain from which fkbD and tcsB genes were deleted, each gene was cloned to a pKC1139 vector and transferred to *Escherichia coli* ET12567/pUZ8002, and then the FK506-producing *Streptomyces kanamyceticus* strain was transformed with the vector by conjugation.

A method of constructing the strain may be explained more specifically as construction of an in-frame gene deletion plasmid and construction of a gene-deleted strain.

In the construction of the in-frame gene deletion plasmid, the E. coli-Streptomyces shuttle vector pKC1139 was used for in-frame gene deletion. Construction of the plasmid was performed by PCR of left- and right-flanking fragments of a target gene for deletion of Fosmid DNA derived from Streptomyces kanamyceticus. For deletion of the fkbD gene, a primer pair of a left-flanking fragment, FkbDLF/FkbDLR, and a pair of a right-flanking fragment, FkbDRF/FkbDRR, were designed. For deletion of the tcsB gene, a primer pair of a left-flanking fragment, TcsBLF/TcsBLR, and a pair of a right-flanking fragment, TcsBRF/TcsBRR, were designed. All PCR fragments were isolated, digested with HindIII-XbaI or XbaI-EcoRI, and cloned to the pKC1139 vector. Information on the strains, plasmids, and primers used in this example are shown in Tables 1 and 2.

The plasmids used for construction of the gene-deleted strain are shown in Table 1. A plasmid for removing C9 hydroxylase, pΔfkbD, was transferred to E. coli ET12567/pUZ8002 and introduced into Streptomyces kanamyceticus by conjugation to delete the target gene by homologous recombination. A strain in which single cross-over occurred between the deletion plasmid and the chromosome of Streptomyces kanamyceticus was selected by culturing an apramycin-resistant transconjugant in the presence of apramycin at 37° C. (non-permissive temperature for replication of a pSG5-based replicon). Then, acquired colonies were proliferated three times at 28° C. without selection to allow second cross-over. The obtained double cross-over mutant, i.e., ΔfkbD, was selected as a phenotype of apramycin sensitivity and identified by PCR, and optionally by Southern blotting.

The tcsB gene was deleted using the same method as that used in deletion of the fkbD gene by introducing pΔtcsB into the constructed fkbD gene-deleted Streptomyces kanamyceticus ΔfkbD. ΔfkbD,tcsB was selected as a phenotype of apramycin sensitivity and identified by PCR, and optionally by Southern blotting.

The constructed strain Streptomyces kanamyceticus ΔfkbD,tcsB from which fkbD and tcsB genes were deleted was deposited under the terms of the Budapest Treaty with the International Strain Depositary at the Korean Collection for Type Cultures (KCTC) of the Korea Research Institute of Bioscience and Biotechnology on Jul. 17, 2018 (accession number: KCTC13579BP).

9-Deoxo-FK523 was prepared by culturing the constructed production strain Streptomyces kanamyceticus ΔfkbD,tcsB (accession number: KCTC13579BP). This will be described in more detail. 50 mL of an R2YE medium (including 103 g/L sucrose, 10 g/L glucose, 0.25 g/L $K_2SO_4$, 10.12 g/L $MgCl_2 \cdot 6H_2O$, 0.1 g/L casamino acid, 50 mL/L yeast extract (10%), 100 mL/L TES buffer (5.73%, pH 7.2), 10 mL/L potassium phosphate (0.5%), 80 mL/L $CaCl_2 \cdot 2H_2O$ (3.68%), 15 mL/L L-proline (20%), 2 mL/L trace element solution, and 5 mL/L NaOH (1 N)) was added to a 250 mL baffled flask, and the production strain was inoculated thereinto. Then, the strain was pre-incubated in a rotary shaker incubator at 28° C. and 180 rpm for two days. Subsequently, 10 mL of the pre-incubated culture was inoculated into 1 L of the R2YE medium contained in a 3 L Erlenmeyer flask. After inoculation, the strain was incubated at 28° C. and 180 rpm for 6 days. After 6 days of the incubation, 9-deoxo-FK523 produced thereby was extracted by using a first extraction process.

The first extraction process was performed as follows. First, methanol was added to the culture broth in an equal volume and mixed for 30 minutes, and the microbial cells were removed by centrifugation, and then an extract from which the microbial cells were removed was concentrated using a rotary evaporator. After the concentrated extract was dissolved in water, ethyl acetate was added in twice the volume of the extract and mixed, and the mixture was left until layers were separated. After the layers were separated, an upper layer, i.e., an organic solvent layer, was recovered and concentrated using a rotary evaporator, and a weight after concentration was measured. The extract obtained by way of the first extraction process was passed through a column filled with silica gel. In this case, an amount of the silica gel was 15 times the weight of the extract obtained by way of the first extraction process, and methanol and methylene chloride mixed in five ratios (Aliquot 1. 0:100, Aliquot 2. 1:100, Aliquot 3. 1:10, Aliquot 4. 1:1, and Aliquot 5. 100:0) were used as mobile phases. In Aliquot 3, 9-deoxo-FK523 was confirmed. Aliquot 3 obtained as described above was concentrated using a rotary evaporator and ultimately purified by HPLC.

The concentrate was lyophilized to obtain 9-deoxo-FK523 represented by Formula 8 in the form of powder.

The prepared 9-deoxo-FK523 was identified as follows. Specifically, high-performance liquid chromatography analysis, mass spectrometry, and nuclear magnetic resonance analysis were conducted. Analysis results of 9-deoxo-FK523 are shown in Table 10 and FIGS. 43 to 48, and it was confirmed that 9-deoxo-FK523 was produced by the constructed production strain Streptomyces kanamyceticus ΔfkbD,tcsB based on the results.

Analysis results of 9-deoxo-FK523 (molecular formula: $C_{42}H_{69}NO_{11}$ and molecular weight: 764.01) are shown in Table 10 below.

TABLE 10

| Analysis method | Analysis results | | |
|---|---|---|---|
| High-performance liquid chromatography analysis | HPLC was performed using a 45-55% acetonitrile aqueous solution as a mobile phase at a flow rate of 1 mL/min and analyzed using a UV detector at 205 nm. In this regard, a retention time of 9-deoxo-FK523 was 24 minutes. | | |
| Mass spectrometry | (ESI-HR-MS) Calcd. for $C_{42}H_{69}NNaO_{11}^+$: 786.4763, found: m/z 786.4769 | | |
| | No. | carbon (ppm) | proton (ppm) |
| Nuclear magnetic resonance analysis | 1 | 169.61 | |
| | 2 | 52.59 | 4.85 (1H, br d, J = 5.0 Hz) |
| | 3 | 26.87 | 1.70 (1H, m), 2.24 (1H, m) |
| | 4 | 20.70 | 1.31 (1H, m), 1.72 (1H, m) |
| | 5 | 24.42 | 1.51 (1H, m), 1.68 (1H, m) |

TABLE 10-continued

| | | |
|---|---|---|
| 6 | 42.65 | 3.19 (1H, m), 3.69 (1H, m) |
| 7 | 174.23 | |
| 8 | 36.25 | 2.51 (1H, d, J = 15.0 Hz), 2.70 (1H, d, J = 15.0 Hz) |
| 9 | 98.70 | |
| 10 | 38.72 | 1.58 (1H, m) |
| 11 | 32.84 | 1.60 (1H, m), 1.94 (1H, m) |
| 12 | 74.60 | 3.40 (1H, m) |
| 13 | 70.90 | 3.86 (1H, dd, J = 10.0 Hz, 5.0 Hz) |
| 14 | 77.11 | 3.53 (1H, m) |
| 15 | 36.48 | 1.34 (1H, m), 1.47 (1H, m) |
| 16 | 26.30 | 1.50 (1H, m) |
| 17 | 48.49 | 1.65 (1H, m), 2.32 (1H, m) |
| 18 | 140.43 | |
| 19 | 123.48 | 5.17 (1H, d, J = 5.0 Hz) |
| 20 | 53.45 | 3.21 (1H, d, J = 5.0 Hz) |
| 21 | 215.35 | |
| 22 | 41.74 | 2.21 (1H, br d, J = 15 Hz), 2.66 (1H, br d, J = 15 Hz) |
| 23 | 69.99 | 4.01 (1H, m) |
| 24 | 40.68 | 1.90 (1H, m) |
| 25 | 76.62 | 5.22 (1H, br s) |
| 26 | 132.71 | |
| 27 | 128.92 | 4.98 (1H, d, J = 5.0 Hz) |
| 28 | 35.13 | 2.35 (1H, m) |
| 29 | 35.13 | 0.93 (1H, m), 2.01 (1H, m) |
| 30 | 84.43 | 3.00 (1H, m) |
| 31 | 73.80 | 3.39 (1H, m) |
| 32 | 32.87 | 1.34 (1H, m), 1.98 (1H, m) |
| 33 | 31.44 | 1.06 (1H, m), 1.61 (1H, m) |
| 34 | 17.13 | 1.18 (3H, d, J = 5 Hz) |
| 35 | 17.13 | 0.96 (3H, d, J = 5 Hz) |
| 36 | 18.87 | 0.78 (3H, d, J = 5 Hz) |
| 37 | 16.08 | 1.63 (3H, s) |
| 38 | 10.12 | 0.90 (3H, d, J = 5 Hz) |
| 39 | 14.79 | 1.66 (3H, s) |
| 40 | 56.38 | 3.37 (3H, s) |
| 41 | 57.90 | 3.37 (3H, s) |
| 42 | 56.81 | 3.41 3H, s) |

The obtained compound had the same molecular weight to that of 9-deoxo-31-O-demethyl-FK520. Although the compound consisting of a total of 42 carbon atoms had a very similar structure thereto based on $^1$H-NMR, $^{13}$C-NMR, and gHSQC data, the compound was confirmed as a structural isomer since a methoxy group ($\delta_H$ 3.41 and $\delta_C$ 56.81) was additionally observed, and one fewer CH$_2$ functional group was observed, unlike 9-deoxo-31-O-demethyl-FK520. As a result of identifying proton coupling by gCOSY, it was confirmed that the compound had a pipecolyl backbone based on coupling of H-2 to H-5. Based on gHMBC, the methyl group ($\delta_H$ 1.18 and $\delta_C$ 17.13) observed in a double coupled state was correlated with C-21 ($\delta_H$ 3.21 and $\delta_C$ 53.45), and thus it was confirmed that a methyl group constituting FK523 was present at C-21. Based thereon, the structure of the compound was determined as 9-deoxo-FK523.

Example 9: Preparation of 9-deoxo-31-O-demethyl-FK523

*Streptomyces kanamyceticus* ΔfkbD-fkbM,tcsB (accession number: KCTC13582BP), which is a 9-deoxo-31-O-demethyl-FK523-producing strain, was constructed by inactivating fkbD-fkbM and tcsB genes of *Streptomyces kanamyceticus*, which is an FK506-producing strain, via an in-frame deletion caused by a double cross-over homologous recombination, according to a method introduced by Ban, Y. H. et al., (*J. Nat. Prod.* 2013, 76, 1091-1098).

Specifically, in order to construct a mutant of the FK506-producing *Streptomyces kanamyceticus* strain from which fkbD-fkbM and tcsB genes were deleted, each gene was cloned to a pKC1139 vector and transferred to *Escherichia coli* ET12567/pUZ8002, and then the FK506-producing *Streptomyces kanamyceticus* strain was transformed with the vector by conjugation.

A method of constructing the strain may be explained more specifically as construction of an in-frame gene deletion plasmid and construction of a gene-deleted strain.

In the construction of the in-frame gene deletion plasmid, the *E. coli-Streptomyces* shuttle vector pKC1139 was used for in-frame gene deletion. Construction of the plasmid was performed by PCR of left- and right-flanking fragments of a target gene for deletion of Fosmid DNA derived from *Streptomyces kanamyceticus*. For deletion of the fkbD-fkbM gene, a primer pair of a left-flanking fragment, FkbD-MLF/FkbD-MLR, and a pair of a right-flanking fragment, FkbD-MRF/FkbD-MRR, were designed. For deletion of the tcsB gene, a primer pair of a left-flanking fragment, TcsBLF/TcsBLR, and a pair of a right-flanking fragment, TcsBRF/TcsBRR, were designed. All PCR fragments were isolated, digested with HindIII-XbaI or XbaI-EcoRI, and cloned to the pKC1139 vector. Information on the strains, plasmids, and primers used in this example are shown in Tables 1 and 2.

The plasmids used for construction of the gene-deleted strain are shown in Table 1. A plasmid for removing both C9 hydroxylase and 31-O-methyltransferase, pΔfkbD-fkbM, was transferred to *E. coli* ET12567/pUZ8002 and introduced into *Streptomyces kanamyceticus* by conjugation to delete the target gene by homologous recombination. A strain in which single cross-over occurred between the deletion plasmid and the chromosome of *Streptomyces kanamyceticus* was selected by culturing an apramycin-resistant transconjugant in the presence of apramycin at 37° C. (non-permissive temperature for replication of a pSG5-based replicon). Then, acquired colonies were proliferated three times at 28° C. without selection to allow second cross-over. The obtained double cross-over mutant, i.e., ΔfkbD-fkbM, was selected as a phenotype of apramycin sensitivity and identified by PCR, and optionally by Southern blotting.

The tcsB gene was deleted using the same method as that used in deletion of the fkbD-fkbM gene by introducing pΔtcsB into the constructed fkbD-fkbM gene-deleted *Streptomyces kanamyceticus* ΔfkbD-fkbM. ΔfkbD-fkbM,tcsB was selected as a phenotype of apramycin sensitivity and identified by PCR, and optionally by Southern blotting.

The constructed strain *Streptomyces kanamyceticus* ΔfkbD-fkbM,tcsB from which fkbD-fkbM and tcsB genes were deleted was deposited under the terms of the Budapest Treaty with the International Strain Depositary at the Korean Collection for Type Cultures (KCTC) of the Korea Research Institute of Bioscience and Biotechnology on Jul. 17, 2018 (accession number: KCTC13582BP).

9-Deoxo-31-O-demethyl-FK523 was prepared by culturing the constructed production strain *Streptomyces kanamyceticus* ΔfkbD-fkbM,tcsB (accession number: KCTC13582BP). This will be described in more detail. 50 mL of an R2YE medium (including 103 g/L sucrose, 10 g/L glucose, 0.25 g/L $K_2SO_4$, 10.12 g/L $MgCl_2 \cdot 6H_2O$, 0.1 g/L casamino acid, 50 mL/L yeast extract (10%), 100 mL/L TES buffer (5.73%, pH 7.2), 10 mL/L potassium phosphate (0.5%), 80 mL/L $CaCl_2 \cdot 2H_2O$ (3.68%), 15 mL/L L-proline (20%), 2 mL/L trace element solution, and 5 mL/L NaOH (1 N)) was added to a 250 mL baffled flask, and the production strain was inoculated thereinto. Then, the strain was pre-incubated in a rotary shaker incubator at 28° C. and 180 rpm for two days. Subsequently, 10 mL of the pre-incubated culture was inoculated into 1 L of the R2YE medium contained in a 3 L Erlenmeyer flask. After inoculation, the strain was incubated at 28° C. and 180 rpm for 6 days. After 6 days of the incubation, 9-deoxo-31-O-demethyl-FK523 produced thereby was extracted by using a first extraction process.

The first extraction process was performed as follows. First, methanol was added to the culture broth in an equal volume and mixed for 30 minutes, and the microbial cells were removed by centrifugation, and then an extract from which the microbial cells were removed was concentrated using a rotary evaporator. After the concentrated extract was dissolved in water, ethyl acetate was added in twice the volume of the extract and mixed, and the mixture was left until layers were separated. After the layers were separated, an upper layer, i.e., an organic solvent layer, was recovered and concentrated using a rotary evaporator, and a weight after concentration was measured. The extract obtained by way of the first extraction process was passed through a column filled with silica gel. In this case, an amount of the silica gel was 15 times the weight of the extract obtained by way of the first extraction process, and methanol and methylene chloride mixed in five ratios (Aliquot 1. 0:100, Aliquot 2. 1:100, Aliquot 3. 1:10, Aliquot 4. 1:1, and Aliquot 5. 100:0) were used as mobile phases. In Aliquot 3, 9-deoxo-31-O-demethyl-FK523 was confirmed. Aliquot 3 obtained as described above was concentrated using a rotary evaporator and ultimately purified by HPLC.

The concentrate was lyophilized to obtain 9-deoxo-31-O-demethyl-FK523 represented by Formula 9 in the form of powder.

The prepared 9-deoxo-31-O-demethyl-FK523 was identified as follows. Specifically, high-performance liquid chromatography analysis, mass spectrometry, and nuclear magnetic resonance analysis were conducted. Analysis results of 9-deoxo-31-O-demethyl-FK523 are shown in Table 11 and FIGS. 49 to 54, and it was confirmed that 9-deoxo-31-O-demethyl-FK523 was produced by the constructed production strain *Streptomyces kanamyceticus* ΔfkbD-fkbM,tcsB based on the results.

Analysis results of 9-deoxo-31-O-demethyl-FK523 (molecular formula: $C_{41}H_{67}NO_{11}$ and molecular weight: 752.01) are shown in Table 11 below.

TABLE 11

| Analysis method | Analysis results | | |
|---|---|---|---|
| High-performance liquid chromatography analysis | HPLC was performed using a 45-55% acetonitrile aqueous solution as a mobile phase at a flow rate of 1 mL/min and analyzed using a UV detector at 205 nm. In this regard, a retention time of 9-deoxo-31-O-demethyl-FK523 was 17 minutes. | | |
| Mass spectrometry | (ESI-HR-MS) Calcd. for $C_{41}H_{67}NNaO_{11}^+$: 772.4606, found: m/z 772.4612 | | |
| | No. | carbon (ppm) | proton (ppm) |
| Nuclear magnetic resonance analysis | 1 | 169.63 | |
| | 2 | 52.83 | 4.90 (1H, br d, J = 5.0 Hz) |
| | 3 | 26.88 | 1.70 (1H, m), 2.24 (1H, m) |
| | 4 | 20.70 | 1.31 (1H, m), 1.72 (1H, m) |
| | 5 | 24.70 | 1.51 (1H, m), 1.68 (1H, m) |
| | 6 | 42.89 | 3.21 (1H, m), 3.72 (1H, m) |
| | 7 | 174.26 | |
| | 8 | 36.25 | 2.51 (1H, d, J = 15.0 Hz), 2.70 (1H, d, J = 15.0 Hz) |
| | 9 | 98.70 | |
| | 10 | 38.72 | 1.58 (1H, m) |

TABLE 11-continued

| | | |
|---|---|---|
| 11 | 32.86 | 1.60 (1H, m), 1.94 (1H, m) |
| 12 | 74.59 | 3.40 (1H, m) |
| 13 | 70.90 | 3.86 (1H, dd, J = 10.0 Hz, 5.0 Hz) |
| 14 | 77.11 | 3.53 (1H, m) |
| 15 | 36.48 | 1.34 (1H, m), 1.47 (1H, m) |
| 16 | 26.30 | 1.50 (1H, m) |
| 17 | 48.37 | 1.65 (1H, m), 2.32 (1H, m) |
| 18 | 140.38 | |
| 19 | 123.50 | 5.17 (1H, d, J = 5.0 Hz) |
| 20 | 48.04 | 3.21 (1H, d, J = 5.0 Hz) |
| 21 | 215.35 | |
| 22 | 41.79 | 2.21 (1H, br d, J = 15 Hz), 2.66 (1H, br d, J = 15 Hz) |
| 23 | 69.99 | 4.01 (1H, m) |
| 24 | 40.60 | 1.90 (1H, m) |
| 25 | 76.70 | 5.22 (1H, br s) |
| 26 | 132.80 | |
| 27 | 128.83 | 4.98 (1H, d, J = 5.0 Hz) |
| 28 | 35.21 | 2.35 (1H, m) |
| 29 | 39.38 | 1.17 (1H, m), 1.91 (1H, m) |
| 30 | 75.71 | 3.43 (1H, m) |
| 31 | 75.17 | 3.36 (1H, m) |
| 32 | 32.24 | 1.34 (1H, m), 1.98 (1H, m) |
| 33 | 31.20 | 1.06 (1H, m), 1.61 (1H, m) |
| 34 | 17.09 | 1.18 (3H, d, J = 5 Hz) |
| 35 | 17.13 | 0.96 (3H, d, J = 5 Hz) |
| 36 | 18.86 | 0.78 (3H, d, J = 5 Hz) |
| 37 | 16.09 | 1.66 (3H, s) |
| 38 | 10.08 | 0.88 (3H, d, J = 5 Hz) |
| 39 | 14.73 | 1.67 (3H, s) |
| 40 | 56.38 | 3.37 (3H, s) |
| 41 | 57.90 | 3.36 3H, s) |

Based on $^1$H-NMR, $^{13}$C-NMR, and gHSQC data, the obtained compound consisting of a total of 41 carbon atoms had one fewer methoxy group unlike 9-deoxo-FK523. Together therewith, a $CH_2$ functional group ($\delta_H$ 2.70 and 2.51 and $\delta_C$ 36.25) generated by ΔfkbD-fkbM gene was observed. Based on 2D-NMR data, the structure of the compound was determined as 9-deoxo-31-O-demethyl-FK523.

Example 10: Identification of Immunosuppressive Activity of Nine Novel Compounds The degrees of decreases in immunosuppressive activity of the nine novel compounds were identified by a known in vitro T cell activity assay (J. Immunol. 143:718-726, 1989).

CD4+ T cell division is an indicator of immune response. When CD4+ T cells stained with Cell Trace™ Violet (CTV) proliferate by immune responses, the amount of CTV of each cell decreases, and thus the degrees of immunosuppressive activity were identified using this as an indicator.

Single cells were isolated from spleen of 6- to 8-week-old B6J experimental mice, and CD4+ T cells were isolated using a MagniSort® Mouse CD4 T cell Enrichment Kit (eBioscience). CD4+ T cells were stained with a Cell Trace™ Violet (CTV) Cell Proliferation Kit (Molecular Probes), and FK506 or the nine novel compounds were added thereto in concentrations of 0.01 ng/mL, 0.1 ng/mL, 1 ng/mL, 10 ng/mL, 100 ng/mL, and 1000 ng/mL, respectively, followed by incubation for 72 hours. In order to activate T cells, Dynabeads® Mouse T-Activator CD3/CD28 (Gibco) was used. As a control, inactivated T cells were used. After incubation, CTV intensity was analyzed by flow cytometry.

Figure 55:
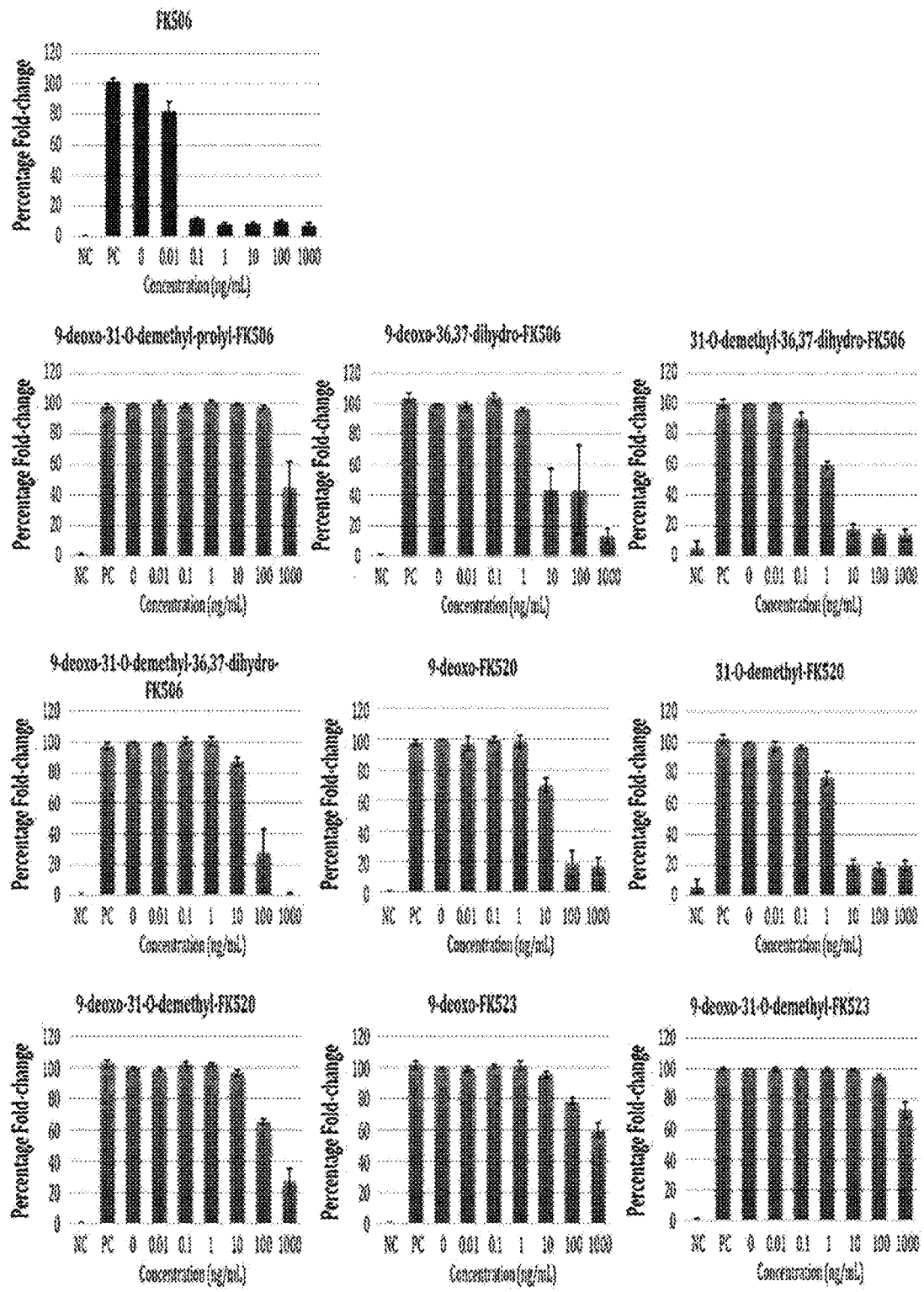
FIG. 55 shows degrees of decreases in immunosuppressive activity of the nine novel compounds of the present invention.

Table 12 below and FIG. 55 show the degrees of T cell proliferation based on CTV intensities measured using a flow cytometer, indicating the degrees of immunosuppressive activity of FK506 and the nine novel compounds. As shown in Table 12 below and FIG. 55, all novel compounds provided by the present invention exhibited reduced immunosuppressive activity compared to that of FK506.

TABLE 12

| Structural analogs | Immunosuppression $IC_{50}$ (ng/mL) |
|---|---|
| FK506 | 0.027 |
| 9-deoxo-prolyl-FK506 | 268.3 |
| 9-deoxo-FK506 | 0.513 |
| 31-O-demethyl-FK506 | 0.246 |
| 9-deoxo-31-O-demethyl-FK506 | 15.09 |
| 9-deoxo-31-O-demethyl-prolyl-FK506 | 886.5 |
| 9-deoxo-36,37-dihydro-FK506 | 14.1 |
| 31-O-demethyl-36,37-dihydro-FK506 | 1.723 |
| 9-deoxo-31-O-demethyl-36,37-dihydro-FK506 | 45.87 |
| 9-deoxo-FK520 | 24.98 |
| 31-O-demethyl-FK520 | 3.273 |
| 9-deoxo-31-O-demethyl-FK520 | 258.1 |
| 9-deoxo-FK523 | 1985 |
| 9-deoxo-31-O-demethyl-FK523 | 3378 |

Based on the results described above, it was confirmed that the nine novel compounds according to the present invention had significantly decreased immunosuppressive activity compared to FK506, and thus it was determined that the composition for promoting hair growth including at least one compound selected from the nine novel compounds as

Example 11: Identification of Hair Growth-Promoting Activity of Nine Novel Compounds Hair growth-promoting activity of the nine novel compounds of the present invention relative to that of the parent drug (FK506) was evaluated using vibrissae tissue of mice. The mouth and mouth tissue (whisker pad) around the mouth where thick hair grows were peeled off from each of 6- to 8-week-old experimental black mouse (C57BL/6 mouse) and treated with 70% for a short time of several seconds. The treated mouth tissue was prepared in a state of being immersed in phosphate-buffered saline (PBS) supplemented with 1% penicillin/streptomycin (P/S) on ice. Surrounding subcutaneous fat tissue and connective tissue were removed using forceps and blades while observing the prepared mouth tissue using a dissecting microscope to expose vibrissae tissue. Then, vibrissae were isolated from mouth tissue using forceps and blades with respect to hair follicles, and the vibrissae were added to the PBS containing 1% P/S. Subsequently, a vibrissae culture medium (serum-free Dulbecco's Modified Eagle Medium (DMEM) containing 1% P/S and 12.5 μg/mL gentamicin) was filled in a well plate, and each of the separated vibrissae was added to each well. In addition, they were incubated in an incubator at 37° C. with 5% $CO_2$ while changing the culture medium with a fresh culture medium every 2 days. In order to evaluate effects of the nine novel compounds on the growth of vibrissae, the nine novel compounds were mixed with the culture medium, and then evaluation was performed by measuring length, area, volume, and the like of vibrissae relative to reference values.

Figure 56:
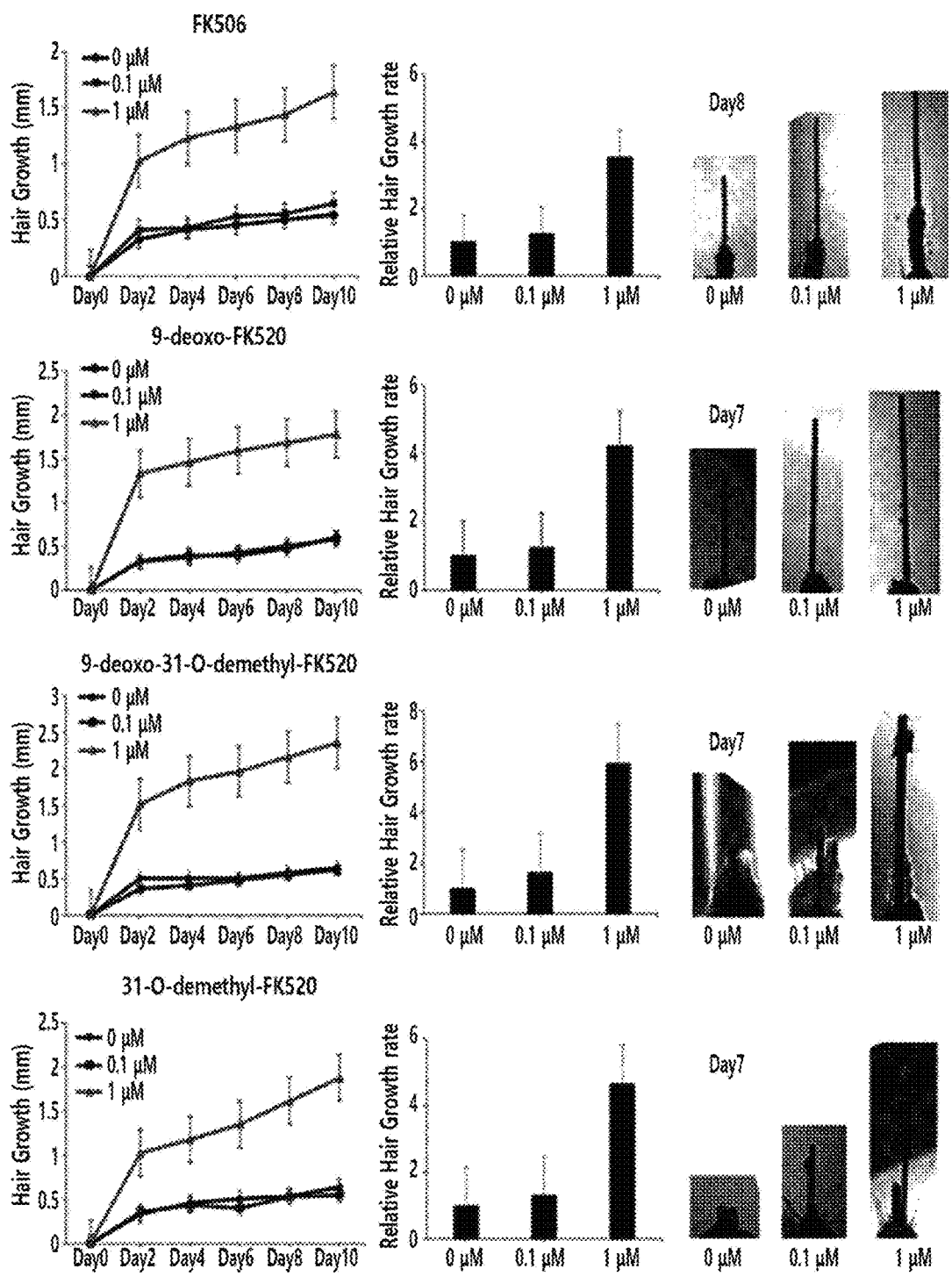
FIG. 56 shows hair growth-promoting activity of the novel compounds of the present invention.
Figure 57:
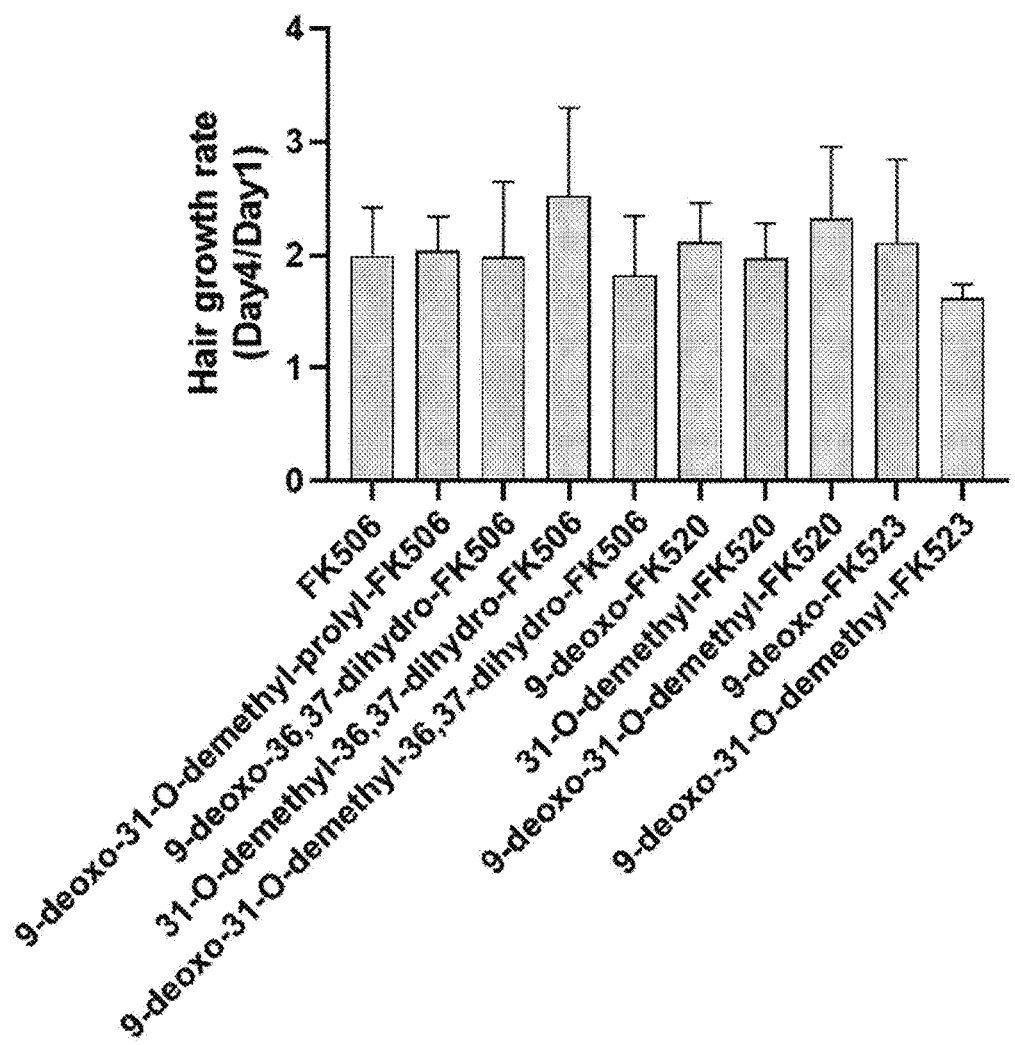
FIG. 57 shows hair growth-promoting activity of the novel compounds of the present invention by identifying increases in length of vibrissae.

As a result, it was confirmed that all of the nine novel compounds may provide the same level of hair growth-promoting activity as that of the parent drug, FK506. Results of some of the novel compounds are shown in FIG. 56 as representative examples. These examples are made for illustrative purposes instead of emphasizing particular compounds. Furthermore, results of measuring the growth of the vibrissae in the length by the novel compounds are shown in FIG. 57. As shown in FIG. 57, it was confirmed that the lengths of vibrissae increased due to both the novel compounds and FK506.

Figure 58:
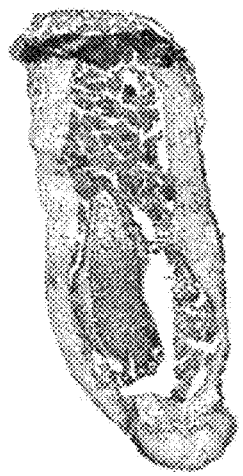
FIG. 58 shows results of investigation of hair growth-promoting activity based on histological results of vibrissae treated with the novel compounds of the present invention.
Figure 58:
Figure 58:
Figure 58:
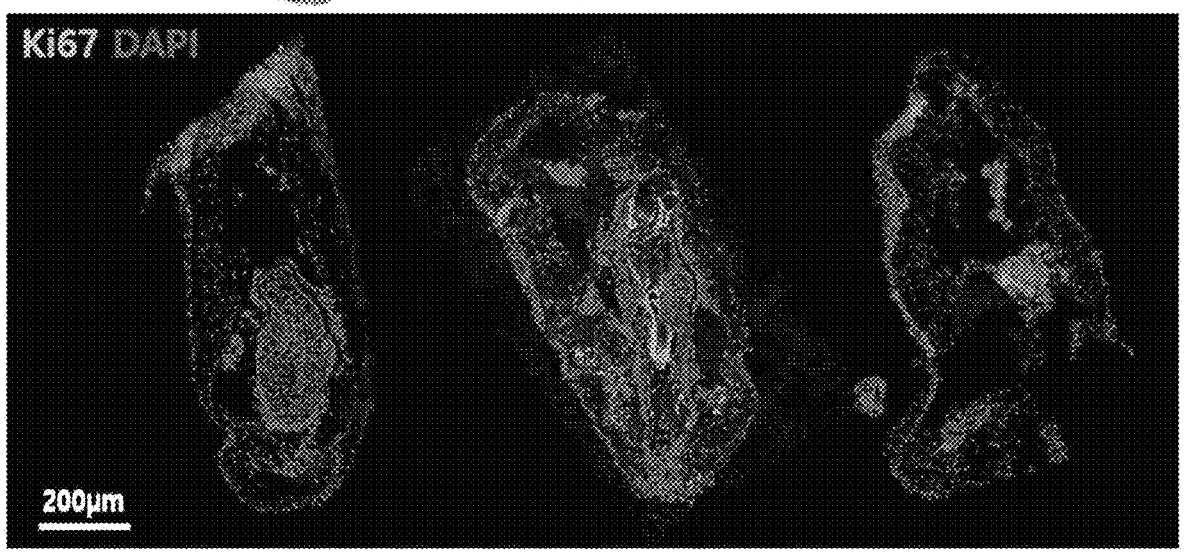

Also, histological results of vibrissae cultured in a state of being treated with some of the novel compounds are shown in FIG. 58. It was confirmed that a growth marker (Ki67) of cells was overexpressed due to the novel compound 9-deoxo-31-O-demethyl-FK520 compared to an untreated group, and thus it was confirmed that the growth of vibrissae treated with the novel compound was continuously maintained. Based on the results, it was confirmed that the composition for promoting hair growth, including at least one of the nine novel compounds of the present invention as an active ingredient, had the effects on promoting hair growth as desired, and thus it was determined that the composition may be effectively used for preventing and treating hair loss.

The above description of the present invention is provided for the purpose of illustration, and it would be understood by those skilled in the art that various changes and modifications may be made without changing the technical conception and essential features of the present invention. Thus, it is clear that the above-described embodiments are illustrative in all aspects and do not limit the present invention. The various embodiments disclosed herein are not intended to be limiting, with the true scope and spirit being indicated by the following claims. The present invention is to be limited only by the terms of the appended claims, along with the full scope of equivalents to which such claims are entitled.

The invention claimed is:
1. A method of promoting hair growth or treating hair loss, the method comprising a step of administering to a subject a pharmaceutically effective amount of a compound selected from the group consisting of 9-deoxo-31-O-demethyl-prolyl-FK506 represented by Formula 1 below, 9-deoxo-36,37-dihydro-FK506 represented by Formula 2 below, 31-O-demethyl-36,37-dihydro-FK506 represented by Formula 3 below, 9-deoxo-31-O-demethyl-36,37-dihydro-FK506 represented by Formula 4 below, 9-deoxo-FK520 represented by Formula 5 below, 31-O-demethyl-FK520 represented by Formula 6 below, 9-deoxo-31-O-demethyl-FK520 represented by Formula 7 below, 9-deoxo-FK523 represented by Formula 8 below, and 9-deoxo-31-O-demethyl-FK523 represented by Formula 9 below, or a pharmaceutically acceptable salt thereof:

[Formula 1]
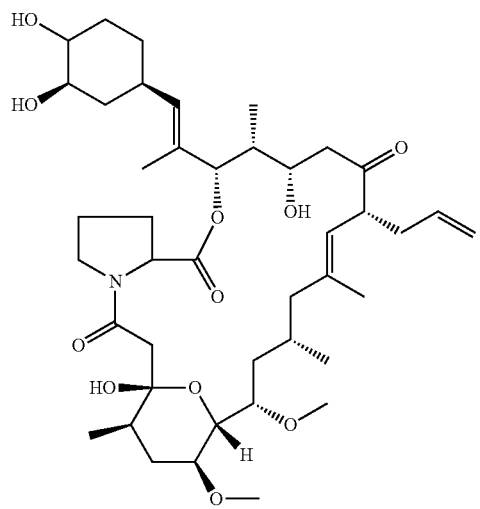
[Formula 2]
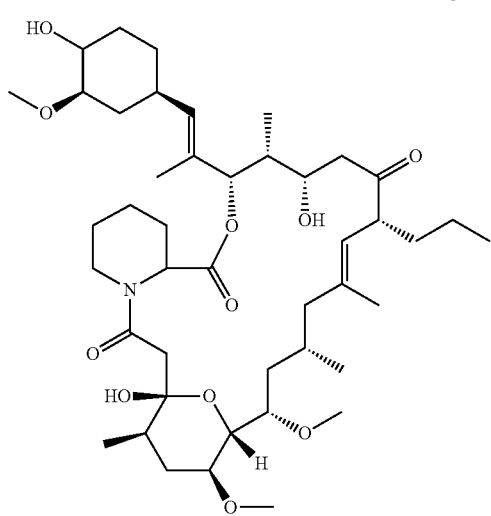
[Formula 3]
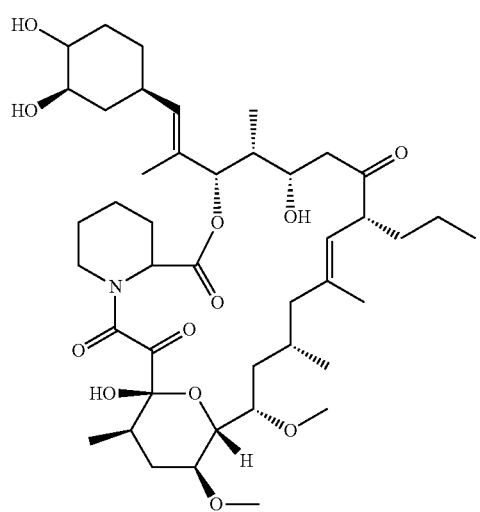
[Formula 4]
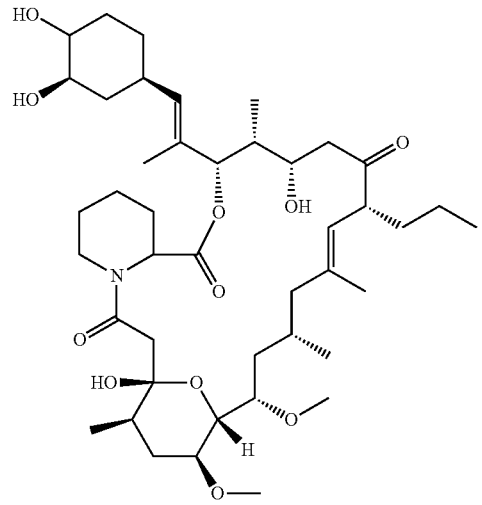
[Formula 5]
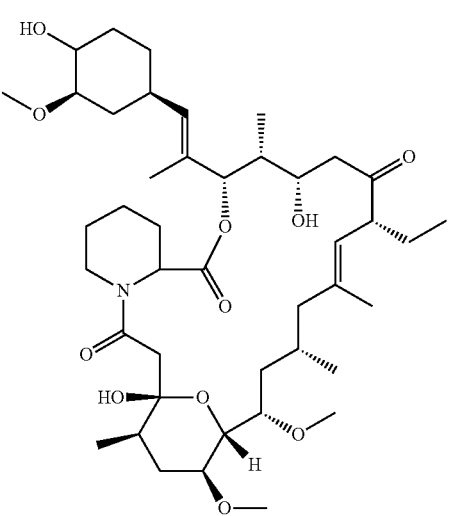
[Formula 6]
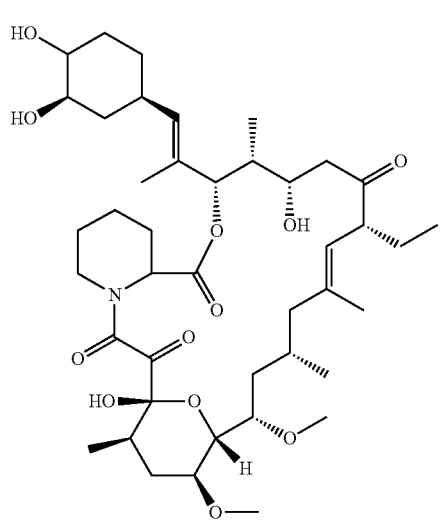

-continued

[Formula 7]
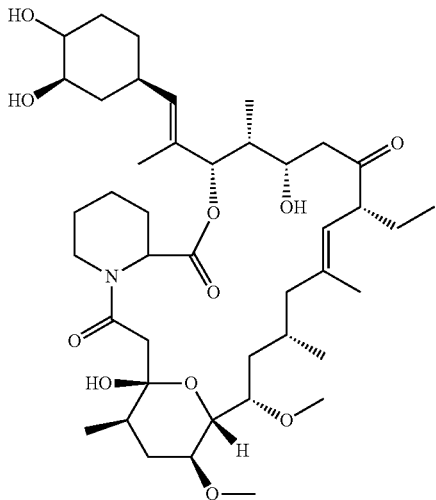

[Formula 8]
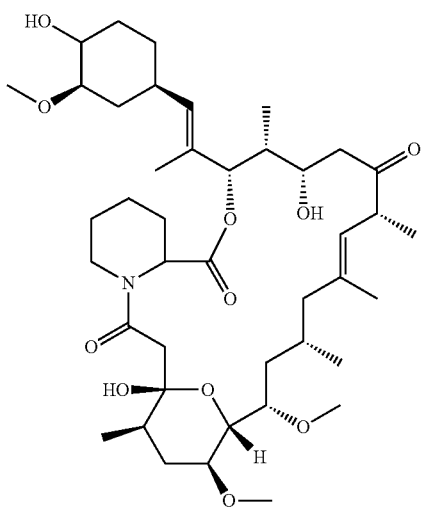

[Formula 9]
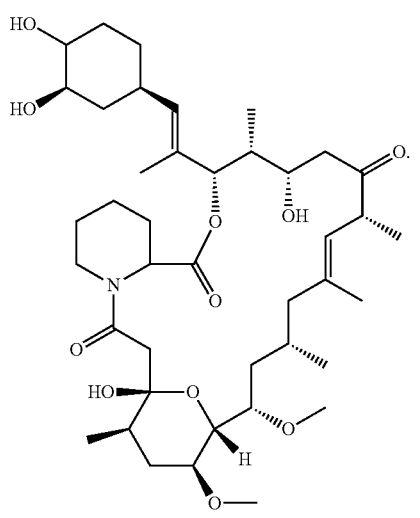

wherein the compound has reduced immunosuppressive activity compared to FK506.

2. The method of claim 1, wherein the hair loss comprises cicatricial alopecia; or at least one non-cicatricial alopecia selected from the group consisting of infectious hair loss, traumatic hair loss, inflammatory hair loss, congenital hair loss, endocrine hair loss, alopecia neoplastica, malnutrition hair loss, drug-induced hair loss, hair loss caused by abnormal hair structure, male-pattern hair loss, female-pattern hair loss, and alopecia areata.

3. The method of claim 1, wherein the 9-deoxo-31-O-demethyl-prolyl-FK506 is produced by culturing *Streptomyces kanamyceticus* ΔfkbD-fkbM deposited under accession number KCTC13581BP.

4. The method of claim 1, wherein the 9-deoxo-36,37-dihydro-FK506 is produced by culturing *Streptomyces kanamyceticus* ΔfkbD, tcsD deposited under accession number KCTC13580BP.

5. The method of claim 1, wherein the 31-O-demethyl-36,37-dihydro-FK506 is produced by culturing *Streptomyces kanamyceticus* ΔfkbM, tcsD deposited under accession number KCTC13584BP.

6. The method of claim 1, wherein the 9-deoxo-31-O-demethyl-36,37-dihydro-FK506 is produced by culturing *Streptomyces kanamyceticus Streptomyces kanamyceticus* ΔfkbD-fkbM, tcsD deposited under accession number KCTC13585BP.

7. The method of claim 1, wherein the 9-deoxo-FK520 is produced by culturing *Streptomyces kanamyceticus* ΔfkbD, tcsB deposited under accession number KCTC13579BP or *Streptomyces kanamyceticus* ΔfkbD, tcsD deposited under accession number KCTC13580BP.

8. The method of claim 1, wherein the 31-O-demethyl-FK520 is produced by culturing *Streptomyces kanamyceticus* ΔfkbM, tcsB deposited under accession number KCTC13583BP or *Streptomyces kanamyceticus* ΔfkbM, tcsD deposited under accession number KCTC13584BP.

9. The method of claim 1, wherein the 9-deoxo-31-O-demethyl-FK520 is produced by culturing *Streptomyces kanamyceticus* ΔfkbD-fkbM, tcsB deposited under accession number KCTC13582BP or *Streptomyces kanamyceticus* ΔfkbD-fkbM, tcsD deposited under accession number KCTC13585BP.

10. The method of claim 1, wherein the 9-deoxo-FK523 is produced by culturing *Streptomyces kanamyceticus* ΔfkbD, tcsB deposited under accession number KCTC13579BP.

11. The method of claim 1, wherein the 9-deoxo-31-O-demethyl-FK523 is produced by culturing *Streptomyces kanamyceticus* ΔfkbD-fkbM, tcsB deposited under accession number KCTC13582BP.

* * * * *